United States Patent
Iafrate et al.

(10) Patent No.: US 11,781,179 B2
(45) Date of Patent: *Oct. 10, 2023

(54) METHODS FOR DETERMINING A NUCLEOTIDE SEQUENCE CONTIGUOUS TO A KNOWN TARGET NUCLEOTIDE SEQUENCE

(71) Applicant: THE GENERAL HOSPITAL CORPORATION, Boston, MA (US)

(72) Inventors: Anthony John Iafrate, Newton, MA (US); Long Phi Le, Boston, MA (US); Zongli Zheng, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/897,588

(22) Filed: Jun. 10, 2020

(65) Prior Publication Data

US 2021/0062253 A1 Mar. 4, 2021

Related U.S. Application Data

(63) Continuation of application No. 15/984,612, filed on May 21, 2018, now Pat. No. 10,718,009, which is a
(Continued)

(51) Int. Cl.
*C12Q 1/6855* (2018.01)
*C12Q 1/6874* (2018.01)
*C12Q 1/6806* (2018.01)

(52) U.S. Cl.
CPC ......... *C12Q 1/6855* (2013.01); *C12Q 1/6806* (2013.01); *C12Q 1/6874* (2013.01);
(Continued)

(58) Field of Classification Search
CPC .. C12Q 1/6855; C12Q 1/6806; C12Q 1/6874; C12Q 2525/155; C12Q 2525/161;
(Continued)

(56) References Cited

U.S. PATENT DOCUMENTS

| 4,868,104 A | 9/1989 | Kurn et al. |
| 5,565,340 A | 10/1996 | Chenchik et al. |

(Continued)

FOREIGN PATENT DOCUMENTS

| AU | 2005203617 A1 | 9/2005 |
| EP | 0356021 A2 | 2/1990 |

(Continued)

OTHER PUBLICATIONS

Verbeek et al. The Effects of Four Different Tyrosine Kinase Inhibitors on Medullary and Papillary Thyroid Cancer Cells. Journal of Clinical Endocrinology and Metabolism 2011; 96: E991-E995 (Year: 2011).*

(Continued)

*Primary Examiner* — Angela M. Bertagna
(74) *Attorney, Agent, or Firm* — Nixon Peabody LLP; David S. Resnick; Ravinderjit S. Braich

(57) ABSTRACT

The technology described herein is directed to methods of determining oligonucleotide sequences, e.g. by enriching target sequences prior to sequencing the sequences.

14 Claims, 11 Drawing Sheets

Specification includes a Sequence Listing.

Related U.S. Application Data continuation of application No. 15/269,448, filed on Sep. 19, 2016, now Pat. No. 10,017,810, which is a continuation of application No. 13/793,564, filed on Mar. 11, 2013, now Pat. No. 9,487,828.

(60) Provisional application No. 61/679,302, filed on Aug. 3, 2012, provisional application No. 61/645,364, filed on May 10, 2012.

(52) U.S. Cl.
CPC . *C12Q 2525/155* (2013.01); *C12Q 2525/161* (2013.01); *C12Q 2525/191* (2013.01); *C12Q 2531/113* (2013.01); *C12Q 2549/119* (2013.01)

(58) Field of Classification Search
CPC ........ C12Q 2525/191; C12Q 2531/113; C12Q 2549/119
See application file for complete search history.

(56) References Cited

U.S. PATENT DOCUMENTS

| | | | |
|---|---|---|---|
| 5,827,658 | A | 10/1998 | Liang |
| 6,087,101 | A | 7/2000 | Gruelich et al. |
| 6,172,214 | B1 | 1/2001 | Brenner |
| 6,576,448 | B2 | 6/2003 | Weissman et al. |
| 6,632,611 | B2 | 10/2003 | Su et al. |
| 6,833,246 | B2 | 12/2004 | Balasubramanian |
| 7,214,490 | B2 | 5/2007 | Su et al. |
| 7,244,559 | B2 | 7/2007 | Rothberg et al. |
| 7,273,730 | B2 | 9/2007 | Du Breuil et al. |
| 7,824,856 | B2 | 11/2010 | Montforte |
| 9,487,828 | B2 | 11/2016 | Iafrate et al. |
| 10,017,810 | B2 | 7/2018 | Iafrate et al. |
| 10,718,009 | B2 * | 7/2020 | Iafrate ..................... A61P 35/00 |
| 2002/0086317 | A1 | 7/2002 | Nagayama |
| 2003/0104432 | A1 | 6/2003 | Xu et al. |
| 2003/0143553 | A1 | 7/2003 | Sommer |
| 2004/0053260 | A1 | 3/2004 | Gut et al. |
| 2007/0172824 | A1 | 7/2007 | Chun |
| 2009/0131275 | A1 | 5/2009 | Shimamoto et al. |
| 2009/0203085 | A1 | 8/2009 | Kurn et al. |
| 2010/0248310 | A1 | 9/2010 | Morley |
| 2010/0286143 | A1 | 11/2010 | Dias Santagata et al. |
| 2012/0122701 | A1 | 5/2012 | Ryan et al. |
| 2013/0005585 | A1 | 1/2013 | Anderson et al. |
| 2013/0231253 | A1 | 9/2013 | Amorese et al. |
| 2013/0303461 | A1 | 11/2013 | Iafrate et al. |
| 2015/0011396 | A1 | 1/2015 | Schroeder et al. |
| 2015/0140553 | A1 | 5/2015 | Cushing et al. |
| 2015/0252361 | A1 | 9/2015 | Hayden et al. |
| 2018/0127806 | A1 | 5/2018 | Stahl et al. |
| 2018/0155767 | A1 | 6/2018 | Myers et al. |

FOREIGN PATENT DOCUMENTS

| | | | |
|---|---|---|---|
| JP | 2005245297 | A | 9/2005 |
| WO | 1997/023646 | A1 | 7/1997 |
| WO | 1997/023647 | A1 | 7/1997 |
| WO | 1998/028443 | A1 | 7/1998 |
| WO | 1999/042618 | A1 | 8/1999 |
| WO | 2000/043544 | A1 | 7/2000 |
| WO | 2000/070095 | A2 | 11/2000 |
| WO | 2001/012859 | A2 | 2/2001 |
| WO | 2001/020035 | A2 | 3/2001 |
| WO | 2001083696 | A2 | 11/2001 |
| WO | 2002/000938 | A2 | 1/2002 |
| WO | 2002/029117 | A3 | 4/2002 |
| WO | 2002/048402 | A2 | 6/2002 |
| WO | 2002/072772 | A2 | 9/2002 |
| WO | 2003/078645 | A2 | 9/2003 |
| WO | 2003/083435 | A2 | 10/2003 |
| WO | 2004/011665 | A2 | 2/2004 |
| WO | 2004/092418 | A2 | 10/2004 |
| WO | 2005/065321 | A2 | 7/2005 |
| WO | 2007/030759 | A2 | 3/2007 |
| WO | 2007/057652 | A1 | 5/2007 |
| WO | 2007/136717 | A1 | 11/2007 |
| WO | 2007129778 | A1 | 11/2007 |
| WO | 2008/005459 | A2 | 1/2008 |
| WO | 2008/093098 | A2 | 8/2008 |
| WO | 2009/102878 | A2 | 8/2009 |
| WO | 2009/102896 | A2 | 8/2009 |
| WO | 2009/117698 | A2 | 9/2009 |
| WO | 2009/133466 | A2 | 11/2009 |
| WO | 2009/148617 | A2 | 12/2009 |
| WO | 2010/077288 | A2 | 7/2010 |
| WO | 2010/083046 | A2 | 7/2010 |
| WO | 2011/019964 | A1 | 2/2011 |
| WO | 2011/032053 | A1 | 3/2011 |
| WO | 2011/053987 | A1 | 5/2011 |
| WO | 2011/156529 | A2 | 12/2011 |
| WO | 2012/003374 | A2 | 1/2012 |
| WO | 2012/040387 | A1 | 3/2012 |
| WO | 2012/044956 | A1 | 4/2012 |
| WO | 2012/064739 | A2 | 5/2012 |
| WO | 2012/103154 | A1 | 8/2012 |
| WO | 2012166425 | A1 | 12/2012 |
| WO | 2013/059746 | A1 | 4/2013 |
| WO | 2013/074833 | A1 | 5/2013 |
| WO | 2013/112923 | A1 | 8/2013 |
| WO | 2013122826 | A1 | 8/2013 |
| WO | 2013/191775 | A2 | 12/2013 |
| WO | 2014/144092 | A1 | 9/2014 |
| WO | 2014/150931 | A1 | 9/2014 |
| WO | 2015/073711 | A1 | 5/2015 |

OTHER PUBLICATIONS

Lennon et al. A scalable, fully automated process for construction of sequence-ready barcoded libraries for 454. Genome Biology 2010: 11: R15 (Year: 2010).*
Xiao et al. Sequential amplification of flanking sequences by Y-shaped adaptor dependent extension using multiple templates. Journal of Plant Physiology and Molecular Biology 2007; 33: 85-90 (Year: 2007).*
Zheng et al. Titration-free 454 sequencing using Y adapters. Nature Protocols 2011; 6: 1367-1376 (Year: 2011).*
Lamant et al. A New Fusion Gene TPM3-ALK in Anaplastic Large Cell Lymphoma Created by a (1;2)(q25;p23) Translocation. Blood 1999; 93: 3088-3095 (Year: 1999).*
Amsterdam et al. "Retroviral-mediated insertional mutagenesis in zebrafish." Methods in Cell Biology 104: 59-82 (2011).
Applied Biosystems. "Applied Biosystems 3130/3130xl Genetic Analyzers: Getting Started Guide." Retrieved from internet. URL: https://www.baylor.edu/content/services/document.php/186486.pdf. 196 pages (2004).
BIO S&T. "APAgene GOLD-RT Genome Walking Kits." Retrieved from internet. URL: https://search.cosmobio.co.jp/cosmo_search_p/search_gate2/docs/BAT_/BT901RT.20120614.pdf. 14 Pages (2010).
Bronner et al. "Improved protocols for illumina sequencing." Current Protocols in Human Genetics 79(1): p. 18.2.1-18.2.42.
Chiarle et al. "Genome-wide translocation sequencing reveals mechanisms of chromosome breaks and rearrangements in B cells." Cell 147(1): 107-119 (2011).
Cornish-Bowden. "Nomenclature for incompletely specified bases in nucleic acid sequences: recommendations 1984." Nucleic Acids Research 13(9): 3021-3030 (1985).
Craig et al. "Identification of genetic variants using bar-coded multiplexed sequencing." Nature Methods 5(10): 887-893 (2008).
Fraiture et al. "An innovative and integrated approach based on DNA walking to identify unauthorised GMOs." Food Chemistry 147: 60-69(2014).
Illumina. "16S Metagenomic Sequencing Library Preparation," Retrieved from the internet. URL: https://support.illumina.com/documents/documentation/chemistry_documentation/16s/16s-metagenomic-library-prep-guide-15044223-b.pdf. 28 pages (2013).

(56) References Cited

OTHER PUBLICATIONS

Illumina. "Genomic Sequencing." Retrieved from the internet. URL: https://www.illumina.com/documents/products/datasheets/datasheet_genomic_sequence.pdf. 6 pages (2010).
Illumina. "Illumina Sequencing Technology." Retrieved from the Internet. URL: https://studylib.net/doc/8828848/illumina-sequencing-technology. 5 pages (2010).
Illumina. "Multiplexing Sample Preparation Guide." Retrieved from the internet. URL: http://nextgen.mgh.harvard.edu/attachments/Multiplexing_SamplePrep_Guide_1005361_C.pdf. 35 pages (2010).
Illumina. "TruSeq RNA and DNA Library Preparation Kits v2." Retrieved from the internet. URL: https://www.illumina.com/documents/products/datasheets/datasheet_truseq_sample_prep_kits.pdf. 4 pages (2014).
Iskow et al. "Natural mutagenesis of human genomes by endogenous retrotransposons." Cell 141(7): 1253-1261 (2010).
Kircher et al. "Double indexing overcomes inaccuracies in multiplex sequencing on the Illumina platform." Nucleic Acids Research 40(1): e3 pp. 1-8 (2012).
Kircher et al. "Double indexing overcomes inaccuracies in multiplex sequencing on the Illumina platform." Nucleic Acids Research 40(1): e3 pp. 1-8 (2012) [Supplemental Information].
Leoni et al. "Genome walking in eukaryotes." The FEBS Journal 278(21): 3953-3977 (2011).
Liu et al. "Comparison of next-generation sequencing systems," Journal of Biomedicine and Biotechnology 2012: Article ID 251364 pp. 1-11 (2012).
Martin-Harris et al. "Gene walking using sequential hybrid primer polymerase chain reaction." Analytical Biochemistry 399(2): 308-310 (2010).
McCarty et al. "Mu-seq: sequence-based mapping and identification of transposon induced mutations." PLoS One 8 (10): e77172 pp. 1-11 (2013).
Metzker. "Emerging technologies in DNA sequencing." Genome Research 15(12): 1767-1776 (2005).
Metzker. "Sequencing technologies—the next generation." Nature Reviews Genetics 11(1): 31-46 (2010).
Meuzelaar et al. "MegaPlex PCR: a strategy for multiplex amplification." Nature Methods 4(10): 835-837 (2007).
Myllykangas et al., "Efficient targeted resequencing of human germline and cancer genomes by oligonucleotide-selective sequencing", Nat. Biotechnol. 29(11):1024-1027 (2011) [Supplemental Information].
Newton et al. "Analysis of any point mutation in DNA. The amplification refractory mutation system (ARMS)." Nucleic Acids Research 17(7): 2503-2516 (1989).
Quail et al. "A tale of three next generation sequencing platforms: comparison of Ion Torrent, Pacific Biosciences and Illumina MiSeq sequencers." BMC Genomics 13(1): 1-13 (2012).
Siebert et al. "An improved PCR method for walking in uncloned genomic DNA." Nucleic Acids Research 23(6): 1087-1088 (1995).
Skerra. "Phosphorothioate primers improve the amplification of DNA sequences by DNA polymerases with proofreading activity." Nucleic Acids Research 20(14): 3551-3554 (1992).
Wang et al. "Efficient genome-wide mutagenesis of zebrafish genes by retroviral insertions." Proceedings of the National Academy of Sciences 104(30): 12428-12433 (2007).
Wu et al. "Transcription start regions in the human genome are favored targets for MLV integration." Science 300 (5626): 1749-1751 (2003).
Frohman et al., "Rapid production of full-length cDNAs from rare transcripts: amplification using a single gene-specific oligonucleotide primer." PNAS 85(23):8998-9002 (1988).
Kim et al., "Genetic-based biomarkers and next-generation sequencing: the future of personalized care in colorectal cancer", Per Med. 8(3):331-345 (2011).
Lamant et al., "A New Fusion Gene TPM3-ALK in Anaplastic Large Cell Lymphoma Created by a (1;2)(q25;p23) Translocation", Blood 93(9):3088-3095 (1999).

Lennon et al., "A scalable, fully automated process for construction of sequence-ready barcoded libraries for 454", Genome Biology 11:R15 (2010).
Natsoulis et al., "Identification of Insertion Deletion Mutations from Deep Targeted Resequencing", J Data Mining Genomics Proteomics 4(3) (2013).
Newburger et al., "The Human OligoGenome Resource: a database of oligonucleotide capture probes for resequencing target regions across the human genome", Nucleic Acids Research 40(Database issue):D1137-D1143 (2012).
Scheinin et al., "CanGEM: mining gene copy number changes in cancer", Nucleic Acids Research 36(Database issue):D830-835 (2008).
Schiffman et al., "Molecular inversion probes reveal patterns of 9p21 deletion and copy number aberrations in childhood leukemia", Cancer Genet Cytogenet. 193(1):9-18 (2009).
Schiffman et al., "Oncogenic BRAF Mutation with CDKN2A Inactivation is Characteristic of a Subset of Pediatric Malignant Astrocytomas", Cancer Res. 70(2):512-519 (2010).
Shendure et al., "Next-generation DNA sequencing", Nature Biotechnology 26(10):1135-1145 (2008).
Singh et al., "Microarray-based comparison of three amplification methods for nanogram amounts of total RNA", Am J Physiol Cell Physiol. 288(5):C1179-C1189 (2005).
Sinkkonen et al., "Serial Analysis of Gene Expression in the Chicken Otocyst", JARO 12(6):697-710 (2011).
Tong et al., "Genome-scale identification of conditionally essential genes in E. coli by DNA microarrays", Biochemical and Biophysical Research Communications 322(1):347-354 (2004).
Turner et al., "Gene Expression Profiling of RNA Extracted from FFPE Tissues: NuGEN Technologies' Whole-Transcriptome Amplification System", Methods Mol Biol. 724:269-280 (2011).
Wang et al. "Fusion primer and nested integrated PCR (FPNI-PCR): a new high-efficiency strategy for rapid chromosome walking or flanking sequence cloning." BMC Biotechnology 11(1):109 (2011).
Yuanxin et al. "T-linker-specific ligation PCT (T-linker PCR): an advanced PCR technique for chromosome walking or for isolation of tagged DNA ends", Nucleic Acids Research 31(12):e68 (2003).
Zhang et al., "Detecting simultaneous changepoints in multiple sequences", Biometrika 97(3):631-645 (2010).
Illumina. "High-Speed, Multiplexed 16S Amplicon Sequencing on the MiSeq System." Retrieved from the internet. URL: https://cpb-us-e1.wpmucdn.com/blog.uta.edu/dist/4/4833/files/2020/08/appnote_16s_sequencing.pdf. 4 pages (2013).
Kim et al., "FISH-negative cryptic PML-RARA rearrangement detected by long-distance polymerase chain reaction and sequencing analyses: a case study and review of the literature." Cancer Genetics and Cytogenetics 203 (2):278-283 (2010).
Myllykangas et al., "Efficient targeted resequencing of human germline and cancer genomes by oligonucleotide-selective sequencing", Nat Biotechnol. 29(11):1024-1027 (2011).
Ali et al. "Sequence Analysis of TnphoA Insertion Sites in Vibrio cholera Mutants Defective in Rugose Polysaccharide Production", Infection and Immunity 687:6857-6864 (2000).
Baetens et al. "Applying Massive Parallel Sequencing to Molecular Diagnosis of Marfan and Loeys-Dietz Syndromes", Human Mutation 32:1053-1062 (2011).
Bohmer, "Novel application for isothermal nucleic acid sequence-based amplification (NASBA)", Journal of Virological Methods 158(1-2):199-201 (2009).
Callaway et al., "A Sobemovirus coat protein gene complements long-distance movement of a coat protein-null Dianthovirus." Virology 330(1):186-195 (2004).
Chang et al., "Identification of a biomarker panel using a multiplex proximity ligation assay improves accuracy of pancreatic cancer diagnosis", Journal of Translational Medicine 7:105 (2009).
Chen et al., "Allele-specific copy No. profiling by next-generation DNA sequencing." Nucleic Acids Research 43 (4):e23 (2015).
Chenchik, et al., "Full-Length cDNA Cloning and Determination of mRNA 5' and 3' Ends by Amplification of Adaptor-Ligated cDNA", BioTechniques 21(3):526-534 (1996).
Compton, "Nucleic acid sequence-based amplification", Nature 350(6313): 91-92 (1991).

(56) References Cited

OTHER PUBLICATIONS

Cushing et al., "RVD: a command-line program for ultrasensitive rare single nucleotide variant detection using targeted next-generation DNA resequencing", BMC Research Notes 6:206 (2013).
Dafforn et al., "Linear mRNA amplification from as little as 5 ng total RNA for global gene expression analysis", BioRechniques 37(5):854-857 (2004).
Dahl et al., "Multigene amplification and massively parallel sequencing for cancer mutation discovery", PNAS 104 (22):9387-9392 (2007).
Flaherty et al., "Ultrasensitive detection of rare mutations using next-generation targeted resequencing", Nucleic Acids Research 40(1):e2 (2012).
Fredriksson et al., "Multiplex amplification of all coding sequences within 10 cancer genes by Gene-Collector", Nucleic Acids Research 35(7):e47 (2007).
Fredriksson et al., "Multiplexed protein detection by proximity ligation for cancer biomarker validation", Nature Methods 4(4):327-329 (2007).
Gould et al., "Analysis of sequence variation among smeDEF multi drug efflux pump genes and flanking DNA from defined 16S rRNA subgroups of clinical Stenotrophomonas maltophilia isolates." Journal of Antimicrobial Chemotherapy 54(2):348-353 (2004).
Grace et al., "Degradable dUMP Outer Primers in Merged Tandem (M/T)-Nested PCR: Low- and Single-Copy DNA Target Amplification", Analytical Biochemistry 263(1):85-92 (1998).
Green et al., "Hierarchy in somatic mutations arising during genomic evolution and progression of follicular lymphoma", Blood 121(9):1604-1611 (2013).
Grimes et al., "MendeLIMS: a web-based laboratory information management system for clinical genome sequencing", BMC Bioinformatics 15:290 (2014).
Guled et al., "Array comparative genomic hybridization analysis of olfactory neuroblastoma", Modern Pathology 21(6):770-778 (2008).
Head et al., "Method for improved Illumina sequencing library preparation using NuGEN Ovation RNA-Seq System", Biotechniques 50(3):177-181 (2011).
Hoeijmakers et al., "Linear amplification for deep sequencing", Nature Protocols 6(7):1026-1036 (2011).
Hoon et al., "Aptamer selection by high-throughput sequencing and informatic analysis", Biotechniques 51(6):413-416 (2011).
Hopmans et al., "A programmable method for massively parallel targeted sequencing", Nucleic Acids Research 42(10):e88 (2014).
Ji et al., "Data quality in genomics and microarrays", Nat Biotechnol. 24(9):1112-1113 (2006).
Ji et al., "Identification of a novel deletion mutant strain in *Saccharomyces cerevisiae* that results in a microsatellite instability phenotype", Biodiscovery 1:4 (2012).
Ji et al., "Molecular Inversion Probe Analysis of Gene Copy Alterations Reveals Distinct Categories of Colorectal Carcinoma", Cancer Res. 66(16):7910-7919 (2006).
Ji et al., "Molecular inversion probe assay for allelic quantitation", Methods Mol Biol. 556:67-87 (2009).
Ji, "Improving bioinformatic pipelines for exome variant calling", Genome Medicine 4(1):7 (2012).
Kinde et al., "Detection and quantification of rare mutations with massively parallel sequencing", PNAS 108(23):9530-95355 (2011).
Kurn et al., "Novel Isothermal, Linear Nucleic Acid Amplification Systems for Highly Multiplexed Applications", Clinical Chemistry 51(10):1973-1981 (2005).
Lam et al., "Performance comparison of whole-genome sequencing platforms." Nat Biotechnol. 30(1):78-82 (2011).
Lee et al., "Systematic genomic identification of colorectal cancer genes delineating advanced from early clinical stage and metastasis", BMC Medical Genomics 6:54 (2013).
Lin et al., "Reproducibility Probability Score—incorporating measurement variability across laboratories for gene selection", Nature Biotechnology 24(12):1476-1477 (2006).
Lishanski et al., "Branch migration inhibition in PCR-amplified DNA: homogeneous mutation detection", Nucleic Acids Research 28(9):e42 (2000).
Liu et al., "High-efficiency thermal asymmetric interlaced PCR for amplification of unknown flanking sequences." Biotechniques Rapid Dispatches 43(5):649-656 (2007).
MAQC Consortium, "The MicroArray Quality Control (MAQC) project shows inter- and intraplatform reproducibility of gene expression measurements", Nat Biotechnol. 24(9):1151-1161 (2006).
Miotke et al., "Correction to High Sensitivity Detection and Quantitation of DNA Copy Number and Single Nucleotide Variants with Single Color Droplet Digital PCR", Anal. Chem. 87:3114 (2015).
Miotke et al., "High Sensitivity Detection and Quantitation of DNA Copy Number and Single Nucleotide Variants with Single Color Droplet Digital PCR", Anal. Chem.86(5):2618-2624 (2014).
Mugasa et al., "Nucleic Acid Sequence-Based Amplification with Oligochromatography for Detection of Trypanosoma brucei in Clinical Samples", Journal of Clinical Microbiology 47(3):630-635 (2009).
Muralidharan et al., "A cross-sample statistical model for SNP detection in short-read sequencing data", Nucleic Acids Research 40(1):e5 (2012).
Myllykangas et al., "Classification of human cancers based on DNA copy number amplification modeling", BMC Medical Genomics 1:15 (2008).
Myllykangas et al., "DNA copy number amplification profiling of human neoplasms", Oncogene 25(55):7324-7332 (2006).
Myllykangas et al., "Integrated gene copy number and expression microarray analysis of gastric cancer highlights potential target genes", Int. J. Cancer 123(4):817-825 (2008).
Myllykangas et al., "Manifestation, mechanisms and mysteries of gene amplifications", Cancer Letters 232 (1):79-89 (2006).
Myllykangas et al., "Novel high-throughput sequencing strategies in genetic diagnostics." Duodecim. 129(2):141-148 (2013). English Abstract [Review Finnish].
Myllykangas et al., "Specificity, selection and significance of gene amplifications in cancer", Seminars in Cancer Biology 17(1):42-55 (2007).
Myllykangas et al., "Targeted deep resequencing of the human cancer genome using next-generation technologies", Biotechnol Genet Eng Rev. 27:135-158 (2010).
Myllykangas et al., "Targeted sequencing library preparation by genomic DNA circularization", BMC Biotechnology 11:122 (2011).
Nadauld et al., "Quantitative and Sensitive Detection of Cancer Genome Amplifications from Formalin Fixed Paraffin Embedded Tumors with Droplet Digital PCR", Transl Med (Sunnyvale) 2(2) (2012).
Natsoulis et al., "A Flexible Approach for Highly Multiplexed Candidate Gene Targeted Resequencing", PLoS One. 6(6):e21088 (2011).

\* cited by examiner

SLC34A2 Exon 13  ROS1  ALTERNATIVE SPLICING

AGGATGTCCCTGTCAAGGCTCCTGAGACCTTTGATAACATAACCATTAGCAGAGAGAGGCTCAGGCTGGAGTCCCAGGCATTCCCAAATTACTAGA  } Exon 32
TCAAGGCTCCTGAGACCTTTGATAACATAACCATTAGCAGAGAGAGGCTCAGGCTGGAGTCCCAGGCATTCCCAAATCAAACAGGCATTCCCAAATTACTAGA
GAGACCTTTGATAACATAACCATTAGCAGAGAGAGGCTCAGGCTGGAGTCCCAGGCATTCCCAAATAAACAGGCATTCCCAAATTACTAGA
GTCCCTGTCAAGGCTCCTGAGACCTTTGATAACATAACCATTAGCAGAGAGAGGCTCAGGCTGGAGTCCCAGGCATTCCCAAATAAACCAGGCATTCCCAAATTACTAGA GCAAGGATGTCCCTGTCAAGGCTCCTGAGACCTTTGATAACATAACCATTAGCAGAGAGAGGCTCAGGCTCAGGATGATTTTTGGATACCAGAGAAACAAGTTTCATACTTACTA  } Exon 34
GGCGCAGGAGGGGCAGGATGTCCCTGTCCCTGTCAAGGCTCTCAAGGCTCCTGTCAAGGCTCCTGAGACCTTTGATAACATAACCATTAGCAGAGAGAGGCTCAGGATGATGATTTTTGGATACCAGAGAAACAAGTTTCATACTTACTA

*FIG. 4B*

```
> SAMPLE_03
  FREQ    FUSION
  164     SLC34A2+Ex13.f2 -- ROS1 - Ex32.f1
  103     SLC34A2+Ex13.f2 -- ROS1 - Ex34.f1
> SAMPLE_15
  FREQ    FUSION
  41      EZR+Ex10.f2--ROS1-Ex34.f1
  8       EZR+Ex10.f2--ROS1-Ex35.f1
```

*FIG. 4C*

SEQUENCE LISTING

<160> NUMBER OF SEQ ID NOS: 60

<210> SEQ ID NO 1
<211> LENGTH: 6267
<212> TYPE: DNA
<213> ORGANISM: Homo sapiens

<400> SEQUENCE: 1

```
agctgcaagt ggcgggcgcc caggcagatg cgatccagcg gctctggggg cggcagcggt      60
ggtagcagct ggtacctccc gccgcctctg ttcggagggt cgcggggcac cgaggtgctt     120
tccggccgcc ctctggtcgg ccacccaaag ccgcgggcgc tgatgatggg tgaggagggg     180
gcggcaagat tcgggcgcc cctgccctga acgccctcag ctgctgccgc cggggccgct     240
ccagtgcctg cgaactctga ggagccgagg cgccggtgag agcaaggacg ctgcaaactt     300
gcgcagcgcg ggggctggga ttcacgccca gaagttcagc aggcagacag tccgaagcct     360
tcccgcagcg gagagatagc ttgagggtgc gcaagacggc agcctccgcc ctcggttccc     420
gcccagaccg ggcagaagag cttggaggag ccaaaaggaa cgcaaaaggc ggccaggaca     480
gcgtgcagca gctgggagcc gccgttctca gccttaaaag ttgcagagat tggaggctgc     540
cccgagaggg gacagacccc agctccgact gcggggggca ggagaggacg gtacccaact     600
gccacctccc ttcaaccata gtagttcctc tgtaccgagc gcagcgagct acagacgggg     660
gcgcggcact cggcgcggag agcgggaggc tcaaggtccc agccagtgag cccagtgtgc     720
ttgagtgtct ctggactcgc ccctgagctt ccaggtctgt ttcatttaga ctcctgctcg     780
cctccgtgca gttgggggaa agcaagagac ttgcgcgcac gcacagtcct ctggagatca     840
```

```
ggtggaagga gccgctgggt accaaggact gttcagagcc tcttcccatc tcggggagag   900
cgaagggtga ggctgggccc ggagagcagt gtaaacggcc tcctccggcg ggatgggagc   960
catcgggctc ctgtggctcc tgccgctgct gctttccacg gcagctgtgg gctccgggat  1020
ggggaccggc cagcgcgcgg gctcccagc tgcggggccg ccgctgcagc cccgggagcc   1080
actcagctac tcgcgcctgc agaggaagag tctggcagtt gacttcgtgg tgccctcgct  1140
cttccgtgtc tacgcccggg acctactgct gccaccatcc tcctcggagc tgaaggctgg  1200
caggcccgag gcccgcggct cgctagctct ggactgcgcc ccgctgctca ggttgctggg  1260
gccggcgccg ggggtctcct ggaccgccgg ttcaccagcc ccggcagagg cccggacgct  1320
gtccagggtg ctgaagggcg gctccgtgcg caagctccgg cgtgccaagc agttggtgct  1380
ggagctgggc gaggaggcga tcttggaggg ttgcgtcggg cccccgggg aggcggctgt   1440
ggggctgctc cagttcaatc tcagcgagct gttcagttgg tggattcgcc aaggcgaagg  1500
gcgactgagg atccgcctga tgcccgagaa aaggcgtcg gaagtgggca gagagggaag   1560
gctgtccgcg gcaattcgcg cctcccagcc ccgccttctc ttccagatct tcgggactgg  1620
tcatagctcc ttggaatcac caacaaacat gccttctcct tctcctgatt attttacatg  1680
gaatctcacc tggataatga aagactcctt ccctttcctg tctcatcgca gccgatatgg  1740
tctggagtgc agctttgact tcccctgtga gctggagtat tcccctccac tgcatgacct  1800
caggaaccag agctggtcct ggcgccgcat ccctccgag gaggcctccc agatggactt   1860
gctggatggg cctggggcag agcgttctaa ggagatgccc agaggctcct ttctccttct  1920
caacacctca gctgactcca agcacaccat cctgagtccg tggatgagga gcagcagtga  1980
gcactgcaca ctggccgtct cggtgcacag gcacctgcag ccctctggaa ggtacattgc  2040
ccagctgctg ccccacaacg aggctgcaag agagatcctc ctgatgccca ctccagggaa  2100
gcatggttgg acagtgctcc agggaagaat cgggcgtcca gacaacccat ttcgagtggc  2160
cctggaatac atctccagtg aaaccgcag cttgtctgca gtggacttct ttgccctgaa  2220
gaactgcagt gaaggaacat ccccaggctc aagatggcc ctgcagagct ccttcacttg   2280
ttggaatggg acagtcctcc agcttgggca ggcctgtgac ttccaccagg actgtgccca  2340
gggagaagat gagagccaga tgtgccggaa actgcctgtg ggtttttact gcaactttga  2400
agatggcttc tgtggctgga cccaaggcac actgtcaccc cacactcctc aatggcaggt  2460
caggacccta aaggatgccc ggttccagga ccaccaagac catgctctat tgctcagtac  2520
cactgatgtc cccgcttctg aaagtgctac agtgaccagt gctacgtttc ctgcaccgat  2580
caagagctct ccatgtgagc tccgaatgtc ctggctcatt cgtggagtct tgaggggaaa  2640
cgtgtccttg gtgctagtgg agaacaaaac cgggaaggag caaggcagga tggtctggca  2700
tgtcgccgcc tatgaaggct tgagcctgtg gcagtggatg tgttgcctc tcctcgatgt   2760
gtctgacagg ttctggctgc agatggtcgc atggtgggga caaggatcca gagccatcgt  2820
ggcttttgac aatatctcca tcagcctgga ctgctacctc accattagcg agaggacaa   2880
gatcctgcag aatacagcac ccaaatcaag aaacctgttt gagagaaacc caaacaagga  2940
gctgaaaccc gggaaaaatt caccaagaca gaccccatc tttgaccct cagttcattg    3000
gctgttcacc acatgtgggg ccagcgggcc ccatggcccc acccaggcac agtgcaacaa  3060
cgcctaccag aactccaacc tgagcgtgga ggtggggagc gagggccccc tgaaaggcat  3120
ccagatctga aaggtgccag ccaccgacac ctacagcatc tcgggctacg agctgctgg   3180
cgggaaaggc gggaagaaca ccatgatgcg gtcccacggc gtgtctgtgc tgggcatctt  3240
```

```
caacctggag aaggatgaca tgctgtacat cctggttggg cagcagggag aggacgcctg   3300 cccccagtaca aaccagttaa tccagaaagt ctgcattgga gagaacaatg tgatagaaga   3360
agaaatccgt gtgaacagaa gcgtgcatga gtgggcagga ggcggaggag gaggggtgg    3420 agccacctac gtatttaaga tgaaggatgg agtgccggtg cccctgatca ttgcagccgg   3480
aggtggtggc agggcctacg gggccaagac agacacgttc cacccagaga gactggagaa   3540
taactcctcg gttctagggc taaacggcaa ttccggagcc gcaggtggtg gaggtggctg   3600
gaatgataac acttccttgc tctgggccgg aaaatctttg caggagggtg ccaccggagg   3660
acattcctgc ccccaggcca tgaagaagtg ggggtgggag acaagagggg gtttcggagg   3720
gggtggaggg gggtgctcct caggtggagg aggcggagga tatataggcg gcaatgcagc   3780
ctcaaacaat gaccccgaaa tggatgggga agatgggggtt ccttcatca gtccactggg   3840 catcctgtac accccagctt taaaagtgat ggaaggccac ggggaagtga atattaagca   3900
ttatctaaac tgcagtcact gtgaggtaga cgaatgtcac atggaccctg aaagccacaa   3960
ggtcatctgc ttctgtgacc acgggacggt gctggctgag gatggcgtct cctgcattgt   4020
gtcacccacc ccggagccac acctgccact ctcgctgatc ctctctgtgg tgacctctgc   4080
cctcgtggcc gccctggtcc tggctttctc cggcatcatg attgtgtacc gccggaagca   4140
ccaggagctg caagccatgc agatggagct gcagagccct gagtacaagc tgagcaagct   4200
ccgcacctcg accatcatga ccgactacaa ccccaactac tgctttgctg gcaagacctc   4260
ctccatcagt gacctgaagg aggtgccgcg gaaaaacatc ccctcattc ggggtctggg   4320 ccatggcgcc tttggggagg tgtatgaagg ccaggtgtcc ggaatgccca acgacccaag   4380
ccccctgcaa gtggctgtga agacgctgcc tgaagtgtgc tctgaacagg acgaactgga   4440
tttcctcatg gaagccctga tcatcagcaa attcaaccac cagaacattg ttcgctgcat   4500 tgggggtgagc ctgcaatccc tgccccggtt catcctgctg gagctcatgg cggggggaga   4560
cctcaagtcc ttcctccgag agacccgccc tcgcccgagc cagccctcct ccctggccat   4620
gctggacctt ctgcacgtgg ctcgggacat tgcctgtggc tgtcagtatt tggaggaaaa   4680
ccacttcatc caccgagaca ttgctgccag aaactgcctc ttgacctgtc caggccctgg   4740
aagagtggcc aagattggag acttcgggat ggcccgagac atctacaggg cgagctacta   4800
tagaaaggga ggctgtgcca tgctgccagt taagtggatg ccccccagagg ccttcatgga   4860 aggaatattc acttctaaaa cagacacatg gtcctttgga gtgctgctat gggaaatctt   4920
ttctcttgga tatatgccat accccagcaa agcaaccag gaagttctgg agtttgtcac   4980
cagtggaggc cggatggacc acccaagaa ctgccctggg cctgtatacc ggataatgac   5040
tcagtgctgg caacatcagc ctgaagacag gcccaactttt gccatcattt tggagaggat   5100
tgaatactgc acccaggacc cggatgtaat caacaccgct ttgccgatag aatatggtcc   5160
acttgtggaa gaggaagaga aagtgcctgt gaggcccaag gacctgagg gggttcctcc   5220 tctcctggtc tctcaacagg caaaacggga ggaggagcgc agcccagctg ccccaccacc   5280
tctgcctacc acctcctctg gcaaggctgc aaagaaaccc acagctgcag agatctctgt   5340
tcgagtccct agagggccgg ccgtggaagg gggacacgtg aatatggcat tctctcagtc   5400
caaccctcct tcggagttgc acaaggtcca cggatccaga aacaagccca ccagcttgtg   5460
gaacccaacg tacggctcct ggtttacaga gaaacccacc aaaaagaata atcctatagc   5520
aaagaaggag ccacacgaca ggggtaacct ggggctggag ggaagctgta ctgtcccacc   5580
```

-continued

```
taacgttgca actgggagac ttccgggggc ctcactgctc ctagagccct cttcgctgac    5640
tgccaatatg aaggaggtac ctctgttcag gctacgtcac ttcccttgtg ggaatgtcaa    5700
ttacggctac cagcaacagg gcttgccctt agaagccgct actgccctg gagctggtca     5760 ttacgaggat accattctga aaagcaagaa tagcatgaac cagcctgggc cctgagctcg    5820
gtcgcacact cacttctctt ccttgggatc cctaagaccg tggaggagag agaggcaatg    5880
gctccttcac aaaccagaga ccaaatgtca cgttttgttt tgtgccaacc tattttgaag    5940
taccaccaaa aaagctgtat tttgaaaatg ctttagaaag gttttgagca tgggttcatc    6000
ctattctttc gaaagaagaa aatatcataa aaatgagtga taaatacaag gcccagatgt    6060
ggttgcataa ggttttatg catgtttgtt gtatacttcc ttatgcttct ttcaaattgt     6120
gtgtgctctg cttcaatgta gtcagaatta gctgcttcta tgtttcatag ttggggtcat    6180
agatgtttcc ttgccttgtt gatgtggaca tgagccattt gaggggagag ggaacggaaa    6240
taaaggagtt atttgtaatg actaaaa                                        6267
```

<210> SEQ ID NO 2
<211> LENGTH: 7368
<212> TYPE: DNA
<213> ORGANISM: Homo sapiens

<400> SEQUENCE: 2

```
caagctttca agcattcaaa ggtctaaatg aaaaaggcta agtattattt caaaaggcaa      60
gtatatccta atatagcaaa acaaacaaag caaaatccat cagctactcc tccaattgaa     120
gtgatgaagc ccaaataatt catatagcaa aatggagaaa attagaccgg ccatctaaaa     180
atctgccatt ggtgaagtga tgaagaacat ttactgtctt attccgaagc ttgtcaattt     240
tgcaactctt ggctgcctat ggatttctgt ggtgcagtgt acagttttaa atagctgcct     300
aaagtcgtgt gtaactaatc tgggccagca gcttgacctt ggcacaccac ataatctgag     360
tgaaccgtgt atccaaggat gtcacttttg gaactctgta gatcagaaaa actgtgcttt     420
aaagtgtcgg gagtcgtgtg aggttggctg tagcagcgcg gaaggtgcat atgaagagga     480
agtactggaa aatgcagacc taccaactgc tccctttgct tcttccattg gaagccacaa     540
tatgacatta cgatggaaat ctgcaaactt ctctggagta aaatacatca ttcagtggaa     600
atatgcacaa cttctgggaa gctggactta ctactaagact gtgtccagac cgtcctatgt    660
ggtcaagccc ctgcaccct tcactgagta cattttccga gtggtttgga tcttcacagc      720
gcagctgcag ctctactccc ctccaagtcc cagttacagg actcatcctc atggagttcc     780
tgaaactgca ccttttgatta ggaatattga gagctcaagt cccgacactg tggaagtcag    840
ctgggatcca cctcaattcc caggtggacc tattttgggt tataacttaa ggctgatcag     900
caaaaatcaa aaattagatg cagggacaca gagaaccagt ttccagttttt actccacttt    960 accaaatact atctacaggt tttctattgc agcagtaaat gaagttggtg agggtccaga    1020
agcagaatct agtattacca cttcatcttc agcagttcaa caagaggaac agtggctctt   1080
tttatccaga aaaacttctc taagaaagag atctttaaaa catttagtag atgaagcaca   1140
ttgccttcgg ttggatgcta tataccataa tattacagga atatctgttg atgtccacca   1200
gcaaattgtt tatttctctg aaggaactct catatgggcg aagaaggctg ccaacatgtc   1260
tgatgtatct gacctgagaa ttttttacag aggttcagga ttaatttctt ctatctccat   1320
agattggctt tatcaaagaa tgtatttcat catggatgaa ctggtatgtg tctgtgatttt   1380 agagaactgc tcaaacatcg aggaaattac tccacccctct attagtgcac ctcaaaaaat  1440
```

```
tgtggctgat tcatacaatg ggtatgtctt ttacctcctg agagatggca tttatagagc    1500
agaccttcct gtaccatctg gccggtgtgc agaagctgtg cgtattgtgg agagttgcac    1560
gttaaaggac tttgcaatca agccacaagc caagcgaatc atttacttca atgacactgc    1620
ccaagtcttc atgtcaacat ttctggatgg ctctgcttcc catctcatcc tacctcgcat    1680
cccctttgct gatgtgaaaa gttttgcttg tgaaaacaat gactttcttg tcacagatgg    1740
caaggtcatt ttccaacagg atgctttgtc ttttaatgaa ttcatcgtgg gatgtgacct    1800
gagtcacata gaagaatttg ggtttggtaa cttggtcatc tttggctcat cctcccagct    1860
gcaccctctg ccaggccgcc cgcaggagct ttcggtgctg tttggctctc accaggctct    1920
tgttcaatgg aagcctcctg cccttgccat aggagccaat gtcatcctga tcagtgatat    1980
tattgaactc tttgaattag gcccttctgc ctggcagaac tggacctatg aggtgaaagt    2040
atccacccaa gaccctcctg aagtcactca tattttcttg aacataagtg gaaccatgct    2100
gaatgtacct gagctgcaga gtgctatgaa atacaaggtt tctgtgagag caagttctcc    2160
aaagaggcca ggcccctggt cagagccctc agtgggtact accctggtgc cagctagtga    2220
accaccattt atcatggctg tgaaagaaga tgggctttgg agtaaaccat taaatagctt    2280
tggcccagga gagttcttat cctctgatat aggaaatgtg tcagacatgg attggtataa    2340
caacagcctc tactacagtg cacgaaaggc gacgtttttt gtgtggctgc tgaatgggac    2400
ggatatctca gagaattatc acctacccag cattgcagga gcaggggctt tagcttttga    2460
gtggctgggt cactttctct actgggctgg aaagacatat gtgatacaaa ggcagtctgt    2520
gttgacggga cacacagaca ttgttaccca cgtgaagcta ttggtgaatg acatggtggt    2580
ggattcagtt ggtggatatc tctactggac cacactctat tcagtggaaa gcaccagact    2640
aaatggggaa agttcccttg tactacagac acagccttgg ttttctggga aaaaggtaat    2700
tgctctaact ttagacctca gtgatgggct cctgtattgg ttggttcaag acagtcaatg    2760
tattcacctg tacacagctg ttcttcgggg acagagcact ggggatacca ccatcacaga    2820
atttgcagcc tggagtactt ctgaaatttc ccagaatgca ctgatgtact atagtggtcg    2880
gctgttctgg atcaatggct ttaggattat cacaactcaa gaaataggtc agaaaaccag    2940
tgtctctgtt ttggaaccag ccagatttaa tcagttcaca attattcaga catcccttaa    3000
gcccctgcca gggaacttttt cctttacccc taaggttatt ccagattctg ttcaagagtc    3060
ttcatttagg attgaaggaa atgcttcaag ttttcaaatc ctgtggaatg gtccccctgc    3120
ggtagactgg ggtgtagttt tctacagtgt agaatttagt gctcattcta agttcttggc    3180
tagtgaacaa cactctttac ctgtatttac tgtggaagga ctggaacctt atgccttatt    3240
taatctttct gtcactcctt ataccactg ggaaagggc cccaaaacat ctctgtcact    3300
tcgagcacct gaaacagttc catcagcacc agagaacccc agaatattta tattaccaag    3360
tggaaaatgc tgcaacaaga atgaagttgt ggtggaattt aggtgaaca aacctaagca    3420 tgaaaatggg gtgttaacaa aatttgaaat tttctacaat atatccaatc aaagtattac    3480
aaacaaaaca tgtgaagact ggattgctgt caatgtcact ccctcagtga tgtcttttca    3540
acttgaaggc atgagtccca gatgctttat tgccttccag gttagggcct ttacatctaa    3600
ggggccagga ccatatgctg acgttgtaaa gtctacaaca tcagaaatca acccatttcc    3660
tcacctcata actcttcttg gtaacaagat agtttttta gatatggatc aaaatcaagt    3720
tgtgtggacg ttttcagcag aaagagttat cagtgccgtt tgctacacag ctgataatga    3780
```

-continued

```
gatgggatat tatgctgaag gggactcact ctttcttctg cacttgcaca atcgctctag    3840
ctctgagctt ttccaagatt cactggtttt tgatatcaca gttattacaa ttgactggat    3900
ttcaaggcac ctctactttg cactgaaaga atcacaaaat ggaatgcaag tatttgatgt    3960
tgatcttgaa cacaaggtga aatatcccag agaggtgaag attcacaata ggaattcaac    4020
aataatttct ttttctgtat atcctctttt aagtcgcttg tattggacag aagtttccaa    4080
ttttggctac cagatgttct actacagtat tatcagtcac accttgcacc gaattctgca    4140
acccacagct acaaccaac aaaacaaaag gaatcaatgt tcttgtaatg tgactgaatt    4200
tgagttaagt ggagcaatgg ctattgatac ctctaaccta gagaaaccat tgatatactt    4260
tgccaaagca caagagatct gggcaatgga tctggaaggc tgtcagtgtt ggagagttat    4320
cacagtacct gctatgctcg caggaaaaac ccttgttagc ttaactgtgg atggagatct    4380
tatatactgg atcatcacag caaaggacag cacacagatt tatcaggcaa agaaaggaaa    4440
tggggccatc gtttcccagg tgaaggccct aaggagtagg catatcttgg cttacagttc    4500
agttatgcag cctttccag ataaagcgtt tctgtctcta gcttcagaca ctgtggaacc    4560
aactatactt aatgccacta acactagcct cacaatcaga ttacctctgg ccaagacaaa    4620
cctcacatgg tatggcatca ccagccctac tccaacatac ctggtttatt atgcagaagt    4680
taatgacagg aaaacagct ctgacttgaa atatagaatt ctggaatttc aggacagtat    4740
agctcttatt gaagatttac aaccattttc aacatacatg atacagatag ctgtaaaaaa    4800
ttattattca gatcctttgg aacatttacc accaggaaaa gagatttggg gaaaaactaa    4860
aaatggagta ccagaggcag tgcagctcat taatacaact gtgcggtcag acaccagcct    4920
cattatatct tggagagaat ctcacaagcc aaatggacct aaagaatcag tccgttatca    4980
gttggcaatc tcacacctgg ccctaattcc tgaaactcct ctaagacaaa gtgaatttcc    5040
aaatggaagg ctcactctcc ttgttactag actgtctggt ggaaatattt atgtgttaaa    5100
ggttcttgcc tgccactctg aggaaatgtg gtgtacagag agtcatcctg tcactgtgga    5160
aatgtttaac acaccagaga aaccttattc cttggttcca gagaacacta gtttgcaatt    5220
taattggaag gctccattga atgttaacct catcagattt tgggttgagc tacagaagtg    5280
gaaatacaat gagttttacc atgttaaaac ttcatgcagc caaggtcctg cttatgtctg    5340
taatatcaca aatctacaac cttatacttc atataatgtc agagtagtgg tggtttataa    5400
gacgggagaa aatagcacct cacttccaga aagctttaag acaaaagctg gagtcccaaa    5460
taaaccaggc attcccaaat tactagaagg gagtaaaaat tcaatacagt gggagaaagc    5520
tgaagataat ggatgtagaa ttacatacta tatccttgag ataagaaaga gcacttcaaa    5580
taatttacag aaccagaatt taaggtggaa gatgacattt aatggatcct gcagtagtgt    5640
ttgcacatgg aagtccaaaa acctgaaagg aatatttcag ttcagagtag tagctgcaaa    5700
taatctaggg tttggtgaat atagtggaat cagtgagaat attatattag ttggagatga    5760 ttttttggata ccagaaacaa gtttcatact tactattata gttggaatat ttctggttgt    5820
tacaatccca ctgacctttg tctggcatag aagattaaag aatcaaaaaa gtgccaagga    5880 agggtgaca gtgcttataa acgaagacaa agagttggct gagctgcgag gtctggcagc    5940
cggagtaggc ctggctaatg cctgctatgc aatacatact cttccaaccc aagaggagat    6000
tgaaaatctt cctgccttcc ctcgggaaaa actgactctg cgtctcttgc tgggaagtgg    6060
agcctttgga gaagtgtatg aaggaacagc agtggacatc ttaggagttg gaagtggaga    6120
aatcaaagta gcagtgaaga ctttgaagaa gggttccaca gaccaggaga agattgaatt    6180
```

-continued

```
cctgaaggag gcacatctga tgagcaaatt taatcatccc aacattctga agcagcttgg   6240
agtttgtctg ctgaatgaac cccaatacat tatcctggaa ctgatggagg gaggagacct   6300
tcttacttat ttgcgtaaag cccggatggc aacgttttat ggtcctttac tcaccttggt   6360
tgaccttgta gacctgtgtg tagatatttc aaaaggctgt gtctacttgg aacggatgca   6420
tttcattcac agggatctgg cagctagaaa ttgccttgtt tccgtgaaag actataccag   6480
tccacggata gtgaagattg gagactttgg actcgccaga gacatctata aaaatgatta   6540
ctatagaaag agagggaag gcctgctccc agttcggtgg atggctccag aaagtttgat    6600
ggatggaatc ttcactactc aatctgatgt atggtctttt ggaattctga tttgggagat   6660
tttaactctt ggtcatcagc cttatccagc tcattccaac cttgatgtgt taaactatgt   6720
gcaaacagga gggagactgg agccaccaag aaattgtcct gatgatctgt ggaatttaat   6780
gacccagtgc tgggctcaag aacccgacca agacctact  tttcatagaa ttcaggacca   6840
acttcagtta ttcagaaatt ttttcttaaa tagcatttat aagtccagag atgaagcaaa   6900
caacagtgga gtcataaatg aaagctttga aggtgaagat ggcgatgtga tttgtttgaa   6960
ttcagatgac attatgccag ttgctttaat ggaaacgaag aaccgagaag ggttaaacta   7020
tatggtactt gctacagaat gtggccaagg tgaagaaaag tctgagggtc ctctaggctc   7080
ccaggaatct gaatcttgtg gtctgaggaa agaagaag gaaccacatg cagacaaaga    7140
tttctgccaa gaaaaacaag tggcttactg ccccttctgg aagcctgaag gcctgaacta   7200
tgcctgtctc actcacagtg gatatggaga tgggtctgat taatagcgtt gtttgggaaa   7260
tagagagttg agataaacac tctcattcag tagttactga aagaaaactc tgctagaatg   7320
ataaatgtca tggtggtcta taactccaaa taaacaatgc aacgttcc              7368
```

<210> SEQ ID NO 3
<211> LENGTH: 4174
<212> TYPE: DNA
<213> ORGANISM: Homo sapiens

<400> SEQUENCE: 3

```
agtcccgcga ccgaagcagg gcgcgcagca gcgctgagtg ccccggaacg tgcgtcgcgc     60
ccccagtgtc cgtcgcgtcc gccgcgcccc gggcggggat ggggcggcca gactgagcgc    120
cgcacccgcc atccagaccc gccggcccta gccgcagtcc ctccagccgt ggccccagcg    180
cgcacgggcg atggcgaagg cgacgtccgg tgccgcgggg ctgcgtctgc tgttgctgct    240
gctgctgccg ctgctaggca aagtggcatt gggcctctac ttctcgaggg atgcttactg    300
ggagaagctg tatgtggacc aggcggccgg cacgcccttg ctgtacgtcc atgccctgcg    360
ggacgcccct gaggaggtgc ccagcttccg cctgggccag catctctacg cacgtaccg    420 cacacggctg catgagaaca actggatctg catccaggag gacaccggcc tcctctacct    480
taaccggagc ctggaccata gctcctggga agctcagt gtccgcaacc gcggctttcc     540
cctgctcacc gtctacctca aggtcttcct gtcacccaca tcccttcgtg agggcgagtg    600
ccagtggcca ggctgtgccc gcgtatactt ctccttcttc aacacctcct ttccagcctg    660 cagctcccctc aagcccgggg agtctgctt cccagagaca aggccctcct tccgcattcg    720
ggagaaccga cccccaggca ccttccacca gttccgcctg ctgcctgtgc agttcttgtg    780
ccccaacatc agcgtggcct acaggctcct ggagggtgag ggtctgccct tccgctgcgc    840 cccgacagc ctggaggtga gcacgcgctg ggccctggac cgcgagcagc gggagaagta    900
```

```
cgagctggtg gccgtgtgca ccgtgcacgc cggcgcgcgc gaggaggtgg tgatggtgcc    960
cttcccggtg accgtgtacg acgaggacga ctcggcgccc accttccccg cgggcgtcga   1020
caccgccagc gccgtggtgg agttcaagcg gaaggaggac accgtggtgg ccacgctgcg   1080
tgtcttcgat gcagacgtgg tacctgcatc aggggagctg gtgaggcggt acacaagcac   1140
gctgctcccc ggggacacct gggcccagca gaccttccgg gtggaacact ggcccaacga   1200
gacctcggtc caggccaacg gcagcttcgt gcgggcgacc gtacatgact ataggctggt   1260
tctcaaccgg aacctctcca tctcggagaa ccgcaccatg cagctggcgg tgctggtcaa   1320
tgactcagac ttccagggcc caggagcggg cgtcctcttg ctccacttca cgtgtcggt    1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgcccccct  1740
gtcctgtgca gtcagcaaga gacggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgccccga cggccactgc gatgttgtgg agacccaaga   1920
catcaacatt tgccctcagg actgcctccg gggcagcatt gttggggac  acgagcctgg   1980
ggagcccgg gggattaaag ctggctatgg cacctgcaac tgcttccctg aggaggagaa    2040
gtgcttctgc gagcccgaag acatccagga tccactgtgc gacgagctgt ccgcacggt    2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagaaacg  cctccccgag tgagcttcga gacctgctgt cagagttcaa   2520
cgtcctgaag caggtcaacc acccacatgt catcaaattg tatgggggcct gcagccagga  2580
tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag gggatgcagt atctggccga gatgaagctc gttcatcggg acttggcagc   2820
cagaaacatc ctggtagctg agggggcgaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct aggggaaaac ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
gtttgcggac atcagcaaag acctggaaa  gatgatggtt aagaggagag actacttgga   3240
ccttgcggcg tccactccat ctgactccct gatttatgac gacggcctct cagaggagga   3300
```

```
gacaccgctg gtggactgta ataatgcccc cctccctcga gccctccctt ccacatggat    3360
tgaaaacaaa ctctatggta gaatttccca tgcatttact agattctagc accgctgtcc    3420
cctctgcact atccttcctc tctgtgatgc ttttaaaaa tgtttctggt ctgaacaaaa      3480
ccaaagtctg ctctgaacct ttttatttgt aaatgtctga ctttgcatcc agtttacatt    3540
taggcattat tgcaactatg ttttctaaa aggaagtgaa aataagtgta attaccacat      3600
tgcccagcaa cttaggatgg tagaggaaaa aacagatcag ggcggaactc tcaggggaga    3660
ccaagaacag gttgaataag gcgcttctgg ggtgggaatc aagtcatagt acttctactt    3720
taactaagtg gataaatata caaatctggg gaggtattca gttgagaaag gagccaccag    3780
caccactcag cctgcactgg gagcacagcc aggttccccc agaccccttcc tgggcaggca    3840 ggtgcctctc agaggccacc cggcactggc gagcagccac tggccaagcc tcagcccag     3900 tcccagccac atgtcctcca tcaggggtag cgaggttgca ggagctggct ggccctggga    3960
ggacgcaccc ccactgctgt tttcacatcc tttcccttac ccaccttcag gacggttgtc    4020
acttatgaag tcagtgctaa agctggagca gttgcttttt gaaagaacat ggtctgtggt    4080
gctgtggtct tacaatggac agtaaatatg gttcttgcca aaactccttc ttttgtcttt    4140
gattaaatac tagaaattta aaaaaaaaa aaaa                                  4174

<210> SEQ ID NO 4
<211> LENGTH: 5629
<212> TYPE: DNA
<213> ORGANISM: Homo sapiens

<400> SEQUENCE: 4
agtcccgcga ccgaagcagg gcgcgcagca gcgctgagtg ccccggaacg tgcgtcgcgc      60
ccccagtgtc cgtcgcgtcc gccgcgcccc gggcggggat ggggcggcca gactgagcgc    120 cgcaccgcc atccagaccc gccggcccta gccgcagtcc ctccagccgt ggccccagcg     180
cgcacgggcg atggcgaagg cgacgtccgg tgccgcgggg ctgcgtctgc tgttgctgct    240
gctgctgccg ctgctaggca aagtggcatt gggcctctac ttctcgaggg atgcttactg    300
ggagaagctg tatgtggacc aggcggccgg cacgcccttg ctgtacgtcc atgccctgcg    360
ggacgcccct gaggaggtgc ccagcttccg cctgggccag catctctacg gcacgtaccg    420
cacacggctg catgagaaca actggatctg catccaggag gacaccggcc tcctctacct    480
taaccggagc ctggaccata gctcctggga gaagctcagt gtccgcaacc gcggctttcc    540
cctgctcacc gtctacctca aggtcttcct gtcacccaca tcccttcgtg agggcgagtg    600
ccagtggcca ggctgtgccc gcgtatactt ctccttcttc aacacctcct ttccagcctg    660
cagctccctc aagcccgggg agctctgctt cccagagaca aggccctcct tccgcattcg    720
ggagaaccga ccccaggca ccttccacca gttccgcctg ctgcctgtgc agttcttgtg     780
ccccaacatc agcgtggcct acaggctcct ggagggtgag ggtctgccct tccgctgcgc    840
cccggacagc ctggaggtga gcacgcgctg ggccctggac cgcgagcagc gggagaagta    900
cgagctggtg gccgtgtgca ccgtgcacgc cggcgcgcgc gaggaggtgg tgatggtgcc    960
cttcccggtg accgtgtacg acgaggacga ctcggcgccc accttccccg cgggcgtcga   1020
caccgccagc gccgtggtgg agttcaagcg gaaggaggac accgtggtgg ccacgctgcg   1080
tgtcttcgat gcagacgtgg tacctgcatc agggagctg gtgaggcggt acacaagcac     1140
gctgctcccc ggggacacct gggcccagca gaccttccgg gtggaacact ggcccaacga   1200
```

```
gacctcggtc caggccaacg gcagcttcgt gcgggcgacc gtacatgact ataggctggt    1260
tctcaaccgg aacctctcca tctcggagaa ccgcaccatg cagctggcgg tgctggtcaa    1320
tgactcagac ttccagggcc caggagcggg cgtcctcttg ctccacttca acgtgtcggt    1380
gctgccggtc agcctgcacc tgcccagtac ctactccctc tccgtgagca ggagggctcg    1440
ccgatttgcc cagatcggga aagtctgtgt ggaaaactgc caggcattca gtggcatcaa    1500
cgtccagtac aagctgcatt cctctggtgc caactgcagc acgctagggg tggtcacctc    1560
agccgaggac acctcgggga tcctgtttgt gaatgacacc aaggccctgc ggcggcccaa    1620
gtgtgccgaa cttcactaca tggtggtggc caccgaccag cagacctcta ggcaggccca    1680
ggcccagctg cttgtaacag tggaggggtc atatgtggcc gaggaggcgg gctgccccct    1740
gtcctgtgca gtcagcaaga gacgctggag tgtgaggag tgtggcggcc tgggctcccc    1800
aacaggcagg tgtgagtgga ggcaaggaga tggcaaaggg atcaccagga acttctccac    1860
ctgctctccc agcaccaaga cctgcccga cggccactgc gatgttgtgg agacccaaga    1920
catcaacatt tgccctcagg actgcctccg ggcagcatt gttggggac acgagcctgg    1980 ggagccccgg gggattaaag ctggctatgg cacctgcaac tgcttccctg aggaggagaa    2040
gtgcttctgc gagcccgaag acatccagga tccactgtgc gacgagctgt ccgcacggt    2100 gatcgcagcc gctgtcctct tctccttcat cgtctcggtg ctgctgtctg ccttctgcat    2160
ccactgctac cacaagtttg cccacaagcc acccatctcc tcagctgaga tgaccttccg    2220
gaggcccgcc caggccttcc cggtcagcta ctcctcttcc ggtgcccgcc ggccctcgct    2280
ggactccatg gagaaccagg tctccgtgga tgccttcaag atcctggagg atccaaagtg    2340
ggaattccct cggaagaact tggttcttgg aaaaactcta ggagaaggcg aatttggaaa    2400
agtggtcaag gcaacggcct tccatctgaa aggcagagca gggtacacca cggtggccgt    2460
gaagatgctg aaagagaacg cctccccgag tgagcttcga gacctgctgt cagagttcaa    2520
cgtcctgaag caggtcaacc acccacatgt catcaaattg tatgggcct gcagccagga    2580 tggcccgctc ctcctcatcg tggagtacgc caaatacggc tccctgcggg gcttcctccg    2640
cgagagccgc aaagtggggc ctggctacct gggcagtgga ggcagccgca actccagctc    2700
cctggaccac ccgatgagc gggccctcac catgggcgac ctcatctcat ttgcctggca    2760
gatctcacag gggatgcagt atctggccga gatgaagctc gttcatcggg acttggcagc    2820
cagaaacatc ctggtagctg aggggcggaa gatgaagatt tcggatttcg gcttgtcccg    2880
agatgtttat gaagaggatt cctacgtgaa gaggagccag ggtcggattc cagttaaatg    2940
gatggcaatt gaatcccttt ttgatcatat ctacaccacg caaagtgatg tatggtcttt    3000
tggtgtcctg ctgtgggaga tcgtgacccct agggggaaac ccctatcctg ggattcctcc    3060
tgagcggctc ttcaaccttc tgaagaccgg ccaccggatg gagaggccag acaactgcag    3120
cgaggagatg taccgcctga tgctgcaatg ctggaagcag gagccggaca aaaggccggt    3180
gtttgcggac atcagcaaag acctggagaa gatgatggtt aagaggagag actacttgga    3240
ccttgcggcg tccactccat ctgactccct gatttatgac gacggcctct cagaggagga    3300
gacaccgctg gtggactgta ataatgcccc cctcccctcga gccctccctt ccacatggat    3360
tgaaaacaaa ctctatggca tgtcagaccc gaactggcct ggagagagtc ctgtaccact    3420
cacgagagct gatggcacta acactggggtt tccaagatat ccaaatgata gtgtatatgc    3480
taactggatg ctttcacccct cagcggcaaa attaatggac acgtttgata gttaacattt    3540
ctttgtgaaa ggtaatggac tcacaagggg aagaaacatg ctgagaatgg aaagtctacc    3600
```

-continued

```
ggcccttttct tgtgaacgt cacattggcc gagccgtgtt cagttccag gtggcagact   3660 cgttttggt agtttgtttt aacttccaag gtggttttac ttctgatagc cggtgatttt    3720
ccctcctagc agacatgcca caccgggtaa gagctctgag tcttagtggt taagcattcc    3780
tttctcttca gtgcccagca gcacccagtg ttggtctgtg tccatcagtg accaccaaca    3840
ttctgtgttc acatgtgtgg gtccaacact tactacctgg tgtatgaaat tggacctgaa    3900
ctgttggatt tttctagttg ccgccaaaca aggcaaaaaa atttaaacat gaagcacaca    3960
cacaaaaaag gcagtaggaa aaatgctggc cctgatgacc tgtccttatt cagaatgaga    4020
gactgcgggg ggggcctggg ggtagtgtca atgcccctcc agggctggag gggaagaggg    4080
gccccgagga tgggcctggg ctcagcattc gagatcttga gaatgatttt ttttttaatca   4140 tgcaaccttt ccttaggaag acatttggtt ttcatcatga ttaagatgat tcctagatttt    4200 agcacaatgg agagattcca tgccatcttt actatgtgga tggtggtatc agggaagagg    4260
gctcacaaga cacatttgtc ccccgggccc accacatcat cctcacgtgt tcggtactga    4320
gcagccacta cccctgatga gaacagtatg aagaaggggg gctgttggag tcccagaatt    4380
gctgacagca gaggctttgc tgctgtgaat cccacctgcc accagcctgc agcacacccc    4440
acagccaagt agaggcgaaa gcagtggctc atcctacctg ttaggagcag gtagggcttg    4500
tactcacttt aatttgaatc ttatcaactt actcataaag ggacaggcta gctagctgtg    4560
ttagaagtag caatgacaat gaccaaggac tgctacacct ctgattacaa ttctgatgtg    4620
aaaaagatgg tgtttggctc ttatagagcc tgtgtgaaag gcccatggat cagctcttcc    4680
tgtgtttgta atttaatgct gctacaagat gtttctgttt cttagattct gaccatgact    4740
cataagcttc ttgtcattct tcattgcttg tttgtggtca cagatgcaca acactcctcc    4800
agtcttgtgg gggcagcttt tgggaagtct cagcagctct tctggctgtg ttgtcagcac    4860
tgtaacttcg cagaaaagag tcggattacc aaaacactgc ctgctcttca gacttaaagc    4920
actgatagga cttaaaatag tctcattcaa atactgtatt ttatataggc atttcacaaa    4980
aacagcaaaa ttgtggcatt ttgtgaggcc aaggcttgga tgcgtgtgta atagagcctt    5040
gtggtgtgtg cgcacacacc cagagggaga gtttgaaaaa tgcttattgg acacgtaacc    5100
tggctctaat ttgggctgtt tttcagatac actgtgataa gttcttttac aaatatctat    5160
agacatggta aacttttggt tttcagatat gcttaatgat agtcttacta aatgcagaaa    5220
taagaataaa ctttctcaaa ttattaaaaa tgcctacaca gtaagtgtga attgctgcaa    5280
caggtttgtt ctcaggaggg taagaactcc aggtctaaac agctgaccca gtgatgggga    5340
atttatcctt gaccaattta tccttgacca ataacctaat tgtctattcc tgagttataa    5400
aagtccccat ccttattagc tctactggaa ttttcataca cgtaaatgca gaagttacta    5460
agtattaagt attactgagt attaagtagt aatctgtcag ttattaaaat ttgtaaaatc    5520
tatttatgaa aggtcattaa accagatcat gttcctttt ttgtaatcaa ggtgactaag    5580
aaaatcagtt gtgtaaataa aatcatgtat cataaaaaaa aaaaaaaa                 5629
```

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cctctctatg ggcagtcggt gatgcgagag tggcaggtgt gg          42

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatctcgac gctctccctc agaggtcacc acagagagga tcag        44

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctctctatg ggcagtcggt gatcatggct tgcagctcct ggt         43

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatctcgac gctctccctg cagctccatc tgcatggctt g           41

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctctctatg ggcagtcggt gatggccttc atacacctcc ccaaa       45

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatctcgac gctctccctt tgggcattcc ggacacc                37

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
cctctctatg ggcagtcggt gataggaaat ccagttcgtc ctgttcaga          49
```

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12

```
ggatctcgac gctctccctg atcagggctt ccatgaggaa atc                43
```

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13

```
cctctctatg ggcagtcggt gatggctccc caggctcgtg t                  41
```

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14

```
ggatctcgac gctctcccta ggtgccatag ccagctttaa tcc                43
```

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 15

```
cctctctatg ggcagtcggt gatatcaccg tgcggcacag ctc                43
```

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 16

```
ggatctcgac gctctccctg aggacagcgg ctgcgatca                     39
```

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 17

```
cctctctatg ggcagtcggt gatagaacca agttcttccg agggaat            47
```

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatctcgac gctctcccctt ccaaattcgc cttctcctag agtt                      44

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctctctatg ggcagtcggt gatacagcag gtctcgcagc tcac                       44

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatctcgac gctctcccctt gacctgcttc aggacgttga a                         41

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctctctatg ggcagtcggt gatcttgctg actgcacagg acagg                      45

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggatctcgac gctctcccctt cctcacactc cagccgtctc                           40

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctctctatg ggcagtcggt gattggtgct gggagagcag gt                         42

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatctcgac gctctccctc cgtcggggca ggtcttg                                37

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctctctatg ggcagtcggt gatggctgca tgaagtttta acatgg                      46

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggatctcgac gctctcccdt gatattacag acataagcag gaccttgg                    48

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctctctatg ggcagtcggt gatctagtaa tttgggaatg cctggttt                    48

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggatctcgac gctctccctt tcagctttct cccactgtat tgaa                        44

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cctctctatg ggcagtcggt gatcatcttc caccttaaat tctggttctg ta               52

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ggatctcgac gctctccctc aggatccatt aaatgtcatc ttcc            44

<210> SEQ ID NO 31
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
cctctctatg ggcagtcggt gatagtaagt atgaaacttg tttctggtat cc            52

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ggatctcgac gctctccctg gtcagtggga ttgtaacaac cag            43

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cctctctatg ggcagtcggt gatcacccct tccttggcac ttt            43

<210> SEQ ID NO 34
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ggatctcgac gctctccctt ctttgtcttc gtttataagc actgtc            46

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cctctctatg ggcagtcggt gatttcaatc tcctcttggg ttgga            45

<210> SEQ ID NO 36

```
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggatctcgac gctctccctc cgagggaagg caggaagatt                            40

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctctctatg ggcagtcggt gatcaggaat tcaatcttct cctggtc                    47

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggatctcgac gctctccctc tcatcagatg tgcctccttc ag                         42

<210> SEQ ID NO 39
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aggatgtccc tgtcaaggct cctgagacct tgataacat aaccattagc agagaggctc      60
aggctggagt cccaaataaa ccaggcattc ccaaattact aga                       103

<210> SEQ ID NO 40
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcaaggctct gagacctttg ataacataac cattagcaga gaggctcagg ctggagtcca     60
aatcaaacag gcattcccaa atactaga                                        88

<210> SEQ ID NO 41
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gagacctttg ataacataac cattagcaga gaggctcagg ctggagtccc aaataaacca     60
```
ggcattccca aaattactag a                                          81

<210> SEQ ID NO 42
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtcctgtcaa ggctctgaga cctttgataa cataaccatt agcagagagg ctcaggctgg    60
agtcccaaat aaaccaggca ttcccaaatt actaga                              96

<210> SEQ ID NO 43
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gcaggatgtc cctgtcaagg ctctgagacc tttgataaca taaccattag cagagaggct    60
caggatgatt tttggatacc agaaacaagt tcatactta cta                       103

<210> SEQ ID NO 44
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
ggcgcaggag gggcaggatg tccctgtcaa ggctctgaga cctttgataa cataaccatt    60
agcagagagg ctcaggatga ttttggata ccagaaacaa gtttcatact tacta         115

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccatctcatc cctgcgtgtc tccgactcag ctaaggtaac tggcgt                   46

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgccaggttc cagtcacgac                                                20

<210> SEQ ID NO 47
<211> LENGTH: 70
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 47
aatgatacgg cgaccaccga gatctacact agatcgcaca ctctttccct acacgacgct    60
cttccgatct                                                           70

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatcggaaga gccagttacc ttagctgagt cggagacacg cagggatgag atgg          54

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctaaggtaac                                                           10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
taaggagaac                                                           10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aagaggattc                                                           10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
taccaagatc                                                           10

<210> SEQ ID NO 53
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
cagaaggaac                                                          10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctgcaagttc                                                          10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttcgtgattc                                                          10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttccgataac                                                          10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ctgaccgaac                                                          10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcctcgaatc                                                          10

<210> SEQ ID NO 59
<211> LENGTH: 10
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 59
taggtggttc                                                                 10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tctaacggac                                                                 10
```

METHODS FOR DETERMINING A NUCLEOTIDE SEQUENCE CONTIGUOUS TO A KNOWN TARGET NUCLEOTIDE SEQUENCE

CROSS-REFERENCE TO RELATED APPLICATIONS

This application is a continuation under 35 U.S.C. § 120 of U.S. application Ser. No. 15/984,612 filed May 21, 2018, now U.S. Pat. No. 10,718,009, which is a continuation under 35 U.S.C. § 120 of U.S. application Ser. No. 15/269,448 filed Sep. 19, 2016, now U.S. Pat. No. 10,017,810, which is a continuation under 35 U.S.C. § 120 of U.S. application Ser. No. 13/793,564 filed Mar. 11, 2013 now U.S. Pat. No. 9,487,828B2, and which claims benefit under 35 U.S.C. § 119(e) of U.S. Provisional Application Nos. 61/645,364 filed May 10, 2012 and 61/679,302 filed Aug. 3, 2012, the contents of which are incorporated herein by reference in their entirety.

GOVERNMENT SUPPORT

This invention was made with federal funding under Grant No. 5R21CA161590 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 1, 2022, is named 030258-074968USC4_SL.txt and is 44,747 bytes in size.

TECHNICAL FIELD

The technology described herein relates to methods of determining oligonucleotide sequences.

BACKGROUND

Target enrichment prior to next-generation sequencing is more cost-effective than whole genome, whole exome, and whole transcriptome sequencing and therefore more practical for broad implementation; both for research discovery and clinical applications. For example, high coverage depth afforded by target enrichment approaches enables a wider dynamic range for allele counting (in gene expression and copy number assessment) and detection of low frequency mutations, a critical feature for evaluating somatic mutations in cancer. Examples of current enrichment protocols for next generation sequencing include hybridization-based capture assays (TruSeq Capture™ Illumina; SureSelect Hybrid Capture™, Agilent) and polymerase chain reaction (PCR)-based assays (HaloPlex™, Agilent; AmpliSeq™, Ion Torrent™; TruSeq Amplicon™, Illumina; emulsion/digital PCR, Raindance). Hybridization-based approaches capture not only the targeted sequences covered by the capture probes but also near off-target bases that consume sequencing capacity. In addition, these methods are relatively time-consuming, labor-intensive, and suffer from a relatively low level of specificity. A PCR amplification based approach is simpler and faster but by conventional design requires the use of both forward and reverse primers flanking the target loci. In particular, for detection of genomic rearrangements with unknown fusion partners, PCR is not applicable.

SUMMARY

The technology described herein is directed to methods of determining oligonucleotide sequences. In some embodiments, the methods described herein relate to enriching target sequences prior to sequencing the sequences.

In one aspect, the technology described herein relates to a method of determining the nucleotide sequence contiguous to a known target nucleotide sequence, the method comprising; (a) ligating a target nucleic acid comprising the known target nucleotide sequence with a universal oligonucleotide tail-adaptor; (b) amplifying a portion of the target nucleic acid and the amplification strand of the universal oligonucleotide tail-adaptor with a first adaptor primer and a first target-specific primer; (c) amplifying a portion of the amplicon resulting from step (b) with a second adaptor primer and a second target-specific primer; (d) sequencing the amplified portion from step (c) using a first and second sequencing primer; wherein the universal oligonucleotide tail-adaptor comprises a first ligatable duplex end and a second unpaired end; wherein the universal oligonucleotide tail-adaptor comprises a blocking strand and an amplification strand; wherein the blocking strand comprises a 5' duplex portion; wherein the amplification strand comprises an unpaired 5' portion, a 3' duplex portion, and a 3' T overhang; wherein the amplification strand comprises nucleic acid sequences identical to a first and second sequencing primers; wherein the duplex portions of the blocking strand and the amplification strand are substantially complementary and form the first ligatable duplex end comprising a 3' T overhang; wherein the duplex portion is of sufficient length to remain in duplex form at the ligation temperature; wherein the first target-specific primer comprises a nucleic acid sequence that can specifically anneal to the known target nucleotide sequence of the target nucleic acid at the annealing temperature; wherein the second target-specific primer comprises a 3' portion comprising a nucleic acid sequence that can specifically anneal to a portion of the known target nucleotide sequence comprised by the amplicon resulting from step (b), and a 5' portion comprising a nucleic acid sequence that is identical to a second sequencing primer and the second target-specific primer is nested with respect to the first target-specific primer; wherein the first adaptor primer comprises a nucleic acid sequence identical to a 5' portion of the first sequencing primer; and wherein the second adaptor primer comprises a nucleic acid sequence identical to a portion of the first sequencing primer and is nested with respect to the first adaptor primer.

In some embodiments, the blocking strand of the universal oligonucleotide tail-adaptor can further comprise a 3' unpaired portion which is not substantially complementary to the 5' unpaired portion of the amplification strand; and wherein the 3' unpaired portion of the blocking strand is not substantially complementary to or substantially identical to any of the primers. In some embodiments, the second adaptor primer can be nested with respect to the first adaptor primer by at least 3 nucleotides. In some embodiments, the portion of the amplification strand that comprises a nucleic acid sequence identical to a first and second sequencing primers can be comprised, at least in part, by the 5' unpaired portion of the amplification strand.

In some embodiments, the first target-specific primer can further comprise a 5' tag sequence portion comprising a nucleic acid sequence of high GC content which is not substantially complementary to or substantially identical to any other portion of any of the primers. In some embodiments, the first target-specific primer can further comprise a 5' tag sequence portion comprising a nucleic acid sequence of high GC content which will not specifically anneal to any other portion of any of the primers or their complements at the annealing temperature. In some embodiments, the second adaptor primer can be identical to the full-length first sequencing primer. In some embodiments, the portions of the target-specific primers that specifically anneal to the known target can anneal specifically at a temperature of about 65° C. in a PCR buffer.

In some embodiments, the method can further; prior to step (a), the steps of: mechanically shearing the nucleic acid; subjecting the nucleic acid to end-repair; subjecting the nucleic acid to phosphorylation; and subjecting the nucleic acid to adenylation. In some embodiments, the sample can comprise genomic DNA. In some embodiments, the sample can comprise RNA and the method can further comprise a first step of subjecting the sample to a reverse transcriptase regimen. In some embodiments, the reverse transcriptase regimen can comprise the use of random hexamers.

In some embodiments, the known target sequence can be comprised by a gene rearrangement. In some embodiments, the gene rearrangement can be present in a nucleic acid selected from the group consisting of: genomic DNA; RNA; and cDNA. In some embodiments, the gene rearrangement can comprise an oncogene. In some embodiments, the gene rearrangement can comprise a fusion oncogene.

In some embodiments, the nucleic acid product can be sequenced by a next-generation sequencing method. In some embodiments, the next-generation sequencing method can comprise a method selected from the group consisting of: Ion Torrent™, Illumina, SOLiD™, 454™; Massively Parallel Signature Sequencing solid-phase, reversible dye-terminator sequencing; and DNA nanoball sequencing. In some embodiments, the first and second sequencing primers are compatible with the selected next-generation sequencing method.

In some embodiments, the method can comprise contacting the sample, or separate portions of the sample, with a plurality of sets of first and second target-specific primers. In some embodiments, the method can comprise contacting a single reaction mixture comprising the sample with a plurality of sets of first and second target-specific primers. In some embodiments, the plurality of sets of first and second target-specific primers can specifically anneal to known target nucleotide sequences comprised by separate genes. In some embodiments, at least two sets of first and second target-specific primers can specifically anneal to different portions of a known target nucleotide sequence. In some embodiments, at least two sets of first and second target-specific primers can specifically anneal to different portions of a single gene comprising a known target nucleotide sequence. In some embodiments, at least two sets of first and second target-specific primers can specifically anneal to different exons of a gene comprising a known nucleotide target sequence. In some embodiments, the plurality of first target-specific primers can comprise identical 5' tag sequence portions. In some embodiments, the universal oligonucleotide tail-adaptor can further comprise a barcode portion. In some embodiments, multiple samples can each be contacted with a universal oligonucleotide tail-adaptor with a unique barcode portion and wherein the samples are pooled after step (a).

In some embodiments, each amplification step can comprise a set of cycles of a PCR amplification regimen from 5 cycles to 20 cycles in length. In some embodiments, the target-specific primers and the adaptor primers can be designed such that they will specifically anneal to their complementary sequences at an annealing temperature of from about 61 to 72° C. In some embodiments, the target-specific primers and the adaptor primers can be designed such that they will specifically anneal to their complementary sequences at an annealing temperature of about 65° C.

In some embodiments, the sample can comprise a biological sample obtained from a subject. In some embodiments, the sample can be obtained from a subject in need of treatment for a disease associated with a genetic alteration. In some embodiments, the disease can be cancer. In some embodiments, the sample can comprise a population of tumor cells. In some embodiments, the sample can comprise a tumor biopsy. In some embodiments, the cancer can be lung cancer.

In some embodiments, the known target sequence can be comprised by a disease-associated gene. In some embodiments, the known target sequence can be comprised by a gene rearrangement product in the sample. In some embodiments, the gene rearrangement product can be an oncogene.

In some embodiments, the known target sequence can comprise a sequence from a gene selected from the group of: ALK; ROS1; and RET. In some embodiments, at least one set of a first target-specific primer and a second target-specific primer can be selected from the group consisting of; SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; SEQ ID NOs: 21 and 22; SEQ ID NOs: 23 and 24; SEQ ID NOs: 25 and 26; SEQ ID NOs: 27 and 28; SEQ ID NOs: 29 and 30; SEQ ID NOs: 31 and 32; SEQ ID NOs: 33 and 34; SEQ ID NOs: 35 and 36; and SEQ ID NOs: 37 and 38.

In some embodiments, the presence of a gene rearrangement of ALK in a sample obtained from a tumor in a subject can indicate that the tumor is susceptible to treatment with a treatment selected from the group consisting of: an ALK inhibitor; crizotinib (PF-02341066); AP26113; LDK378; 3-39; AF802; IPI-504; ASP3026; AP-26113; X-396; GSK-1838705A; CH5424802; and NVP-TAE684.

In some embodiments, the presence of a gene rearrangement of ROS1 in a sample obtained from a tumor in a subject can indicate that the tumor is susceptible to treatment with a treatment selected from the group consisting of: a ROS inhibitor; an ALK inhibitor; crizotinib (PF-02341066); AP26113; LDK378; 3-39; AF802; IPI-504; ASP3026; AP-26113; X-396; GSK-1838705A; CH5424802; and NVP-TAE684.

In some embodiments, the presence of a gene rearrangement of RET in a sample obtained from a tumor in a subject can indicate that the tumor is susceptible to treatment with a treatment selected from the group consisting of: a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A.

In one aspect, the technology described herein relates to a method of treating cancer, the method comprising; detecting, in a tumor sample obtained from a subject in need of treatment for cancer, the presence of one or more oncogene rearrangements according to the method described herein; administering a cancer treatment which is effective against tumors having any of the detected oncogene rearrangements. In some embodiments, a treatment selected from the group consisting of: an ALK inhibitor; crizotinib (PF-02341066);

AP26113; LDK378; 3-39; AF802; IPI-504; ASP3026; AP-26113; X-396; GSK-1838705A; CH5424802; and NVP-TAE684; can be effective against tumors having an ALK oncogene rearrangement. In some embodiments, a treatment selected from the group consisting of: a ROS1 inhibitor; an ALK inhibitor; crizotinib (PF-02341066); AP26113; LDK378; 3-39; AF802; IPI-504; ASP3026; AP-26113; X-396; GSK-1838705A; CH5424802; and NVP-TAE684; can be effective against tumors having an ROS1 oncogene rearrangement. In some embodiments, a treatment selected from the group consisting of: a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A; can be effective against tumors having an RET oncogene rearrangement.

In one aspect, the technology described herein relates to a method of determining if a subject in need of treatment for cancer will be responsive to a given treatment, the method comprising; detecting, in a tumor sample obtained from the subject, the presence of an oncogene rearrangement according to the method as described herein; wherein the subject is determined to be responsive to a treatment targeting an oncogene rearrangement product if the presence of the oncogene rearrangement is detected.

In some embodiments, when the presence of an ALK oncogene rearrangement is detected, the subject can be responsive to a treatment selected from the group consisting of: an ALK inhibitor; crizotinib (PF-02341066); AP26113; LDK378; 3-39; AF802; IPI-504; ASP3026; AP-26113; X-396; GSK-1838705A; CH5424802; and NVP-TAE684. In some embodiments, when the presence of an ROS1 oncogene rearrangement is detected, the subject can be responsive to a treatment selected from the group consisting of: an ALK inhibitor; crizotinib (PF-02341066); AP26113; LDK378; 3-39; AF802; IPI-504; ASP3026; AP-26113; X-396; GSK-1838705A; CH5424802; and NVP-TAE684.

In some embodiments, when the presence of an RET oncogene rearrangement is detected, the subject will be responsive to a treatment selected from the group consisting of: a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A.

In some embodiments, the cancer can be lung cancer.

BRIEF DESCRIPTION OF THE DRAWINGS

FIG. 4B depicts the sequence of two alternative spliced fusion sequences (SEQ ID NOs: 39-44, respectively, in order of appearance). FIG. 4C depicts a summary table reporting fusion transcripts in involved genes annotated with exon, frame, and fusion read coverage details.

DETAILED DESCRIPTION

Figure 1:
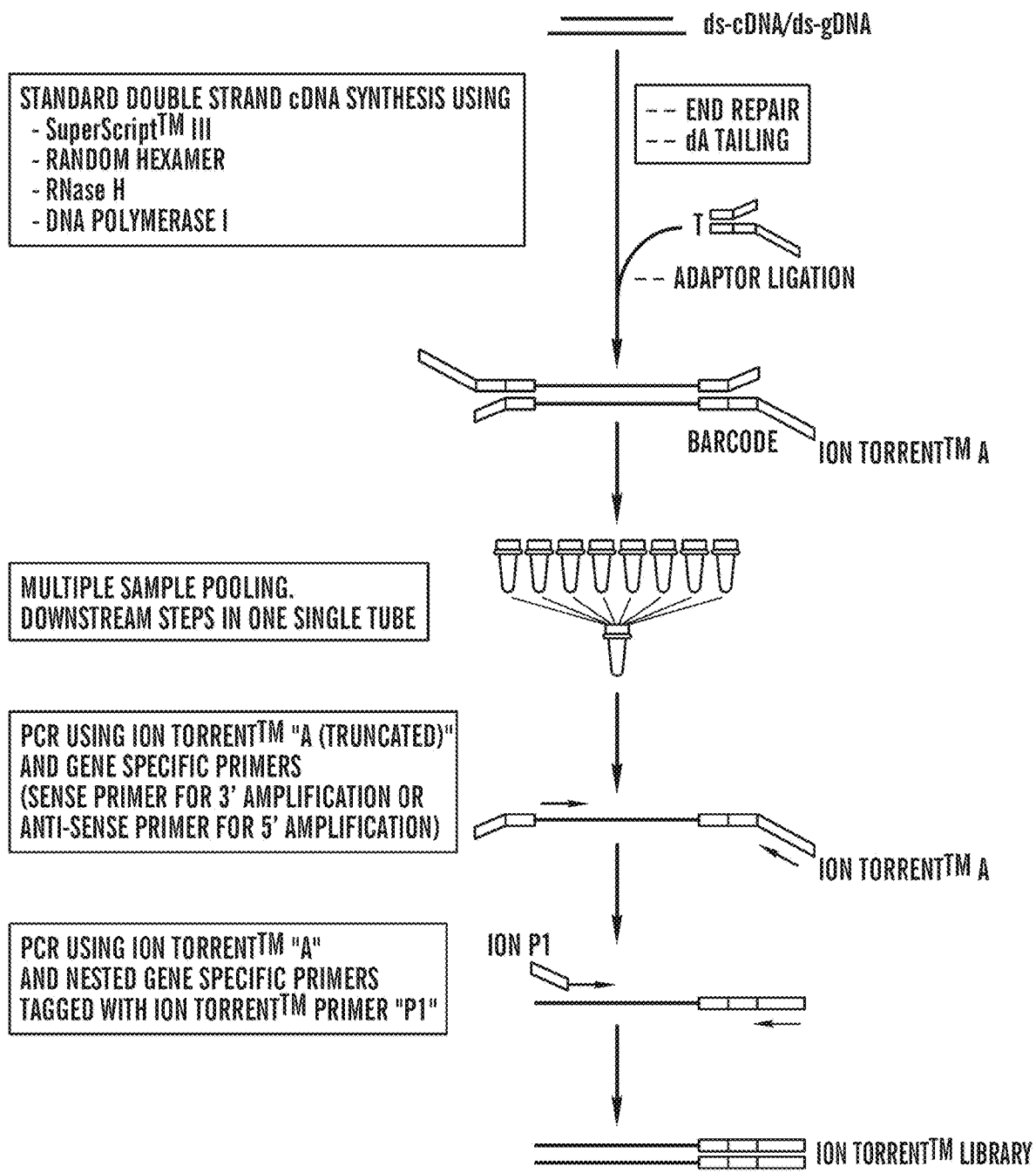
FIG. 1 depicts a schematic illustration of an example of library construction for targeted RNA and DNA sequencing. 1) A standard procedure of double-stranded cDNA synthesis is applied using total nucleic acid from FFPE specimen as starting material. Alternatively, the starting material may also be sheared gDNA. 2) After cleanup, the double stranded cDNA or gDNA is subjected to end-repair and dA tailing, directly followed by ligation of a half-truncated Y adapter without cleanup in between. In some embodiments, the half-truncated Y adapter comprises a barcode. 3) After SPRI cleanup, the ligated sample is subjected to 14 cycles of PCR amplification using multiplex gene specific primers (GSP1s) and Ion Torrent™ short length Forward primer A 5' 20-mer (A20), with annealing temperature at 65° C. 4). After a second SPRI cleanup, the sample is subjected to an additional 14 cycles of PCR amplification using multiplex nested gene specific primers (3' downstream of GSP1 and in the same direction) tagged with Ion Torrent™ Reverse primer (P1_GSP2s) and Forward primer A (full length 30-mer), with annealing temperature at 65° C. As shown in this embodiment, the amplification products of (3) and (4) can retain the barcode of the adaptor. 5) After a final third SPRI cleanup, the product is Ion Torrent™ library ready for downstream emulsion PCR and sequencing. Sample pooling may be carried out after Step 2.

Embodiments of the technology described herein relate to methods of determining (i.e sequencing) oligonucleotide sequences. In some embodiments, the methods described herein relate to methods of enriching target sequences prior to a sequencing step. In some embodiments, the sequence of one end of the target sequence to be enriched is not known prior to the sequencing step.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein generally to mean a decrease by a statistically significant amount. However, for avoidance of doubt, "reduced", "reduction", "decrease", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. lung cancer. A subject can be male or female.

A subject can be one who has been previously diagnosed with or identified as suffering from or having a condition in need of treatment (e.g. cancer) or one or more complications related to such a condition, and optionally, have already undergone treatment for the condition or the one or more complications related to the condition. Alternatively, a subject can also be one who has not been previously diagnosed as having the condition (e.g. cancer) or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, a "disease associated with a genetic alteration" refers to any disease which is caused by, at least in part, by an alteration in the genetic material of the subject as compared to a healthy wildtype subject, e.g. a deletion, an insertion, a SNP, a gene rearrangement. A disease can be caused by, at least in part, an alteration in the genetic material of the subject if the alteration increases the risk of the subject developing the disease, increases the subject's susceptibility to a disease (including infectious diseases, or diseases with an infectious component), causes the production of a disease-associated molecule, or causes cells to become diseased or abnormal (e.g. loss of cell cycle regulation in cancer cells). Diseases can be associated with multiple genetic alterations, e.g. cancers.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

The term "isolated" or "partially purified" as used herein refers, in the case of a nucleic acid, to a nucleic acid separated from at least one other component (e.g., nucleic acid or polypeptide) that is present with the nucleic acid as found in its natural source and/or that would be present with the nucleic acid when expressed by a cell. A chemically synthesized nucleic acid or one synthesized using in vitro transcription/translation is considered "isolated."

The term "gene" means a nucleic acid sequence which is transcribed (DNA) to RNA in vitro or in vivo when operably linked to appropriate regulatory sequences. The gene can include regulatory regions preceding and following the coding region, e.g. 5' untranslated (5'UTR) or "leader" sequences and 3' UTR or "trailer" sequences, as well as intervening sequences (introns) between individual coding segments (exons).

As used herein, the term "complementary" refers to the hierarchy of hydrogen-bonded base pair formation preferences between the nucleotide bases G, A, T, C and U, such that when two given polynucleotides or polynucleotide sequences anneal to each other, A pairs with T and G pairs with C in DNA, and G pairs with C and A pairs with U in RNA. As used herein, "substantially complementary" refers to a nucleic acid molecule or portion thereof (e.g. a primer) having at least 90% complementarity over the entire length of the molecule or portion thereof with a second nucleotide sequence, e.g. 90% complementary, 95% complementary, 98% complementary, 99% complementary, or 100% complementary. As used herein, "substantially identical" refers to a nucleic acid molecule or portion thereof having at least 90% identity over the entire length of a the molecule or portion thereof with a second nucleotide sequence, e.g. 90% identity, 95% identity, 98% identity, 99% identity, or 100% identity.

As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

As used herein, "amplified product", "amplification product", or "amplicon" refers to oligonucleotides resulting from a PCR reaction that are copies of a portion of a particular target nucleic acid template strand and/or its complementary sequence, which correspond in nucleotide sequence to the template oligonucleotide sequence and/or its complementary sequence. An amplification product can further comprise sequence specific to the primers and which flanks sequence which is a portion of the target nucleic acid and/or its complement. An amplified product, as described herein will generally be double-stranded DNA, although reference can be made to individual strands thereof.

As used herein, a "portion" of a nucleic acid molecule refers to contiguous set of nucleotides comprised by that molecule. A portion can comprise all or only a subset of the nucleotides comprised by the molecule. A portion can be double-stranded or single-stranded.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. lung cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

The term "statistically significant" or "significantly" refers to statistical significance and generally means a two standard deviation (2SD) below normal, or lower, concentration of the marker.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); and Davis et al., Basic Methods in Molecular Biology, Elsevier Science Publishing, Inc., New York, USA (1995) which are all incorporated by reference herein in their entireties.

Other terms are defined herein within the description of the various aspects of the invention.

Described herein are methods of determining the nucleotide sequence contiguous to a known target nucleotide sequence. Traditional sequencing methods generate sequence information randomly (e.g. "shotgun" sequencing) or between two known sequences which are used to design primers. In contrast, the methods described herein, in some embodiments, allow for determining the nucleotide sequence (e.g. sequencing) upstream or downstream of a single region of known sequence with a high level of specificity and sensitivity.

In some embodiments, the methods described herein relate to a method of enriching specific nucleotide sequences prior to determining the nucleotide sequence using a next-generation sequencing technology. In some embodiments, the methods of enriching specific nucleotide sequences do not comprise hybridization enrichment.

In some embodiments, the technology described herein can relate to a method of determining the nucleotide sequence contiguous to a known target nucleotide sequence, the method comprising; (a) ligating a target nucleic acid comprising the known target nucleotide sequence with a universal oligonucleotide tail-adaptor; (b) amplifying a portion of the target nucleic acid and the amplification strand of the universal oligonucleotide tail-adaptor with a first adaptor primer and a first target-specific primer; (c) amplifying a portion of the amplicon resulting from step (b) with a second adaptor primer and a second target-specific primer; and (d)

sequencing the amplified portion from step (c) using a first and second sequencing primer. As used herein, the term "target nucleic acid" refers to a nucleic acid molecule comprising both the nucleic acid sequence which is to be determined and the known target nucleotide sequence. The target nucleic acid can be of any length and can be double-stranded or single-stranded. As used herein, the term "known target nucleotide sequence" refers to a portion of a target nucleic acid for which the sequence (e.g. the identity and order of the nucleotide bases comprises the nucleic acid) is known. The known target nucleotide sequence can be of any length of 10 or more nucleotides, preferably 30 or more nucleotides (e.g. 30 nucleotides, 40 nucleotides, 50 nucleotides or more). As used herein, the term "nucleotide sequence contiguous to" refers to a nucleotide sequence which is located on the same nucleic acid molecule (i.e. the target nucleic acid) as the known target nucleotide sequence and either upstream or downstream of the known target nucleotide sequence. The nucleotide sequence contiguous to can comprise any length of nucleotide sequence. In some embodiments, the nucleotide sequence contiguous to the known target nucleotide sequence comprises 1 kb or less of nucleotide sequence, e.g. 1 kb or less of nucleotide sequence, 750 bp or less of nucleotide sequence, 500 bp or less of nucleotide sequence, 400 bp or less of nucleotide sequence, 300 bp or less of nucleotide sequence, 200 bp or less of nucleotide sequence, 100 bp or less of nucleotide sequence. Where a sample comprises different target nucleic acids comprising the known target nucleotide sequence (e.g. a cell where the known target nucleotide sequence occurs multiple times in the genome, or on separate, non-identical chromosomes), there can be multiple sequences which comprise "nucleotide sequence contiguous to" the known target nucleotide sequence. As used herein, the term "determining the nucleotide sequence", refers to determining the identity and relative positions of the nucleotide bases comprising a nucleic acid.

In step (a) of the method described herein, the universal oligonucleotide tail-adaptor can be ligated to the target nucleic acid. In some embodiments, the target nucleic acid can be comprised by a sample comprising a plurality of nucleic acids, some of which do not comprise the target nucleic acid. In some embodiments, the universal oligonucleotide tail-adaptor can be ligated to substantially all of the nucleic acids in a sample. In some embodiments, the universal oligonucleotide tail-adaptor can be ligated to both nucleic acids which comprise the target nucleic acid sequence and to nucleic acids which do not comprise the target nucleic acid sequence.

As used herein, the term "universal oligonucleotide tail-adaptor" refers to a nucleic acid molecule comprised of two strands (a blocking strand and an amplification strand) and comprising a first ligatable duplex end and a second unpaired end. The blocking strand of the universal oligonucleotide tail-adaptor comprises a 5' duplex portion. The amplification strand comprises an unpaired 5' portion, a 3' duplex portion, and a 3' T overhang and nucleic acid sequences identical to a first and second sequencing primers. The duplex portions of the blocking strand and the amplification strand are substantially complementary and form the first ligatable duplex end comprising a 3' T overhang and the duplex portion is of sufficient length to remain in duplex form at the ligation temperature.

In some embodiments, the portion of the amplification strand that comprises a nucleic acid sequence identical to a first and second sequencing primers can be comprised, at least in part, by the 5' unpaired portion of the amplification strand.

In some embodiments, the universal oligonucleotide tail-adaptor can comprise a duplex portion and an unpaired portion, wherein the unpaired portion comprises only the 5' portion of the amplification strand, i.e. the entirety of the blocking strand is a duplex portion.

In some embodiments, the universal oligonucleotide tail-adaptor can have a "Y" shape, i.e. the unpaired portion can comprise portions of both the blocking strand and the amplification strand which are unpaired. The unpaired portion of the blocking strand can be shorter than, longer than, or equal in length to the unpaired portion of the amplification strand. In some embodiments, the unpaired portion of the blocking strand can be shorter than the unpaired portion of the amplification strand. Y shaped universal oligonucleotide tail-adaptors have the the advantage that the unpaired portion of the blocking strand will not be subject to 3' extension during a PCR regimen.

In some embodiments, the blocking strand of the universal oligonucleotide tail-adaptor can further comprise a 3' unpaired portion which is not substantially complementary to the 5' unpaired portion of the amplification strand; and wherein the 3' unpaired portion of the blocking strand is not substantially complementary to or substantially identical to any of the primers. In some embodiments, the blocking strand of the universal oligonucleotide tail-adaptor can further comprise a 3' unpaired portion which will not specifically anneal to the 5' unpaired portion of the amplification strand at the annealing temperature; and wherein the 3' unpaired portion of the blocking strand will not specifically anneal to any of the primers or the complements thereof at the annealing temperature.

In some embodiments, the duplex portion of the universal oligonucleotide tail-adaptor (e.g. the duplex portions of either or both of the strands) is at least 7 base pairs in length, e.g. 7 bp or more, 8 bp or more, 9 bp or more, 10 bp or more, 11 bp or more, 12 bp or more, 13 bp or more, or 14 bp or more in length. In some embodiments, the duplex portion of a universal oligonucleotide tail-adaptor can be at least 30 bp or longer, e.g. 30 bp or more, 31 bp or more, 32 bp or more, 33 bp or more, 34 bp or more, 35 bp or more, 40 bp or more, or 50 bp or more in length. The duplex portion of a universal oligonucleotide tail-adaptor should not be so long as to suppress PCR amplification of the desired amplicons in the PCR amplification regimen being used. Some next-generation sequencing methods use Y-shaped adaptor molecules. These Y-shaped adaptor molecules require duplex portions that are of limited length, (e.g. 17 bp or less) to avoid the formation of intramolecular hairpins during several PCR steps (e.g. library enrichment PCR, bridge PCR, or emulsion PCR). The Y-shaped universal oligonucleotide tail-adaptors of the methods described herein are not subject to this limitation of the duplex end as the two This PCR suppression effect resulting from the duplex end is not applicable in this invention since the two target primers can access the target fragment internally. In some embodiments, the duplex portion of a universal oligonucleotide tail-adaptor can be at least 18 bp or longer, e.g. 18 bp or more, 19 bp or more, 20 bp or more, 21 bp or more, 22 bp or more, 23 bp or more, 24 bp or more, or 25 bp or more in length.

Figure 9:
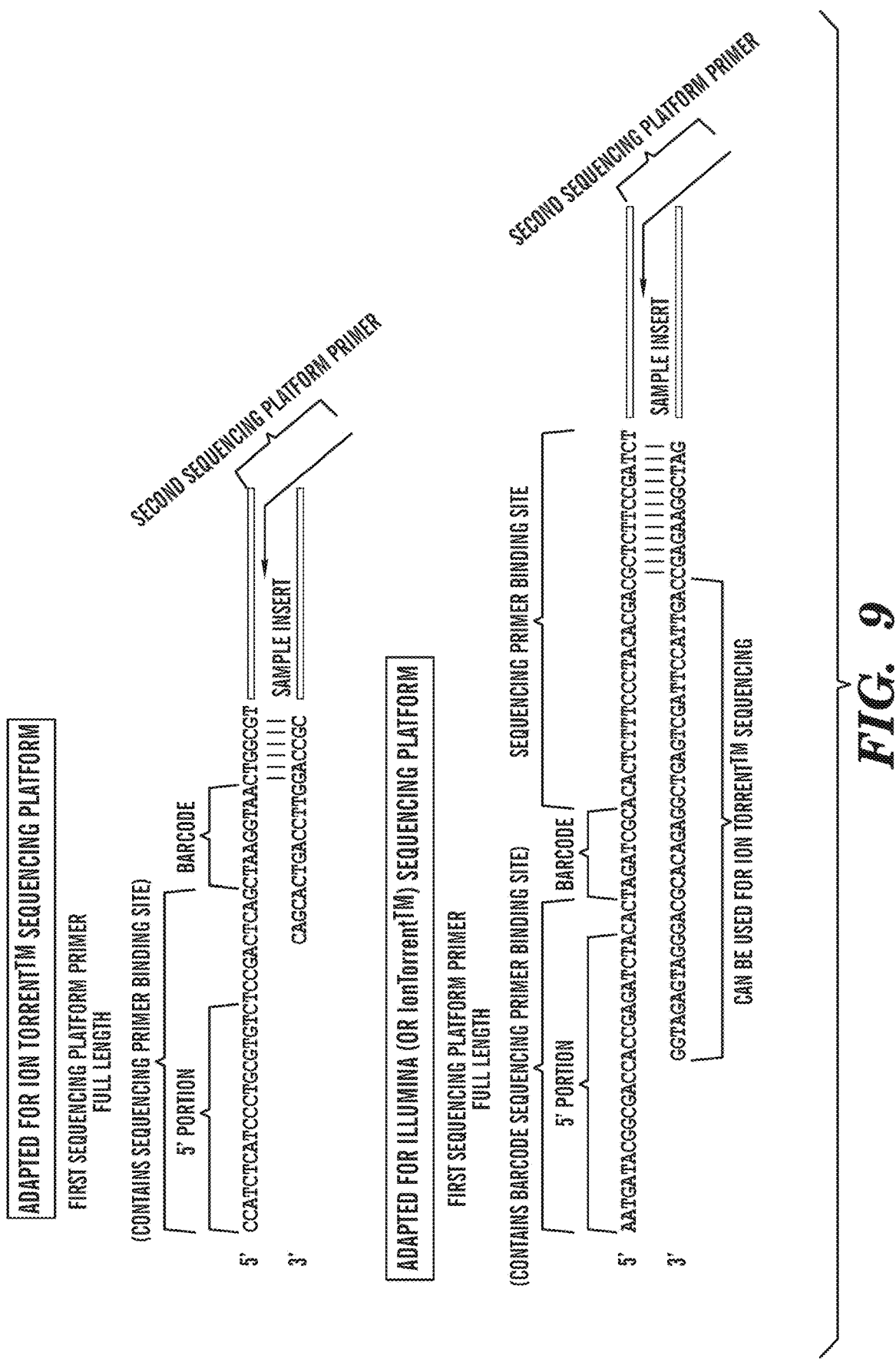
FIG. 9 depicts schematics of illustrative universal oligonucleotide tail-adaptors (SEQ ID NOs: 45-48, respectively, in order of appearance). As shown in this embodiment, the universal oligonucleotide tail-adaptor may comprise a barcode.

Illustrative examples of universal oligonucleotide tail-adaptors are shown in FIG. 9.

Ligation of the universal oligonucleotide tail-adaptor can be accomplished by any method known in the art, e.g. blunt-end ligation or TA ligation. In some embodiments, prior to ligation of the Universal oligonucleotide tail-adaptor, the nucleic acids in a sample can be subjected to nucleic acid end-repair to blunt the ends of the nucleic acid. End-repair is well known in the art and relevant kits and/or enzymes are available commercially, (e.g. the NEBNEXT™ End Repair Module (Cat No. E6050L; New England Biolabs; Ipswich, Mass.).

In some embodiments, prior to ligation of the universal oligonucleotide tail-adaptor, the nucleic acids in a sample can be phosphorylated and/or adenylated. Adenylation can provide an adenosine overhang on the 3' end of a nucleic acid. A second nucleic acid with a thionine 3' overhang can then be ligated to the the first nucleic acid by TA ligation. Methods of ligation are well known in the art and relevant kits and/or enzymes are available commercially, e.g. the NEBNEXT™ da-Tailing module (Cat No. E6053L: New England Biolabs; Ipswich, Mass.) can be used to adenylate a blunt end of a nucleic acid. In some embodiments, Universal oligonucleotide tail-adaptors can be provided with a a thioninie 3' overhang.

Steps (b) and (c) of the methods described herein can each comprise a PCR amplification regimen, i.e. a set of polymerase chain reaction (PCR) amplification cycles. As used herein, the term "amplification regimen" refers to a process of specifically amplifying, i.e., increasing the abundance of, a nucleic acid sequence of interest, and more particularly, the exponential amplification occurring when the products of a previous polymerase extension serve as templates for the successive rounds of extension. A PCR amplification regimen according to the invention comprises at least one, and preferably at least 5 or more iterative cycles, where each cycle comprises the steps of: 1) strand separation (e.g., thermal denaturation); 2) oligonucleotide primer annealing to template molecules; and 3) nucleic acid polymerase extension of the annealed primers. Conditions and times necessary for each of these steps can be devised by one of ordinary skill in the art. An amplification regimen according to the methods described herein is preferably performed in a thermal cycler, many of which are commercially available.

PCR requires the use of a nucleic acid polymerase. As used herein, the phrase "nucleic acid polymerase" refers an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and commercially available. One group of preferred nucleic acid polymerases are thermostable, i.e., they retain function after being subjected to temperatures sufficient to denature annealed strands of complementary nucleic acids, e.g. 94° C., or sometimes higher.

As understood in the art, PCR requires cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. More specifically, strand separation according to the methods described herein is achieved by heating the nucleic acid sample above its $T_m$. Generally, for a sample containing nucleic acid molecules in buffer suitable for a nucleic acid polymerase, heating to 94° C. is sufficient to achieve strand separation. An exemplary buffer contains 50 mM KCl, 10 mM Tris-HCl (pH 8.8@25° C.), 0.5 to 3 mM $MgCl_2$, and 0.1% BSA.

As also understood in the art, PCR requires annealing primers to template nucleic acids. Any strand of a target nucleic acid can be a template nucleic acid, as the template nucleic acid is defined as a single-strand nucleic acid to which a given primer will specifically anneal. As used herein, "anneal" refers to permitting two complementary or substantially complementary nucleic acids strands to hybridize, and more particularly, when used in the context of PCR, to hybridize such that a primer extension substrate for a template-dependent polymerase enzyme is formed. Conditions for primer-target nucleic acid annealing vary with the length and sequence of the primer and are based upon the calculated $T_m$ for the primer. Generally, an annealing step in an amplification regimen involves reducing the temperature following the strand separation step to a temperature based on the calculated $T_m$ for the primer sequence, for a time sufficient to permit such annealing. $T_m$ can be readily predicted by one of skill in the art using any of a number of widely available algorithms (e.g., OLIGO' (Molecular Biology Insights Inc. Colorado) primer design software and VENTRO NTI™ (Invitrogen, Inc. California) primer design software and programs available on the internet, including Primer3, Oligo Calculator, and NetPrimer™ (Premier Biosoft; Palo Alto, Calif.; and freely available on the world wide web). For example, the $T_m$ of a primer can be calculated using following formula, which is used by NetPrimer™ software and is described in more detail in Frieir et al. PNAS 1986 83:9373-9377 which is incorporated by reference herein in its entirety.

$$T_m = \Delta H/(\Delta S + R^* \ln(C/4)) + 16.6 \log([K^+]/(1+0.7[K^+])) - 273.15$$

wherein, ΔH is enthalpy for helix formation; ΔS is entropy for helix formation; R is molar gas constant (1.987 cal/° C.*mol); C is the nucleic acid concentration; and [$K^+$] is salt concentration. For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can, for example, temperatures more than 5° C. below the predicted $T_m$ (e.g., 6° C. below, 8° C. below, 10° C. below or lower). Generally, the closer the annealing temperature is to the $T_m$, the more specific is the annealing. The time allowed for primer annealing during a PCR amplification regimen depends largely upon the volume of the reaction, with larger volumes requiring longer times, but also depends upon primer and template concentrations, with higher relative concentrations of primer to template requiring less time than lower relative concentrations. Depending upon volume and relative primer/template concentration, primer annealing steps in an amplification regimen can be on the order of 1 second to 5 minutes, but will generally be between 10 seconds and 2 minutes, preferably on the order of 30 seconds to 2 minutes. As used herein, "substantially anneal" refers to a degree of annealing during a PCR amplification regimen which is sufficient to produce a detectable level of a specifically amplified product.

PCR also relies upon polymerase extension of annealed primers at each cycle. As used herein, the term "polymerase extension" means the template-dependent incorporation of at least one complementary nucleotide, by a nucleic acid polymerase, onto the 3' end of an annealed primer. Polymerase extension preferably adds more than one nucleotide, preferably up to and including nucleotides corresponding to the full length of the template. Conditions for polymerase extension vary with the identity of the polymerase. The temperature used for polymerase extension is generally based upon the known activity properties of the enzyme. Although, where annealing temperatures are required to be, for example, below the optimal temperatures for the enzyme, it will often be acceptable to use a lower extension temperature. In general, although the enzymes retain at least partial activity below their optimal extension temperatures, polymerase extension by the most commonly used thermostable polymerases (e.g., Taq polymerase and variants thereof) is performed at 65° C. to 75° C., preferably about 68-72° C.

Primer extension is performed under conditions that permit the extension of annealed oligonucleotide primers. As used herein, the term "conditions that permit the extension of an annealed oligonucleotide such that extension products are generated" refers to the set of conditions including, for example temperature, salt and co-factor concentrations, pH, and enzyme concentration under which a nucleic acid polymerase catalyzes primer extension. Such conditions will vary with the identity of the nucleic acid polymerase being used, but the conditions for a large number of useful polymerase enzymes are well known to those skilled in the art. One exemplary set of conditions is 50 mM KCl, 10 mM Tris-HCl (pH 8.8@25° C.), 0.5 to 3 mM $MgCl_2$, 200 uM each dNTP, and 0.1% BSA at 72° C., under which Taq polymerase catalyzes primer extension. The conditions for initiation and extension usually include the presence of at least one, but more preferably all four different deoxyribonucleoside triphosphates and a polymerization-inducing agent such as DNA polymerase or reverse transcriptase, in a suitable buffer (in this context "buffer" includes solvents (generally aqueous) plus necessary cofactors and reagents which affect pH, ionic strength, etc.) and at a suitable temperature.

In some embodiments, each amplification step can comprise a set of cycles of a PCR amplification regimen from 5 cycles to 20 cycles in length. In some embodiments, each amplification step can comprise a set of cycles of a PCR amplification regimen from 10 cycles to 20 cycles in length. In some embodiments, each amplification step can comprise a set of cycles of a PCR amplification regimen from 12 cycles to 16 cycles in length. In some embodiments, the annealing temperature can be less than 70° C. In some embodiments, the annealing temperature can be less than 72° C.

In various embodiments, the methods and compositions described herein relate to performing a PCR amplification regimen with one or more of the types of primers described herein. As used herein, "primer" refers to a DNA or RNA polynucleotide molecule or an analog thereof capable of specifically annealing to a polynucleotide template and providing a 3' end that serves as a substrate for a template-dependent polymerase to produce an extension product which is complementary to the polynucleotide template. A primer useful in the methods described herein is generally single-stranded, and a primer and its complement can anneal to form a double-stranded polynucleotide. Primers according to the methods and compositions described herein can be less than or equal to 300 nucleotides in length, e.g., less than or equal to 300, or 250, or 200, or 150, or 100, or 90, or 80, or 70, or 60, or 50, or 40, or 30 or fewer, or 20 or fewer, or 15 or fewer, but at least 10 nucleotides in length. Methods of making primers are well known in the art, and numerous commercial sources offer oligonucleotide synthesis services suitable for providing primers according to the methods and compositions described herein, e.g. INVITROGEN™ Custom DNA Oligos; Life Technologies; Grand Island, N.Y. or custom DNA Oligos from IDT; Coralville, Iowa).

In some embodiments, after the Universal oligonucleotide tail-adaptor is ligated to the nucleic acids in a sample (e.g. the target nucleic acids), the target nucleic acid can be amplified in a first amplification step (i.e. step (b)). The first amplification step can be a set of PCR amplification cycles using a first target-specific primer and a first tail-adaptor primer.

As used herein, the term "first target-specific primer" refers to a single-stranded oligonucleotide comprising a nucleic acid sequence that can specifically anneal to the target nucleic acid at the annealing temperature.

In some embodiments, the first-target specific primer can comprise a 5' tag sequence portion. In some embodiments, all first-target specific primers present in a reaction can comprise identical 5' tag sequence portions. In a multiplex PCR reaction, different primer species can interact with each other in an undesired off-target manner, leading to primer extension and subsequently amplification by DNA polymerase. These primer dimers tend to be short, and their efficient amplification can overtake the reaction and dominate resulting in poor amplification of desired target sequence. The inclusion of a 5' tag sequence on the first-target specific primer(s) causes any potential primer dimers that can result to contain the same complementary tails on both ends. In subsequent PCR cycles, the primer dimers would denature into single-stranded DNA primer dimers, each comprising complementary sequences on their two ends which are introduced by the 5' tag. Instead of primer annealing to these single stranded DNA primer dimers, an intra-molecular hairpin (a panhandle like structure) formation would preferentially occur due to the proximate accessibility of the complementary tags on the same primer dimer molecule instead of an inter-molecular interaction with new primers on separate molecules. As a result, these primer dimers are very inefficiently amplified, such that primers are not exponentially consumed by the undesired dimers for amplification. Instead the tagged primers can remain in high and sufficient concentration for desired specific amplification of target sequences. Accumulation of primer dimers can also be a detriment to multiplex PCR because they compete for and consume other reagents in the reaction. In some embodiments, the 5' tag sequence can be a GC-rich sequence, i.e. the tag sequence can comprise at least 50% GC content, at least 55% GC content, at least 60% GC content, at least 65% GC content, at least 70% GC content, at least 75% GC content, at least 80% GC content, or higher GC content. In some embodiments, the tag sequence can comprise at least 60% GC content. In some embodiments, the tag sequence can comprise at least 65% GC content.

As used herein, the term "second target-specific primer" refers to a single-stranded oligonucleotide comprising a 3' portion comprising a nucleic acid sequence that can specifically anneal to a portion of the known target nucleotide sequence comprised by the amplicon resulting from step (b), and a 5' portion comprising a nucleic acid sequence that is identical to a second sequencing primer. The second target-specific primer is nested with respect to the first target-specific primer. In some embodiments, the second target-specific primer is nested with respect to the first target-specific primer by at least 3 nucleotides, e.g. by 3 or more, 4 or more, 5 or more, 6 or more, 7 or more, 8 or more, 9 or more, 10 or more, or 15 or more nucleotides.

In some embodiments, all of the second target-specific primers present in a reaction comprise the same 5' portion. In some embodiments, the 5' portion the 5' portion of the can serve to suppress primer dimers as described for the 5' tag of the first target-specific primer described above herein.

In some embodiments, the first and second target-specific primers are substantially complementary to the same strand of the target nucleic acid. In some embodiments, the the portions of the first and second target-specific primers that specifically anneal to the known target sequence can comprise a total of at least 20 unique bases of the known target nucleotide sequence, e.g. 20 or more unique bases, 25 or more unique bases, 30 or more unique bases, 35 or more unique bases, 40 or more unique bases, or 50 or more unique bases. In some embodiments, the the portions of the first and second target-specific primers that specifically anneal to the known target sequence can comprise a total of at least 30 unique bases of the known target nucleotide sequence, As used herein, the term "first adaptor primer" refers to a nucleic acid molecule comprising a nucleic acid sequence identical to a 5' portion of the first sequencing primer. As the first tail-adaptor primer is therefor identical to at least a portion of the sequence of the amplification strand (as opposed to complementary), it will not be able to specifically anneal to any portion of the universal oligonucleotide tail-adaptor itself.

As used herein, the term "second adaptor primer" refers to a nucleic acid molecule comprising a nucleic acid sequence identical to a portion of the first sequencing primer and is nested with respect to the first adaptor primer. As the second tail-adaptor primer is is therefor identical to at least a portion of the sequence of the amplification strand (as opposed to complementary), it will not be able to specifically anneal to any portion of the universal oligonucleotide tail-adaptor itself. In some embodiments, the second adaptor primer is identical to the first sequencing primer.

The second adaptor primer should be nested with respect to the first adaptor primer, that is, the first adaptor primer comprises a nucleic acid sequence identical to the amplification strand which is not comprised by the second adaptor primer and which is located closer to the 5' end of the amplification primer than any of the sequence identical to the amplification strand which is comprised by the second adaptor primer. In some embodiments, the second adaptor primer is nested by at least 3 nucleotides, e.g. by 3 nucleotides, by 4 nucleotides, by 5 nucleotides, by 6 nucleotides, by 7 nucleotides, by 8 nucleotides, by 9 nucleotides, by 10 nucleotides or more.

In some embodiments, the first adaptor primer can comprise a nucleic acid sequence identical to about the 20 5'-most bases of the amplification strand of the universal oligonucleotide tail-adaptor and the second adaptor primer can comprise a nucleic acid sequence identical to about 30 bases of the amplification strand of the universal oligonucleotide tail-adaptor, with a 5' base which is at least 3 nucleotides 3' of the 5' terminus of the amplification strand.

The use of nested adaptor primers eliminates the possibility of producing final amplicons that are amplifiable (e.g. during bridge PCR or emulsion PCR) but cannot be sequence, a situation that can arise during hemi-nested methods. In other situations, hemi-nested approaches using a primer identical to a sequencing primer can result in the carry-over of undesired amplification products from the first PCR step to the second PCR step and would ultimately yield artificial sequencing reads. The use of two adaptor primers, as described herein can reduce, and in some embodiments eliminate, these problems.

In the first PCR amplification cycle of the first amplification step, the first target-specific primer can specifically anneal to a template strand of any nucleic acid comprising the known target nucleotide sequence. Depending upon the orientation with which the first target-specific primer was designed, sequence upstream or downstream of the known target nucleotide sequence, and complementary to the template strand will be synthesized. If, during the extension phase of PCR, the 5' end of the template strand terminates in a ligated Universal oligonucleotide tail-adaptor, the 3' end of the newly synthesized product strand will comprise sequence complementary to the first tail-adaptor primer. In subsequent PCR amplification cycles, both the first target-specific primer and the first tail-adaptor primer will be able to specifically anneal to the appropriate strands of the target nucleic acid sequence and the sequence between the known nucleotide target sequence and the Universal oligonucleotide tail-adaptor can be amplified, (i.e. copied).

In the next step (i.e. step (c)) of the method described herein, a portion of the amplified portion resulting from step (b) is amplified in a second amplification step. The second amplification step can be a set of PCR amplification cycles using a second target-specific primer and a first sequencing primer. The second set of PCR amplification cycles can have PCR parameters identical to, or which differ from, those of the first set of PCR amplification cycles. E.g. the PCR amplification regimens of steps (b) and (c) can have the same or different annealing temperatures or the same or different extension step time lengths.

The methods described herein allow for determining the nucleotide sequence contiguous to a known target nucleotide sequence on either or both flanks of the known target nucleotide sequence. Regardless of whether the target nucleic acid normally exists as a single-stranded or double-stranded nucleic acid, sequence information is typically represented in a single-stranded format (Strand A), from 5' to 3'. If the sequence 5' of the known target nucleotide sequence of Strand A is to be determined, the gene-specific primers can be complementary (i.e. anneal to) Strand A. If the sequence 3' of the known target nucleotide sequence of Strand A is to be determined, the gene-specific primers can be identical to Strand A, such that they will anneal to the complementary strand of a double-stranded target nucleic acid. Such considerations of primer design are well known to those of ordinary skill in the art.

In some embodiments, the methods described herein, relating to the use of a first and second gene-specific primer can result in assays with a superior on-target rate, e.g. 70-90%. In some embodiments, the assays and methods described herein can have a target specificity rate of at least 85%.

In some embodiments, the four types of primers are designed such that they will specifically anneal to their complementary sequences at an annealing temperature of from about 61 to 72° C., e.g. from about 61 to 69° C., from about 63 to 69° C., from about 63 to 67° C., from about 64 to 66° C. In some embodiments, the four types of primers are designed such that they will specifically anneal to their complementary sequences at an annealing temperature of less than 72° C. In some embodiments, the four types of primers are designed such that they will specifically anneal to their complementary sequences at an annealing temperature of less than 70° C. In some embodiments, the four types of primers are designed such that they will specifically anneal to their complementary sequences at an annealing temperature of less than 68° C. In some embodiments, the four types of primers are designed such that they will specifically anneal to their complementary sequences at an annealing temperature of about 65° C.

In some embodiments, the portions of the target-specific primers that specifically anneal to the known target nucleotide sequence will anneal specifically at a temperature of about 61 to 72° C., e.g. from about 61 to 69° C., from about 63 to 69° C., from about 63 to 67° C., from about 64 to 66° C. In some embodiments, the portions of the target-specific primers that specifically anneal to the known target nucleotide sequence will anneal specifically at a temperature of about 65° C. in a PCR buffer.

In some embodiments, the primers and/or adaptors described herein can not comprise modified bases (e.g. the primers and/or adaptors can not comprise a blocking 3' amine).

In the next step (i.e. step (d)) of the methods described herein, the amplified portion resulting from step (c) can be sequenced. In some embodiments, the sequencing can be performed by a next-generation sequencing method. As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing™ (Lynx Therapeutics); 454 Pyro-Sequencing™ (454 Life Sciences/Roche Diagnostics); solid-phase, reversible dye-terminator sequencing (Solexa/Illumina): SOLiD™ technology (Applied Biosystems); Ion semiconductor sequencing (ION Torrent™); DNA nanoball sequencing (Complete Genomics); and technologies available from Pacific Biosciences, Intelligen Bio-systems, Oxford Nanopore Technologies, and Helicos Biosciences. In some embodiments, the sequencing primers can comprise portions compatible with the selected next-generation sequencing method. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties).

In some embodiments, the sequencing step relies upon the use of a first and second sequencing primers. In some embodiments, the first and second sequencing primers are selected to be compatible with a next-generation sequencing method as described herein.

Methods of aligning sequencing reads to known sequence databases of genomic and/or cDNA sequences are well known in the art and software is commercially available for this process. In some embodiments, reads (less the sequencing primer and/or adaptor nucleotide sequence) which do not map, in their entirety, to wild-type sequence databases can be genomic rearrangements or large indel mutations. In some embodiments, reads (less the sequencing primer and/or adaptor nucleotide sequence) comprising sequences which map to multiple locations in the genome can be genomic rearrangements.

In some embodiments, target nucleic acids and/or amplification products thereof can be isolated from enzymes, primers, or buffer components before and/or after any of steps a-d. Methods for isolating nucleic acids are well known in the art. In some embodiments, the isolation can comprise Solid Phase Reversible Immobilization (SPRI) cleanup. Methods for SPRI cleanup are well known in the art and kits are commercially available, e.g. Agencourt AMPure XP™-PCR Purification (Cat No. A63880, Beckman Coulter; Brea, Calif.). In some embodiments, enzymes can be inactivated by heat treatment.

In some embodiments, the target nucleic acid can be comprised by genomic DNA. In some embodiments, the target nucleic acid can be comprised by ribonucleic acid (RNA), e.g. mRNA. In some embodiments, the target nucleic acid can be comprised by cDNA. Many of the sequencing methods suitable for use in the methods described herein provide sequencing runs with optimal read lengths of tens to hundreds of nucleotide bases (e.g. Ion Torrent™ technology can produce read lengths of 200-400 bp). Target nucleic acids comprised, for example, by genomic DNA or mRNA, can be comprised by nucleic acid molecules which are substantially longer than this optimal read length. In order for the amplified nucleic acid portion resulting from step (c) to be of a suitable length for use in a particular sequencing technology, the average distance between the known target nucleotide sequence and an end of the target nucleic acid to which the Universal oligonucleotide tail-adaptor can be ligated should be as close to the optimal read length of the selected technology as possible. For example, if the optimal read-length of a given sequencing technology is 200 bp, then the nucleic acid molecules amplified in accordance with the methods described herein should have an average length of about 400 bp or less. Target nucleic acids comprised by, e.g., genomic DNA or mRNA, can be sheared, e.g. mechanically or enzymatically sheared, to generate fragments of any desired size prior to step (a). Non-limiting examples of mechanical shearing processes include sonication, nebulization, and AFA™ shearing technology available from Covaris (Woburn, Mass.). In some embodiments, a target nucleic acid comprised by genomic DNA can be mechanically sheared by sonication. In some embodiments, when the target nucleic acid is comprised by RNA, the sample can be subjected to a reverse transcriptase regimen to generate DNA template and the DNA template can then be sheared. In some embodiments, target RNA can be sheared before performing the reverse transcriptase regimen. In some embodiments, a sample comprising target RNA can be used in the methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers; and by subjecting the nucleic acid to end-repair, phosphorylation, and adenylation in a single tube.

In some embodiments, the known target nucleotide sequence can be comprised by a gene rearrangement. The methods described herein are suited for determining the presence and/or identity of a gene rearrangement as the identity of only one half of the gene rearrangement must be previously known (i.e. the half of the gene rearrangement which is to be targeted by the gene-specific primers). In some embodiments, the gene rearrangement can comprise an oncogene. In some embodiments, the gene rearrangement can comprise a fusion oncogene.

In some embodiments, the target nucleic acid can be comprised by a sample. In some embodiments, the target nucleic acid can be comprised by a sample obtained from a subject. In some embodiments a sample can be a diagnostic sample obtained from a subject. In some embodiments, a sample can further comprise proteins, cells, fluids, biological fluids, preservatives, and/or other substances. By way of non-limiting example, a sample can be a cheek swab, blood, serum, plasma, sputum, cerebROS1pinal fluid, urine, tears, alveolar isolates, pleural fluid, pericardial fluid, cyst fluid, tumor tissue, tissue, a biopsy, saliva, an aspirate, or combinations thereof. In some embodiments, a sample can be obtained by resection or biopsy.

In some embodiments, the sample can be obtained from a subject in need of treatment for cancer. In some embodiments, the sample can comprise a population of tumor cells, e.g. at least one tumor cell. In some embodiments, the sample can comprise a tumor biopsy, including but not limited to, untreated biopsy tissue or treated biopsy tissue (e.g. formalin-fixed and/or paraffin-embedded biopsy tissue).

In some embodiments, the sample can be freshly collected. In some embodiments, the sample can be stored prior to being used in the methods and compositions described herein. In some embodiments, the sample is an untreated sample. As used herein, "untreated sample" refers to a biological sample that has not had any prior sample pre-treatment except for dilution and/or suspension in a solution. In some embodiments, a sample can be obtained from a subject and preserved or processed prior to being utilized in the methods and compositions described herein. By way of non-limiting example, a sample can be embedded in paraffin wax, refrigerated, or frozen. A frozen sample can be thawed before determining the presence of a nucleic acid according to the methods and compositions described herein. In some embodiments, the sample can be a processed or treated sample. Exemplary methods for treating or processing a sample include, but are not limited to, centrifugation, filtration, sonication, homogenization, heating, freezing and thawing, contacting with a preservative (e.g. anti-coagulant or nuclease inhibitor) and any combination thereof. In some embodiments, the sample can be treated with a chemical and/or biological reagent. Chemical and/or biological reagents can be employed to protect and/or maintain the stability of the sample or nucleic acid comprised by the sample during processing and/or storage. In addition, or alternatively, chemical and/or biological reagents can be employed to release nucleic acids from other components of the sample. By way of non-limiting example, a blood sample can be treated with an anti-coagulant prior to being utilized in the methods and compositions described herein. The skilled artisan is well aware of methods and processes for processing, preservation, or treatment of samples for nucleic acid analysis. In some embodiments, the sample can be a clarified fluid sample, for example, by centrifugation. In some embodiments, the sample can be clarified by low-speed centrifugation (e.g. 3,000×g or less) and collection of the supernatant comprising the clarified fluid sample.

In some embodiments, the nucleic acid present in a sample can be isolated, enriched, or purified prior to being utilized in the methods and compositions described herein. Methods of isolating, enriching, or purifying nucleic acids from a sample are well known to one of ordinary skill in the art. By way of non-limiting example, kits for isolation of genomic DNA from various sample types are commercially available (e.g. Catalog Nos. 51104, 51304, 56504, and 56404; Qiagen; Germantown, Md.).

The methods described herein can be used in multiplex techniques. In embodiments of the methods described herein, multiplex applications can include determining the nucleotide sequence contiguous to one or more known target nucleotide sequences. As used herein, "multiplex PCR" refers to a variant of PCR where simultaneous amplification of more than one target nucleic acid in one reaction vessel and subsequent determination of the sequence of the amplification products by using more than one set of first and second gene-specific primers. Multiplex can refer to the detection of between about 2-1,000 different target sequences in a single reaction. As used herein, multiplex refers to the detection of any range between 2-1,000, e.g., between 5-500, 25-1000, or 10-100 different target sequences in a single reaction, etc. The term "multiplex" as applied to PCR implies that there are primers specific for at least two different target sequences in the same PCR reaction.

In some embodiments, the target nucleic acids in a sample, or separate portions of a sample, can be amplified with a plurality of first and second target-specific primers. In some embodiments, the plurality of first and second target-specific primers can be present in a single reaction mixture, e.g. multiple amplification products can be produced in the same reaction mixture. In some embodiments, the plurality of sets of first and second target-specific primers can specifically anneal to known target sequences comprised by separate genes. In some embodiments, at least two sets of first and second target-specific primers can specifically anneal to different portions of a known target sequence. In some embodiments, at least two sets of first and second target-specific primers can specifically anneal to different portions of a known target sequence comprised by a single gene. In some embodiments, at least two sets of first and second target-specific primers can specifically anneal to different exons of a gene comprising a known target sequence. In some embodiments, the plurality of first target-specific primers can comprise identical 5' tag sequence portions.

In embodiments of the methods described herein, multiplex applications can include determining the nucleotide sequence contiguous to one or more known target nucleotide sequences in multiple samples in one sequencing reaction or sequencing run. The multiple samples can be of different origins, e.g. from different tissues and/or different subjects. In such embodiments, the universal oligonucleotide tail-adaptor can further comprise a barcode portion. In some embodiments, a universal oligonucleotide tail-adaptor with a unique barcode portion can be added to each sample and ligated to the nucleic acids therein; the samples can then be pooled after step (a). Each resulting sequencing read of an amplification product will therefor comprise a barcode identifying which sample comprised the original template nucleic acid from which the amplification product is derived. The use of barcode portions in next-generation sequencing applications is well known in the art and described, for example, in Margulies, M. et al. "Genome Sequencing in Microfabricated High-Density Picolitre Reactors", Nature, 437, 376-80 (2005); Mikkelsen, T. et al. "Genome-Wide Maps of Chromatin State in Pluripotent and Lineage-Committed Cells", Nature, 448, 553-60 (2007); McLaughlin, S. et al. "Whole-Genome Resequencing With Short Reads: Accurate Mutation Discovery With Mate Pairs and Quality Values", ASHG Annual Meeting (2007); Shendure I. et al. "Accurate Multiplex Polony Sequencing of an Evolved Bacterial Genome", Science, 309, 1728-32 (2005); Harris, T. et al. "Single-Molecule DNA Sequencing of a Viral Genome", Science, 320, 106-9 (2008); Simen, B. et al. "Prevalence of LoW Abundance Drug Resistant Variants by Ultra Deep Sequencing in Chronically HIV-infected Antiretroviral (ARV) Naive Patients and the Impact on Virologic Outcomes", 16th International HIV Drug Resistance Workshop, Barbados (2007); Thomas, R. et al. "Sensitive Mutation Detection in Heterogeneous Cancer Specimens by Massively Parallel Picoliter Reactor Sequencing", Nature Med., 12, 852-855 (2006); Mitsuya, Y et al. "Minority Human Immunodeficiency Virus Type 1 Variants in Antiretroviral-Naive Persons With Reverse Transcriptase Codon 215 Revertant Mutations", I. Vir., 82, 10747-10755 (2008); Binladen, J. et al. "The Use of Coded PCR Primers Enables High-Throughput Sequencing of Multiple Homolog Amplification Products by 454 Parallel Sequencing", PLoS ONE, 2, e197 (2007); and Hoffmann, C. et al. "DNA Bar Coding and PyROS1equencing to Identify Rare HIV Drug Resistance Mutations", Nuc. Acids Res., 35, e91 (2007), all of which are herein incorporated by reference.

In some embodiments of the technology described herein, determining the sequence contiguous to a known oligonucleotide target sequence can provide information relevant to treatment of disease, and/or can be comprised by a method of treating disease. In some embodiments, the sample can be from a subject in need of treatment for a disease associated with a genetic alteration. In some embodiments, the known oligonucleotide target sequence can be comprised by a disease-associated gene, e.g. an oncogene. In some embodiments, the sequence contiguous to a known oligonucleotide target sequence and/or the known oligonucleotide target sequence can comprise a mutation or genetic abnormality which is disease-associated, e.g. a SNP, an insertion, a deletion, and/or a gene rearrangement. In some embodiments, the sequence contiguous to a known oligonucleotide target sequence and/or the known oligonucleotide target sequence present in a sample can be comprised by a gene rearrangement product. In some embodiments, the gene rearrangement can be an oncogene, e.g. a fusion oncogene.

Certain treatments for cancer are particularly effective against tumors comprising certain oncogenes, e.g. a treatment agent which targets the action or expression of a given fusion oncogene can be effective against tumors comprising that fusion oncogene but not against tumors lacking the fusion oncogene. The methods described herein can allow the determination of specific sequences which reveal oncogene status (e.g. mutations, SNPs, and/or rearrangements). As described herein, the methods described herein can further allow the determination of specific sequences when the sequence of only one flank is known, e.g. the methods described herein can determine the presence and identity of gene rearrangements involving known oncogenes where the precise location and/or rearrangement partner are not known before the methods described herein are performed.

In some embodiments, the technology described herein relates to a method of treating cancer, the method comprising; detecting, in a tumor sample obtained from a subject in need of treatment for cancer, the presence of one or more oncogene rearrangements according to the method described herein; administering a cancer treatment which is effective against tumors having any of the detected oncogene rearrangements. In some embodiments, the technology described herein relates to a method of determining if a subject in need of treatment for cancer will be responsive to a given treatment, the method comprising; detecting, in a tumor sample obtained from the subject, the presence of an oncogene rearrangement according to the method as described herein; wherein the subject is determined to be responsive to a treatment targeting an oncogene rearrangement product if the presence of the oncogene rearrangement is detected.

In some embodiments, e.g. when the sample is obtained from a subject in need of treatment for lung cancer, the known oligonucleotide target sequence can comprise sequence from a gene selected from the group of ALK; ROS1; and RET. Gene rearrangements involving the ALK, ROS1, and RET genes and which result in fusion oncogenes are well known in the art (see, e.g. Soda et al. Nature 2007 448561-6: Rikova et al. Cell 2007 131:1190-1203; Kohno et al. Nature Medicine 2012 18:375-7; Takouchi et al. Nature Medicine 2012 18:378-81; which are incorporated by reference herein in their entireties. However, the precise location of the gene rearrangement (e.g. where in the ALK, ROS1, and/or RET gene the rearrangement has occurred), and the identity of the second gene involved in the rearrangement can vary. In the methods described herein, the presence and identity of such a rearrangement can be detected without having to know the location of the rearrangement or the identity of the second gene involved in the gene rearrangement.

In some embodiments, the known target sequence can comprise sequence from a gene selected from the group of: ALK; ROS1; and RET. In some embodiments, at least one set of a first target-specific primer and a second target-specific primer can be selected from the group consisting of; SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; SEQ ID NOs: 21 and 22; SEQ ID NOs: 23 and 24; SEQ ID NOs: 25 and 26; SEQ ID NOs: 27 and 28; SEQ ID NOs: 29 and 30; SEQ ID NOs: 31 and 32; SEQ ID NOs: 33 and 34; SEQ ID NOs: 35 and 36; and SEQ ID NOs: 37 and 38.

In some embodiments, the presence of a gene rearrangement of ALK in a sample obtained from a tumor in a subject can indicate that the tumor is susceptible to treatment with a treatment selected from the group consisting of: an ALK inhibitor; crizotinib (PF-02341066); AP26113; LDK378; 3-39; AF802; IPI-504; ASP3026; AP-26113; X-396; GSK-1838705A; CH5424802; diamino and aminopyrimidine inhibitors of ALK kinase activity such as NVP-TAE684 and PF-02341066 (see, e.g. Galkin et al, Proc Natl Acad Sci USA, 2007, 104:270-275; Zou et al. Cancer Res, 2007, 67:4408-4417; Hallberg and Palmer F1000 Med Reports 2011 3:21; and Sakamoto et al. Cancer Cell 2011 19:679-690) and molecules disclosed in WO 04/079326. All of the foregoing references are incorporated by reference herein in their entireties. An ALK inhibitor can include any agent that reduces the expression and/or kinase activity of ALK or a portion thereof, including, e.g. oligonucleotides, small molecules, and/or peptides that reduce the expression and/or activity of ALK or a portion thereof. As used herein "anaplastic lymphoma kinase" or "ALK" refers to a transmembrane tyROS1ine kinase typically involved in neuronal regulation in the wildtype form. The nucleotide sequence of the ALK gene and mRNA are known for a number of species, including human (e.g. SEQ ID NO: 2 (mRNA), NCBI Gene ID: 238).

In some embodiments, the presence of a gene rearrangement of ROS1 in a sample obtained from a tumor in a subject can indicate that the tumor is susceptible to treatment with a treatment selected from the group consisting of: a ROS1 inhibitor and an ALK inhibitor as described herein above (e.g. crizotinib). A ROS1 inhibitor can include any agent that reduces the expression and/or kinase activity of ROS1 or a portion thereof, including, e.g. oligonucleotides, small molecules, and/or peptides that reduce the expression and/or activity of ROS1 or a portion thereof. As used herein "c-ROS1 oncogene 1" or "ROS1" (also referred to in the art as ROS1-1) refers to a transmembrane tyROS1ine kinase of the sevenless subfamily and which interacts with PTPN6. The nucleotide sequence of the ROS1 gene and mRNA are known for a number of species, including human (e.g. SEQ ID NO: 1 (mRNA), NCBI Gene ID: 238).

In some embodiments, the presence of a gene rearrangement of RET in a sample obtained from a tumor in a subject can indicate that the tumor is susceptible to treatment with a treatment selected from the group consisting of: a RET inhibitor; DP-2490, DP-3636, SU5416; BAY 43-9006, BAY 73-4506 (regorafenib), ZD6474, NVP-AST487, sorafenib, RPM, XL184, vandetanib, sunitinib, imatinib, pazopanib, axitinib, motesanib, gefitinib, and withaferin A (see, e.g. Samadi et al. Surgery 2010 148:1228-36; Cuccuru et al. JNCI 2004 13:1006-1014; Akeno-Stuart et al. Cancer Research 2007 67:6956; Grazma et al. J Clin Oncol 2010 28:15s 5559; Mologni et al. J Mol Endocrinol 2006 37:199-212; Calmomagno et al. Journal NCI 2006 98:326-334; Mologni. Curr Med Chem 2011 18:162-175 and the compounds disclosed in WO 06/034833; US Patent Publication 2011/0201598 and U.S. Pat. No. 8,067,434). All of the foregoing references are incorporated by reference herein in their entireties. A RET inhibitor can include any agent that reduces the expression and/or kinase activity of RET or a portion thereof, including, e.g. oligonucleotides, small molecules, and/or peptides that reduce the expression and/or activity of RET or a portion thereof. As used herein "rearranged during transfection" or "RET" refers to a receptor tyROS1ine kinase of the cadherein superfamily which is involved in neural crest development and recognizes glial cell line-derived neurotrophic factor family signaling molecules. The nucleotide sequence of the ROS1 gene and mRNA are known for a number of species, including human (e.g. SEQ ID NOs: 3-4 (mRNA), NCBI Gene ID: 5979).

Further non-limiting examples of applications of the methods described herein include detection of hematological malignancy markers and panels thereof (e.g. including those to detect genomic rearrangements in lymphomas and leukemias), detection of sarcoma-related genomic rearrangements and panels thereof; and detection of IGH/TCR gene rearrangements and panels thereof for lymphoma testing.

In some embodiments, the methods described herein relate to treating a subject having or diagnosed as having, e.g. cancer with a treatment for cancer. Subjects having cancer can be identified by a physician using current methods of diagnosing cancer. For example, symptoms and/or complications of lung cancer which characterize these conditions and aid in diagnosis are well known in the art and include but are not limited to, weak breathing, swollen lymph nodes above the collarbone, abnormal sounds in the lungs, dullness when the chest is tapped, and chest pain. Tests that may aid in a diagnosis of, e.g. lung cancer include, but are not limited to, x-rays, blood tests for high levels of certain substances (e.g. calcium), CT scans, and tumor biopsy. A family history of lung cancer, or exposure to risk factors for lung cancer (e.g. smoking or exposure to smoke and/or air pollution) can also aid in determining if a subject is likely to have lung cancer or in making a diagnosis of lung cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chromic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS1tate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors. In some embodiments, the cancer can be lung cancer.

In some embodiments, the methods described herein comprise administering an effective amount of compositions described herein, e.g. a treatment for cancer to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aeROS1ol), pulmonary, cutaneous, topical, injection, or intratumoral administration. Administration can be local or systemic. The term "effective amount" as used herein refers to the amount of a treatment needed to alleviate at least one or more symptom of the disease or disorder, and relates to a sufficient amount of pharmacological composition to provide the desired effect. The term "therapeutically effective amount" therefore refers to an amount that is sufficient to effect a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation. The effects of any particular dosage can be monitored by a suitable bioassay. The dosage can be determined by a physician and adjusted, as necessary, to suit observed effects of the treatment.

Non-limiting examples of a treatment for cancer can include radiation therapy, surgery, gemcitabine, cisplastin, paclitaxel, carboplatin, bortezomib, AMG479, vorinostat, rituximab, temozolomide, rapamycin, ABT-737, P1-103; alkylating agents such as thiotepa and CYTOXAN® cyclosphosphamide; alkyl sulfonates such as busulfan, impROS1ulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitROS1ureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX®); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

In some embodiments, the methods described herein can be applicable for resequencing, e.g. for confirming particularly relevant, low-quality, and/or complex sequences obtained by non-directed sequencing of a large amount of nucleic acids. By way of non-limiting examples, the methods described herein can allow the directed and/or targeted resequencing of targeted disease gene panels (e.g. 10-100 genes), resequencing to confirm variants obtained in large scale sequencing projects, whole exome resequencing, and/or targeted resequencing for detection of single nucleotide variants, multiple nucleotide variants, insertions, deletions, copy number changes, and methylation status.

In some embodiments, the methods described herein can allow microbiota sequencing, ancient sample sequencing, and/or new variant virus genotyping.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of determining the nucleotide sequence contiguous to a known target nucleotide sequence, the method comprising;
   (a) ligating a target nucleic acid comprising the known target nucleotide sequence with a universal oligonucleotide tail-adaptor;
   (b) amplifying a portion of the target nucleic acid and the amplification strand of the universal oligonucleotide tail-adaptor with a first adaptor primer and a first target-specific primer;
   (c) amplifying a portion of the amplicon resulting from step (b) with a second adaptor primer and a second target-specific primer;
   (d) sequencing the amplified portion from step (c) using a first and second sequencing primer;
   wherein the universal oligonucleotide tail-adaptor comprises a first ligatable duplex end and a second unpaired end;
   wherein the universal oligonucleotide tail-adaptor comprises a blocking strand and an amplification strand;
     wherein the blocking strand comprises a 5' duplex portion;
     wherein the amplification strand comprises an unpaired 5' portion, a 3' duplex portion, and a 3' T overhang;
       wherein the amplification strand comprises nucleic acid sequences identical to a first and second sequencing primers;
       wherein the duplex portions of the blocking strand and the amplification strand are substantially complementary and form the first ligatable duplex end comprising a 3' T overhang;
         wherein the duplex portion is of sufficient length to remain in duplex form at the ligation temperature;
   wherein the first target-specific primer comprises a nucleic acid sequence that can specifically anneal to the known target nucleotide sequence of the target nucleic acid at the annealing temperature;
   wherein the second target-specific primer comprises a 3' portion comprising a nucleic acid sequence that can specifically anneal to a portion of the known target nucleotide sequence comprised by the amplicon resulting from step (b), and a 5' portion comprising a nucleic acid sequence that is identical to a second sequencing primer and the second target-specific primer is nested with respect to the first target-specific primer;
   wherein the first adaptor primer comprises a nucleic acid sequence identical to a 5' portion of the first sequencing primer; and
   wherein the second adaptor primer comprises a nucleic acid sequence identical to a portion of the first sequencing primer and is nested with respect to the first adaptor primer.

2. The method of paragraph 1, wherein the blocking strand of the universal oligonucleotide tail-adaptor further comprises a 3' unpaired portion which is not substantially complementary to the 5' unpaired portion of the amplification strand; and
   wherein the 3' unpaired portion of the blocking strand is not substantially complementary to or substantially identical to any of the primers.

3. The method of any of paragraphs 1-2, wherein the second adaptor primer is nested with respect to the first adaptor primer by at least 3 nucleotides.

4. The method of any of paragraphs 1-3, wherein the portion of the amplification strand that comprises a nucleic acid sequence identical to a first and second sequencing primers is comprised, at least in part, by the 5' unpaired portion of the amplification strand.

5. The method of any of paragraphs 1-4, wherein the first target-specific primer further comprises a 5' tag sequence portion comprising a nucleic acid sequence of high GC content which is not substantially complementary to or substantially identical to any other portion of any of the primers.

6. The method of any of paragraphs 1-5, wherein the second adaptor primer is identical to the full-length first sequencing primer.

7. The method of any of paragraphs 1-6, wherein the portions of the target-specific primers that specifically anneal to the known target will anneal specifically at a temperature of about 65° C. in a PCR buffer.

8. The method of any of paragraphs 1-7, wherein the method further comprises; prior to step (a), the steps of:
   mechanically shearing the nucleic acid;
   subjecting the nucleic acid to end-repair;
   subjecting the nucleic acid to phosphorylation;
   and subjecting the nucleic acid to adenylation.

9. The method of any of paragraphs 1-8, wherein the sample comprises genomic DNA.

10. The method of any of paragraphs 1-9, wherein the sample comprises RNA and the method further comprises a first step of subjecting the sample to a reverse transcriptase regimen.

11. The method of any of paragraphs 1-10, wherein the reverse transcriptase regimen comprises the use of random hexamers.

12. The method of any of paragraphs 1-11, wherein the known target sequence is comprised by a gene rearrangement.

13. The method of paragraph 12 wherein the gene rearrangement is present in a nucleic acid selected from the group consisting of:
   genomic DNA; RNA; and cDNA.

14. The method of any of paragraphs 12-13, wherein the gene rearrangement comprises an oncogene.

15. The method of paragraph 14, wherein the gene rearrangement comprises a fusion oncogene.
16. The method of any of paragraphs 1-15, wherein the nucleic acid product is sequenced by a next-generation sequencing method.
17. The method of paragraph 16, wherein the next-generation sequencing method comprises a method selected from the group consisting of:
Ion Torrent™, Illumina, SOLiD™, 454™; Massively Parallel Signature Sequencing™ solid-phase, reversible dye-terminator sequencing; and DNA nanoball sequencing.
18. The method of any of paragraphs 1-17, wherein the first and second sequencing primers are compatible with the selected next-generation sequencing method.
19. The method of any of paragraphs 1-18, wherein the method comprises contacting the sample, or separate portions of the sample, with a plurality of sets of first and second target-specific primers.
20. The method of any of paragraphs 1-19, wherein the method comprises contacting a single reaction mixture comprising the sample with a plurality of sets of first and second target-specific primers.
21. The method of any of paragraphs 1-20, wherein the plurality of sets of first and second target-specific primers specifically anneal to known target nucleotide sequences comprised by separate genes.
22. The method of any of paragraphs 1-21, wherein at least two sets of first and second target-specific primers specifically anneal to different portions of a known target nucleotide sequence.
23. The method of any of paragraphs 1-22, wherein at least two sets of first and second target-specific primers specifically anneal to different portions of a single gene comprising a known target nucleotide sequence.
24. The method of any of paragraphs 1-23, wherein at least two sets of first and second target-specific primers specifically anneal to different exons of a gene comprising a known nucleotide target sequence.
25. The method of any of paragraphs 19-24, wherein the plurality of first target-specific primers comprise identical 5' tag sequence portions.
26. The method of any of paragraphs 1-25, wherein the universal oligonucleotide tail-adaptor further comprises a barcode portion.
27. The method of paragraph 26, wherein multiple samples are each contacted with a universal oligonucleotide tail-adaptor with a unique barcode portion and wherein the samples are pooled after step (a).
28. The method of any of paragraphs 1-27, wherein each amplification step comprises a set of cycles of a PCR amplification regimen from 5 cycles to 20 cycles in length.
29. The method of any of paragraphs 1-28, wherein the target-specific primers and the adaptor primers are designed such that they will specifically anneal to their complementary sequences at an annealing temperature of from about 61 to 72° C.
30. The method of any of paragraphs 1-29, wherein the target-specific primers and the adaptor primers are designed such that they will specifically anneal to their complementary sequences at an annealing temperature of about 65° C.
31. The method of any of paragraphs 1-30, wherein the sample comprises a biological sample obtained from a subject.
32. The method of any of paragraphs 1-31, wherein the sample is obtained from a subject in need of treatment for a disease associated with a genetic alteration.
33. The method of paragraph 32, wherein the disease is cancer.
34. The method of any of paragraphs 1-33, wherein the sample comprises a population of tumor cells.
35. The method of any of paragraphs 1-34, wherein the sample comprises a tumor biopsy.
36. The method of any of paragraphs 1-35, wherein the cancer is lung cancer.
37. The method of any of paragraphs 1-36, wherein the known target sequence is comprised by a disease-associated gene.
38. The method of any of paragraphs 1-37, wherein the known target sequence is comprised by a gene rearrangement product in the sample.
39. The method of any of paragraphs 1-38, wherein gene rearrangement product is an oncogene.
40. The method of any of paragraphs 1-39, wherein the known target sequence comprises sequence from a gene selected from the group of:
ALK; ROS1; and RET.
41. The method of paragraph 40, wherein at least one set of a first target-specific primer and a second target-specific primer are selected from the group consisting of;
SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; SEQ ID NOs: 21 and 22; SEQ ID NOs: 23 and 24; SEQ ID NOs: 25 and 26; SEQ ID NOs: 27 and 28; SEQ ID NOs: 29 and 30; SEQ ID NOs: 31 and 32; SEQ ID NOs: 33 and 34; SEQ ID NOs: 35 and 36; and SEQ ID NOs: 37 and 38.
42. The method of any of paragraphs 40-41, wherein the presence of a gene rearrangement of ALK in a sample obtained from a tumor in a subject indicates that the tumor is susceptible to treatment with a treatment selected from the group consisting of:
an ALK inhibitor; crizotinib (PF-02341066); AP26113; LDK378; 3-39; AF802; IPI-504; ASP3026; AP-26113; X-396; GSK-1838705A; CH5424802; and NVP-TAE684.
43. The method of any of paragraphs 40-41, wherein the presence of a gene rearrangement of ROS1 in a sample obtained from a tumor in a subject indicates that the tumor is susceptible to treatment with a treatment selected from the group consisting of:
a ROS inhibitor; an ALK inhibitor; crizotinib (PF-02341066); AP26113; LDK378; 3-39; AF802; IPI-504; ASP3026; AP-26113; X-396; GSK-1838705A; CH5424802; and NVP-TAE684.
44. The method of any of paragraphs 40-41, wherein the presence of a gene rearrangement of RET in a sample obtained from a tumor in a subject indicates that the tumor is susceptible to treatment with a treatment selected from the group consisting of:
a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A.
45. A method of treating cancer, the method comprising; detecting, in a tumor sample obtained from a subject in need of treatment for cancer, the presence of one or more oncogene rearrangements according to the method of any of paragraphs 1-44;
administering a cancer treatment which is effective against tumors having any of the detected oncogene rearrangements.
46. The method of paragraph 45, wherein a treatment selected from the group consisting of:
an ALK inhibitor; crizotinib (PF-02341066); AP26113; LDK378; 3-39; AF802; IPI-504; ASP3026; AP-26113; X-396; GSK-1838705A; CH5424802; and NVP-TAE684;
is effective against tumors having an ALK oncogene rearrangement.
47. The method of paragraph 45, wherein a treatment selected from the group consisting of:
a ROS1 inhibitor; an ALK inhibitor; crizotinib (PF-02341066); AP26113; LDK378; 3-39; AF802; IPI-504; ASP3026; AP-26113; X-396; GSK-1838705A; CH5424802; and NVP-TAE684;
is effective against tumors having an ROS1 oncogene rearrangement.
48. The method of paragraph 45, wherein a treatment selected from the group consisting of:
a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A;
is effective against tumors having an RET oncogene rearrangement.
49. A method of determining if a subject in need of treatment for cancer will be responsive to a given treatment, the method comprising;
detecting, in a tumor sample obtained from the subject, the presence of an oncogene rearrangement according to the method of any of paragraphs 1-44;
wherein the subject is determined to be responsive to a treatment targeting an oncogene rearrangement product if the presence of the oncogene rearrangement is detected.
50. The method of paragraph 49, wherein if the presence of an ALK oncogene rearrangement is detected, the subject will be responsive to a treatment selected from the group consisting of:
an ALK inhibitor; crizotinib (PF-02341066); AP26113; LDK378; 3-39; AF802; IPI-504; ASP3026; AP-26113; X-396; GSK-1838705A; CH5424802; and NVP-TAE684.
51. The method of paragraph 49, wherein if the presence of an ROS1 oncogene rearrangement is detected, the subject will be responsive to a treatment selected from the group consisting of:
an ALK inhibitor; crizotinib (PF-02341066); AP26113; LDK378; 3-39; AF802; IPI-504; ASP3026; AP-26113; X-396; GSK-1838705A; CH5424802; and NVP-TAE684.
52. The method of paragraph 49, wherein if the presence of an RET oncogene rearrangement is detected, the subject will be responsive to a treatment selected from the group consisting of:
a RET inhibitor; DP-2490; DP-3636; SU5416; BAY 43-9006; BAY 73-4506 (regorafenib); ZD6474; NVP-AST487; sorafenib; RPI-1; XL184; vandetanib; sunitinib; imatinib; pazopanib; axitinib; motesanib; gefitinib; and withaferin A.
53. The method of any of paragraphs 44-52, wherein the cancer is lung cancer.

EXAMPLES

Example 1

In one embodiment, described herein is an assay using a novel half-truncated "Y" shape adapter for next generation sequencing library construction followed by two single-end nested polymerase chain reactions enables rapid and efficient target enrichment using RNA or genomic DNA as template from fresh or formalin-fixed and paraffin-embedded (FFPE) specimens. This enrichment method enables targeted resequencing of cDNA or gDNA for potential detection of genetic alterations (single nucleotide variants, insertions/deletions, and copy number), epigenetic alterations (methylation), gene expression, and genomic rearrangements.

Target enrichment prior to next-generation sequencing is more cost-effective than whole genome, whole exome, and whole transcriptome sequencing and therefore more practical for broad implementation both for research discovery and clinical applications. High coverage depth afforded by target enrichment approaches enables wider dynamic range for allele counting (in gene expression and copy number assessment) and detection of low frequency mutations, a critical feature for evaluating somatic mutations in cancer. Before broad implementation of whole genome or whole exome sequencing is possible, the mainstay of clinical next generation sequencing will involve select disease panels with a discrete number of gene targets. Likewise, research studies for analysis of large sample sizes based on defined gene targets will also require an economical means for genotyping. The assays described herein would be applicable in both of these settings.

For the detection of inter and intra-chromosomal rearrangements, whole genome or transcriptome sequencing is useful for novel discovery of genomic rearrangements and does not require prior knowledge of the involved gene/chromosomal partners. However, these whole genome and transcriptome approaches are not practical currently in the clinical setting due to high cost, low sequencing depth resulting in poor sensitivity, and highly demanding bioinformatics analysis. Fluorescence in situ hybridization (FISH) has been the gold standard assay for the detection of genomic rearrangements in clinics; however, the assay is low-throughput and its implementation requires special equipment and expert knowledge/experience. RT-PCR is also effective at detecting such rearrangements but requires knowledge of both the 5' and 3' partners and is not scalable for a large number of targets/samples.

Examples of commonly used preparatory enrichment assays for next generation sequencing include hybridization-based capture assays (TruSeq Capture™, Illumina; SureSelect Hybrid Capture™, Agilent) and polymerase chain reaction (PCR)-based assays (HaloPlex™ Agilent; AmpliSeq™, Ion Torrent™; TruSeq Amplicon™, Illumina; emulsion/digital PCR, Raindance). Hybridization-based approaches capture not only the targeted sequences covered by the capture probes but also near off-target bases that consume additional sequencing capacity. In addition, these methods are relatively time-consuming, labor-intensive, and less specific. A PCR amplification based approach is simpler and faster but by conventional design requires both forward and reverse primers flanking target loci. In particular for detection of genomic rearrangements with unknown fusion partners, PCR is not applicable.

Described herein is a target enrichment assay using a novel half-truncated "Y" shape adapter for next generation sequencing library construction, enabling rapid sequencing of cDNA or gDNA from fresh or FFPE specimens. FIG. 1 outlines the library construction for target enrichment using a half-truncated Y adapter for Ion Torrent™ sequencing as an example. Importantly, this method is adaptable for any other next generation sequencing platform, including but not limited to Illumina, SOLiD™, and 454™. In short a randomly sheared, double-stranded cDNA or gDNA template can be end-repaired, adenylated, and then ligated on one or both ends with the universal Y adapter to create a universal sequence for initiating PCR and subsequent sequencing. An initial round of PCR using a target specific primer tagged with a stuffer tail (the stuff tail aids in multiplexing a high number of targets) and a primer same as the 20 bases at 5' Y adapter overhang. A second round of PCR is carried out with a primer same as the 30 bases at the 5' Y adapter overhang and a second tandem nested target specific primer that anneals 3' downstream of the first target specific primer. The second tandem nested primer is 5' tagged with the second primer sequence required for downstream emulsion PCR or clustering depending on the sequencing technology. High specificity in this system is achieved with the unidirectional tandem, nested primers which will effectively cover a target sequence of 36-40 bases or more (depending on the spacing between the primers). Of note, the number of PCR cycles may be optimized depending on how much starting nucleic acid material is used, the number of pooled samples, and the number of targets.

In summary, the method utilizes a half-truncated Y adapter to universally tag all dsDNA fragments with a common 3' end which is utilized for two rounds of PCR using two unidirectional, nested target specific primers for specificity. The application of tagged nested primers also avoids the effects of primer homodimerization and heterodimerization when targeting many different sites in the genome or transcriptome. In addition to multiplexing targets, the methods described herein also allow for multiplex sample pooling after the Y adapter ligation (Step 2) during which individual samples are ligated with unique barcoded adapters. Once barcoded via Y adapter ligation, multiple samples may be pooled into one reaction tube for downstream target enrichment.

In contrast to detection of genomic rearrangements which is more tolerant of insertion and deletion sequencing errors such as those found on Ion Torrent™ and 454™ sequencing as a result of homopolymers, detection of single base and multiple base mutations (including insertions and deletions) requires higher accuracy sequencing achievable with the Illumina sequencing platform. For this purpose, the half-truncated Y adapted library can be converted to an Illumina library, e.g. by amplifying the overhanging, truncated 3' arm of the Y adapter using a primer tagged with the Illumina forward adapter sequence (barcoded or non-barcoded), and tagged gene specific nested primers (GSP2s tagged with Illumina reversed primer). Similarly, Bi-directional sequencing is also achievable by introducing a sequencing primer via the overhanging, truncated 3' Y adapter arm using a tagged primer during the first PCR, Step 3.

Figure 2:
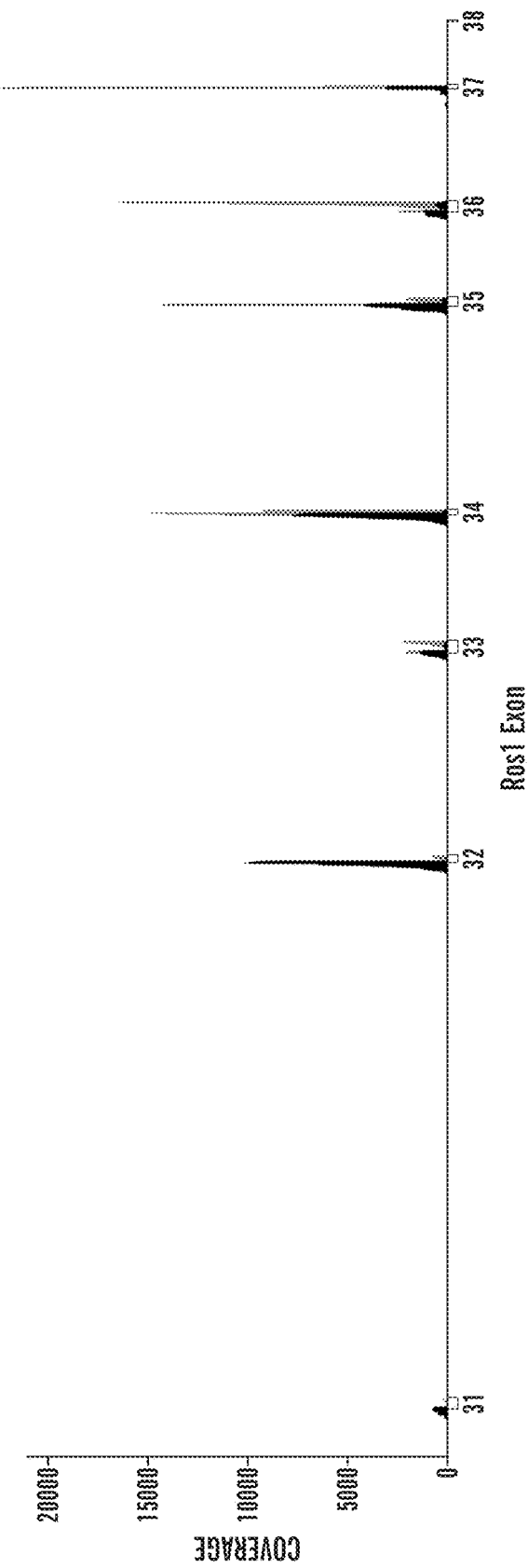
FIG. 2 depicts the mapping results, demonstrating different primer (dots) extension products in one sequencing run of ROS1 sequences, including reads that corresponding to genomic DNA (spanning intron-exon boundaries), cDNA (spanning exons) and fusion cDNA (on exon 34, mapping on the fusion partner SLC34A2 not shown here). 91.8% specificity (127,446/138,787) was achieved.

The assays and methods described herein have been applied on cDNA derived from FFPE specimens for the detection of ROS1 gene fusions using seven gene specific primers targeting seven exons comprising the ROS1 kinase domain. ROS1 genomic rearrangements were detected with known and previously unknown fusion partners such as "SLC34A2 Exon 12-ROS1 Exon 34" and "EZR Exon 9-ROS1 Exon 34" fusions. The assay achieved high on-target specificity (~85-95% when mapping using human genome hg19 reference), which enables the sequencing of multiple samples even with the smallest scale sequencing platforms (and thus least expensive) such as the Ion Torrent PGM 314™ chip with high coverage results (7 targeted loci, 5 samples, >1000 X coverage for each target per sample). FIG. 2 shows mapping of sequencing reads to the target loci in gene ROS1 kinase domain.

Advantages of the methods described herein include:

1. The methods described herein can be utilized for target enrichment of double stranded cDNA or gDNA from fresh or FFPE samples, allowing mapping of both 5' and 3' ends of target cDNA or gDNA fragments, using next-generation sequencing. Current hybridization-based approaches require days of preparation and hybridization, and show lower specificity with capture of near off-target sequences. Current amplification based approaches require known forward and reverse primers by design and are not amenable for high scale multiplexing of targets.

2. Simple Bioinformatics analysis. Depending on the number of selected targets, analysis of data generated from this assay is simple and fast. In addition, it may be set up to be compatible with current existing bioinformatics tools. Thus, small-size clinical labs may be able to perform data analysis without the need for significant investment in bioinformatics, which will be a limitation for broad clinical implementation of next generation sequencing.

3. High specificity (~85-95%). A conventional Y adapter construct having both components of forward and reverse primers (5' and 3' overhangs) for routine library construction will introduce a high level of background off-target sequencing due to carry over of "sequenceable" starting genomic or transcriptome library material. For instance, if the target is of size of 100 bp and present in two copies in one genome, the ratio of target-to-genome is about $1:3\times10^7$. Hybridization-based approaches normally employ biotinylated oligonucleotide baits to pull out hybridized target fragments by streptavidin coated magnetic beads. Just one non-specific binding event out of the possible $3\times10^7$ possibilities could dramatically result in a 50% off-target rate. The use of a half-truncated Y adapter effectively avoids this background carry over issue, since the starting library material cannot be amplified in subsequent preparatory steps for sequencing. Additional specificity is achieved by using two unidirectional primers, with GSP2 3' downstream of GSP1. Effectively, the use of the two tandem primers yields a target priming site of 40 (assume two 20 base pair length primers) and higher specificity than with just one primer. The use of 5' 20-mer primer in the first PCR and the full 30-mer primer (serves as a nested primer for the universal priming site) in the second PCR further increases specificity. Finally, additional specificity is achieved with the use of tagged primers for both PCR steps. Tagged primers, through intramolecular hairpin formation, prevent the propagation of primer homodimers and heterodimers which could overtake the PCR reactions and lead to nonspecific and undesired artifactual products; therefore, tagged primers allow the ability to multiplex many targets while avoiding primer dimers.

4. Economical cost. The key components in the methods described herein are conventional, unmodified tagged primers, standard PCR reagents, and routine thermocycling. Unlike hybridization based capture methods or microfluidic digital PCR setups, the described target enrichment protocol avoids the use of relatively expensive biotinylated oligo nucleotides, streptavidin coated magnetic beads, and special equipment. Once manufactured, pooled GSP1 and GSP2 primer mixes may be used for thousands of reactions.

5. Automation. Because the method described herein relies on standard PCR techniques and SPRI cleanup, there is potential for facile automation in high throughput applications. Volumes may be adjusted for 384 well plates for ultra-high throughput implementation.

Applications of the methods and assays described herein include, but are not limited to: 1. A lung cancer translocation panel consisting of known therapeutic targets including genes ALK, ROS1 and RET; 2. hematological malignancy panels including those to detect genomic rearrangements in lymphomas and leukemias; 3. Sarcoma genomic rearrangement panel; 4. IGH/TCR gene rearrangement panel for lymphoma testing; 5. Targeted disease gene panel for resequencing (10-100 genes); 6. Targeted resequencing for confirming variants from large scale sequencing projects; 7. Potential for whole exome targeted resequencing; 8. Targeted resequencing for detection of single nucleotide variants, multiple nucleotide variants, insertions, deletions, copy number changes, and methylation status; 9. Microbiota sequencing; 10. Ancient sample sequencing; 11. New variant virus genotyping.

Example 2: Targeted Next-Generation Sequencing Assay for Simultaneous Detection of ALK, ROS1 and RET Gene Rearrangements Knowledge of chromosomal rearrangement status in cancer is important for individualized targeted therapy. Recently, three major receptor tyROS1ine kinases involved in rearrangements in lung cancer have been described. Gene rearrangements involving the ALK gene has been established as a therapeutic target. Early clinical trial data also suggest that a ROS1 inhibitor is effective in treating patients testing positive for the ROS1 rearrangement. In vitro evidence has shown that tumor cells harbouring the RET rearrangement are responsive to a RET inhibitor. Thus, ALK, ROS1, and RET currently represent three important therapeutic targets in lung cancer.

Current clinical assays for the detection of gene rearrangements include fluorescence in situ hybridization (FISH), immunohistochemistry (IHC), and reverse transcription polymerase chain reaction (RT-PCR). FISH and IHC may not be able to accommodate the increasing demand for high volume testing/screening due to their low throughput, high cost, and complex interpretation. RT-PCR assays require full knowledge of both fusion partners which are sometimes unavailable and effectively impact clinical sensitivity. Multiplex RT-PCR has been used for detection of variant fusions involving different exons between two known fusion partners. In general, these assays are limited to a one gene target at a time approach requiring multiple reaction setups and analysis.

The latest next-generation sequencing-based assays for transcriptome or target capture sequencing have been applied largely for the purpose of research and discovery in large sequencing facilities. These assays in the research setting generally achieve low sequencing depth due to the vast number of targets, thus yielding low analytical sensitivity and subsequent poor clinical sensitivity. Though affordable for large sequencing facilities, these assays are not yet within reach for many clinical laboratories.

Described above are methods and assays related to a targeted sequencing method which applies a novel half-truncated "Y" shape adapter for next generation sequencing library construction followed by two single-end nested polymerase chain reactions enabling rapid and efficient target enrichment using RNA or genomic DNA as template from fresh or formalin-fixed and paraffin-embedded (FFPE) specimens.

Figure 3A:
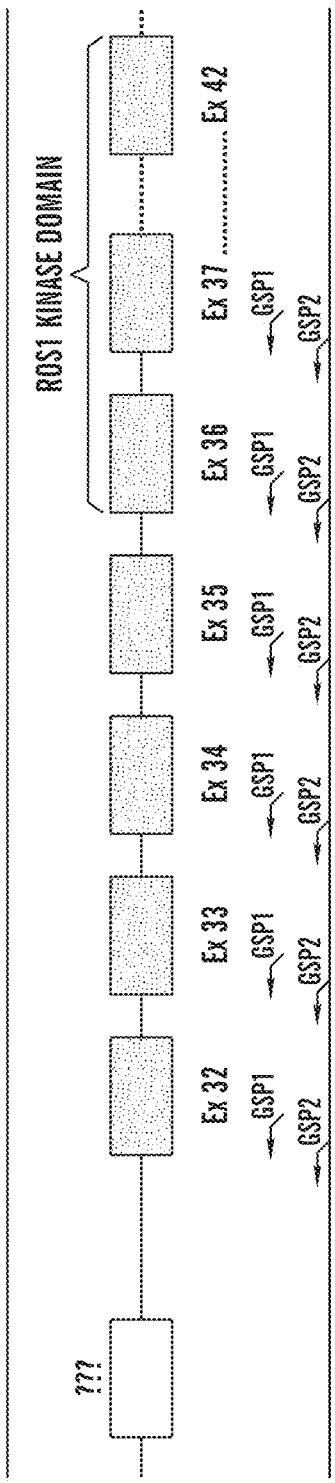
FIG. 3A depicts a schematic presentation of nested primer targeting strategy using ROS1 as an example. The assay target panel includes a total of 17 pairs of GSP1s and GSP2s for ROS1, ALK and RET.
Figure 3B:
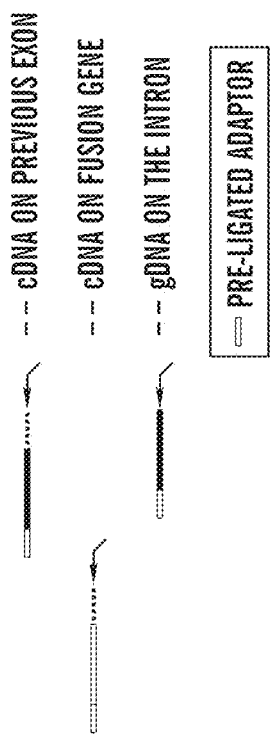
FIG. 3B depicts a representation of the possible types of extension products using gDNA and cDNA templates.

Based on this method, described in this Example is a specific assay for the detection of ALK, ROS1, and RET gene rearrangements (FIGS. 3A-3B). Gene specific primers (GSP1) are designed to prime the exons near or on the kinase domain. Nested primers (GSP2) are designed to prime downstream of GSP1 but within the same exons and proximity to their paired GSP1s. The panel currently includes seven pairs of primers for targeting ROS1 exons 31 to 37; four pairs of primers for targeting ALK exons 19 to 22; and six pairs of primers for targeting RET exons 8 to 13.

Figure 4A:
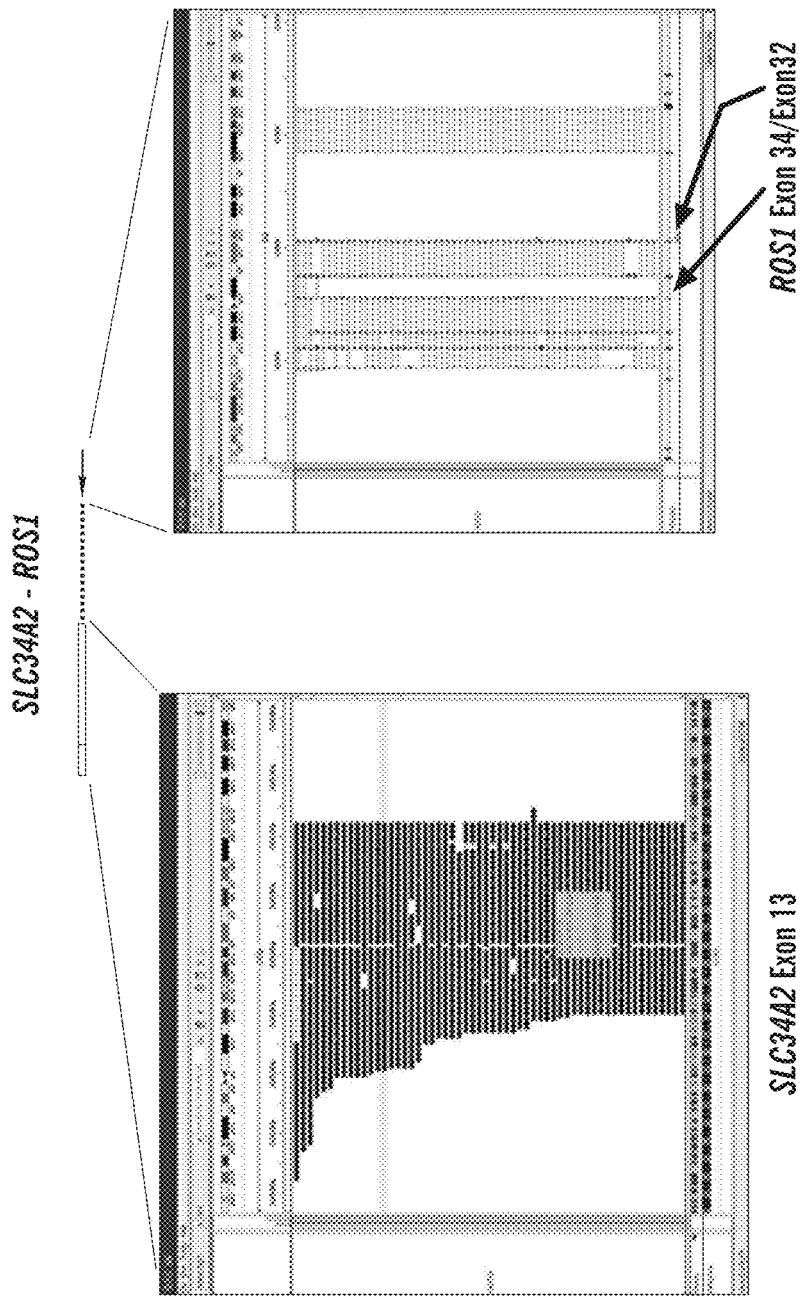
FIG. 4A depicts the visualization of reads mapping using the Integrative Genomics Viewer.
Figure 5:
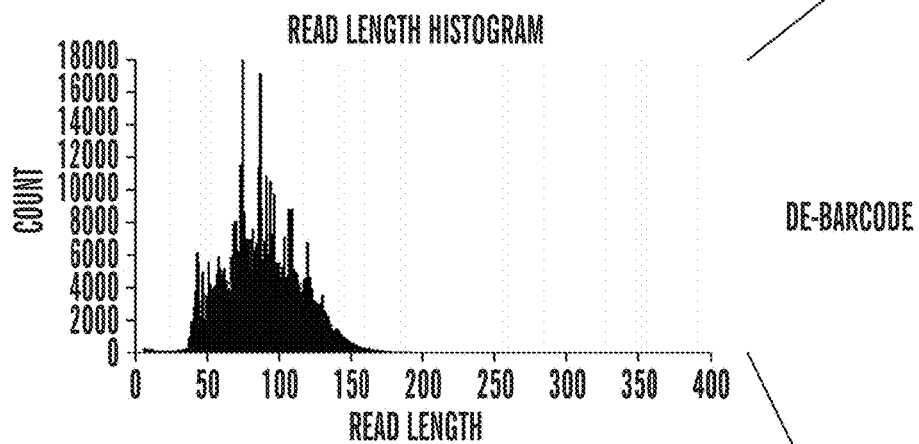
FIG. 5 depicts the results of an example sequencing run. Sequences shown are ctaaggtaac (SEQ ID NO: 49), taaggagaac (SEQ ID NO: 50), aagaggattc (SEQ ID NO: 51), taccaagatc (SEQ ID NO: 52), cagaaggaac (SEQ ID NO: 53), ctgcaagttc (SEQ ID NO: 54) ttcgtgattc (SEQ ID NO: 55), ttccgataac (SEQ ID NO: 56), ctgaccgaac (SEQ ID NO: 57), tcctcgaatc (SEQ ID NO: 58), taggtggttc (SEQ ID NO: 59) and tctaacggac (SEQ ID NO: 60).
Figure 5:
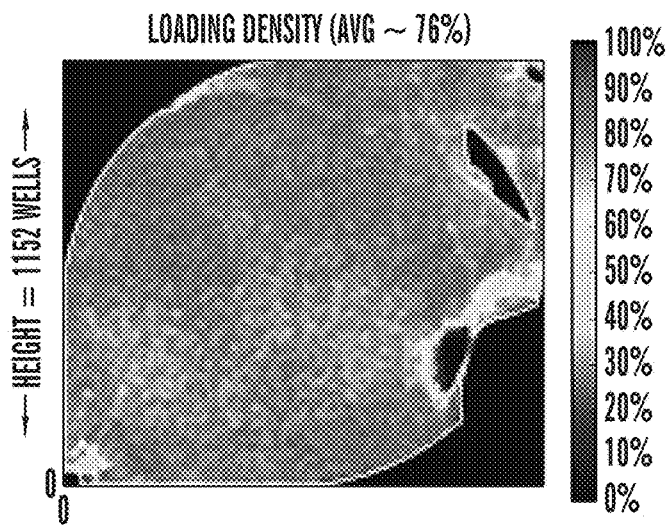
Figure 5:
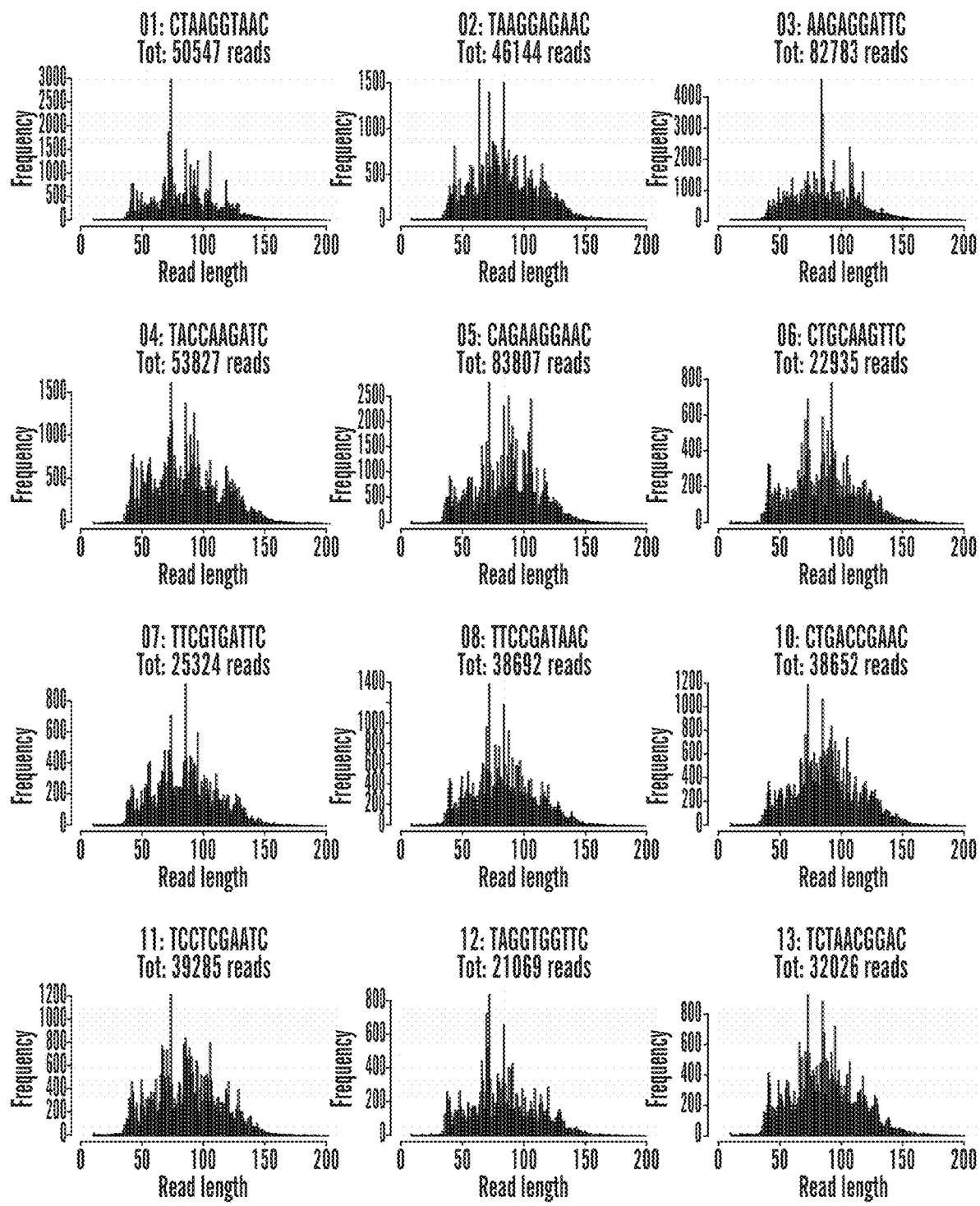
Figure 6:
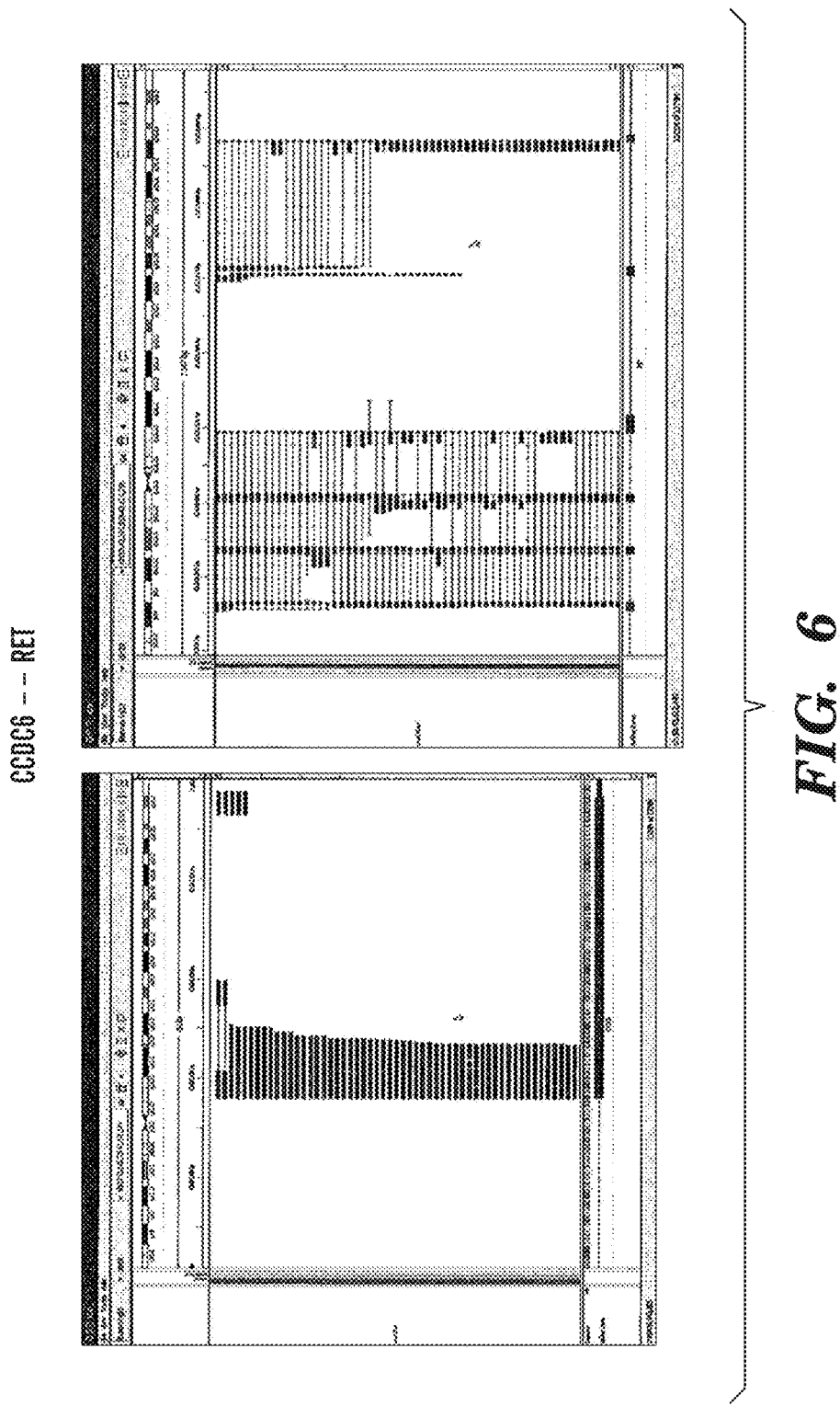
FIGS. 6 and 7 depict examples of the results of sequencing runs for ALK and RET sequences, respectively.
Figure 7:
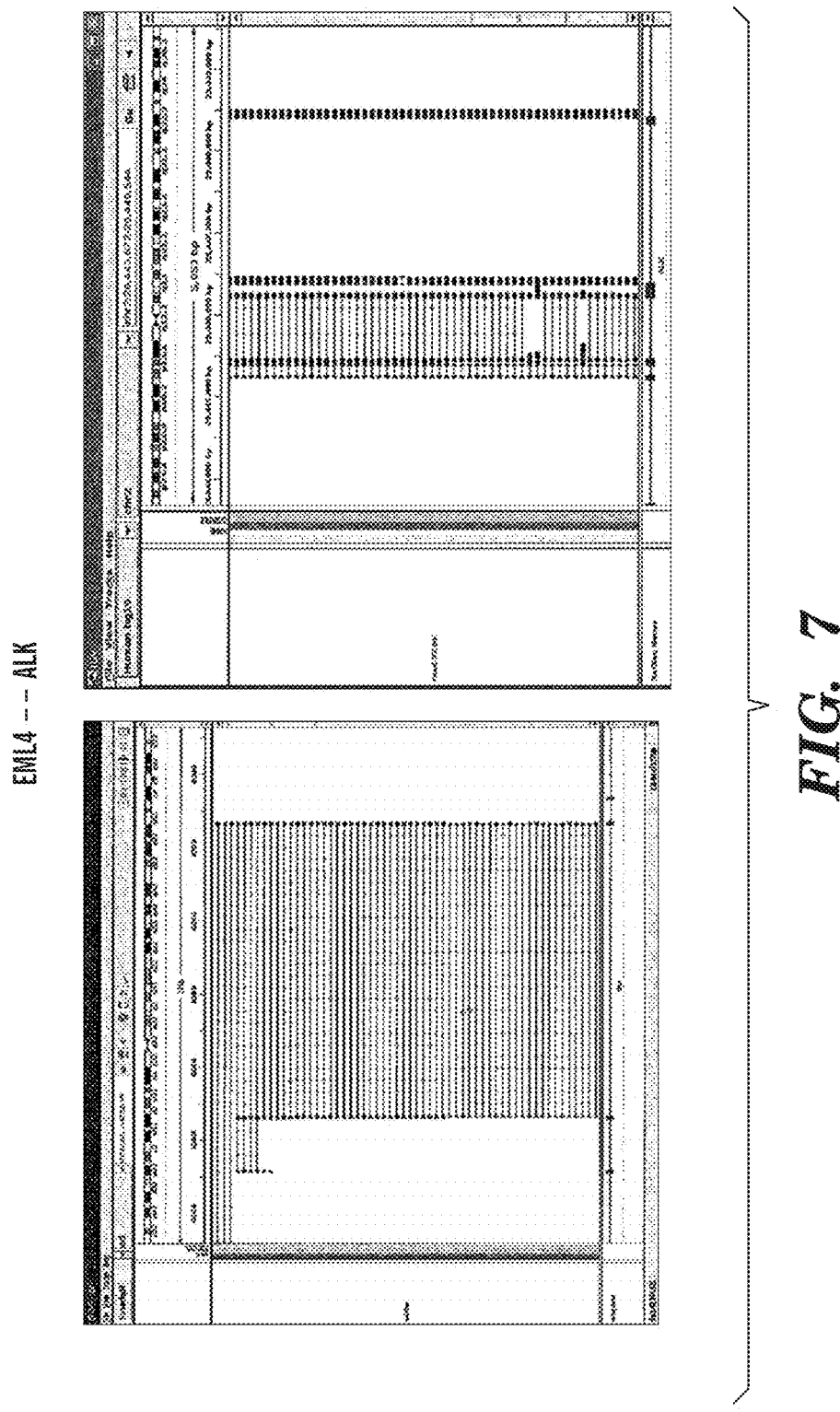
Figure 8:
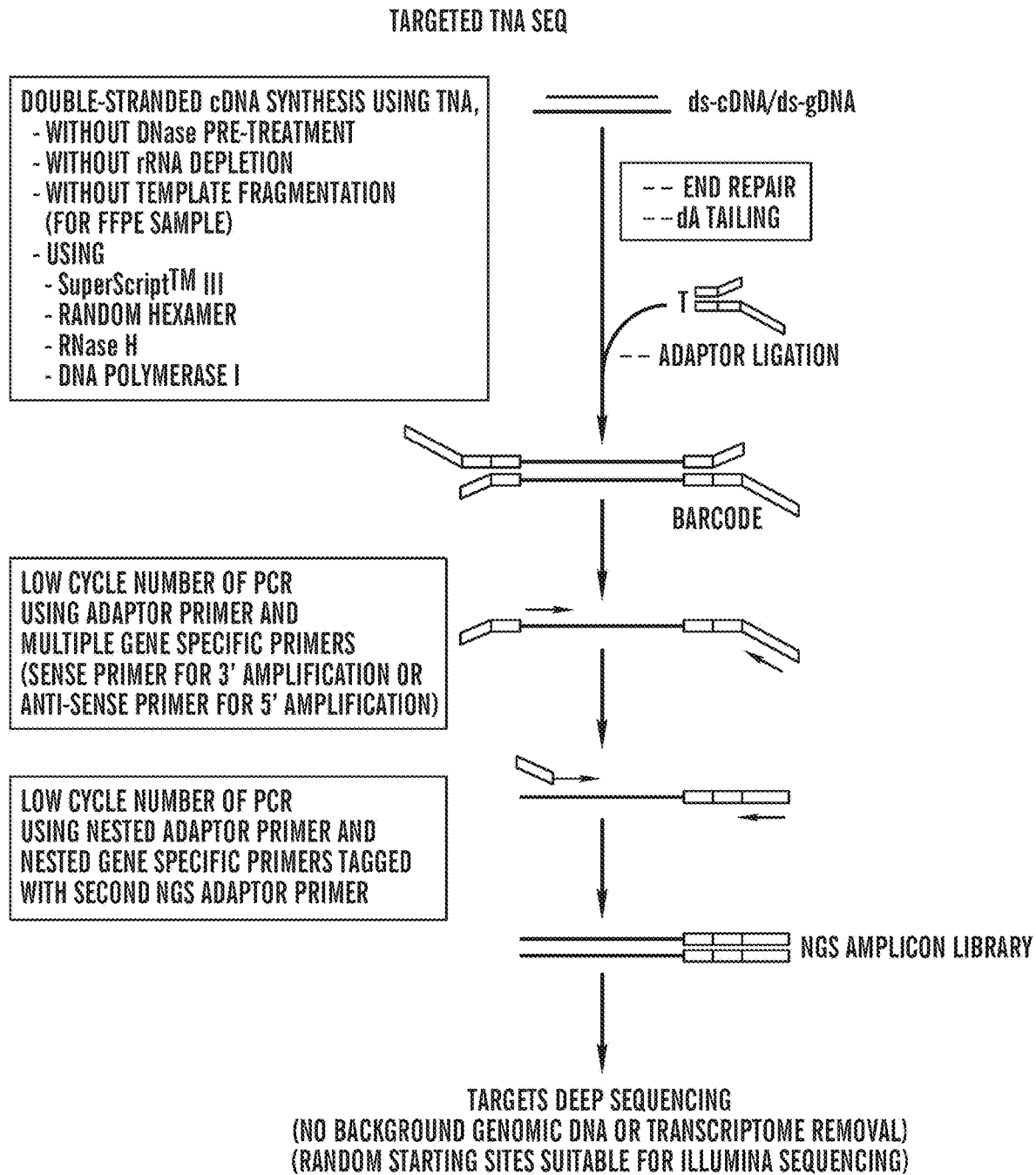
FIG. 8 depicts a schematic presentation of the targeted sequencing approach described herein.

This assay can be adapted to different NGS sequencing platforms by using platform specific adaptor sequence following the half-functional "Y" adaptor configuration and the GSP2 primers. After sequencing, the reads are mapped to the human genome reference allowing the identification of fusion partner genes, alternative splicing, as well as frame status of the fusions using a bioinformatics algorithm developed by the inventors (e.g. FIGS. 4A and 4B). The resulting output is a simple annotated table for quick reporting (FIG. 4C). Using this three gene target panel assay with multi-sample barcoding, ROS1, ALK and RET rearrangement positive samples have been detected using one Ion Torrent™ sequencing run.

This assay is applicable for degraded RNA, such as RNA extracted from formalin-fixed and paraffin-embedded (FFPE) specimen, which is the most widely available clinical material for molecular diagnostic testing. This assay takes advantage of bench-top NGS platforms, a simple informatics analysis pipeline, and therefore relatively easy implementation for clinical laboratories. Of note, this assay does not require prior knowledge of the fusion partners and would yield high clinical sensitivity in the detection of various gene partners (and corresponding multiple exons) associated with the principle target gene. In addition, the assay will be functional for both unknown 5' upstream or 3' downstream fusion partners as long as one of the partners is known. Multiplexing and deep sequencing allows testing of samples with low tumor cellularity, rare fusions, and rare alternative splicing events. The detailed, patient specific rearrangement information afforded by this assay would be useful for evaluating genotype specific therapeutic response and perhaps a patient specific tumor marker for minimal residual disease monitoring. Based on conventional oligo synthesis reagents, off the shelf enzymes, and the ability to multiplex many samples in one run, this assay will be a cost-effective clinical assay for detecting gene rearrangements.

TABLE 1

Primers adapted for IonTorrent ™ platform, v1. Primer names indicate target gene and target gene exon comprising the known target nucleotide sequence. R1 designates a first target-specific primer and R2 designates a second target-specific primer. Detailed in this table is one set of a first target specific primer and one second target-specific for each listed exon of each gene.

| Primer Name | Sequence | SEQ ID NO |
|---|---|---|
| ALKex19_P1R2 | CCTCTCTATGGGCAGTCGGTGATGCGAGAGTGGCAGGTGTGG | 5 |
| ALKex19_tag.R1 | GGATCTCGACGCTCTCCCTCAGAGGTCACCACAGAGAGGATCAG | 6 |
| ALKex20_P1R2 | CCTCTCTATGGGCAGTCGGTGATCATGGCTTGCAGCTCCTGGT | 7 |
| ALKex20_tag.R1 | GGATCTCGACGCTCTCCCTGCAGCTCCATCTGCATGGCTTG | 8 |
| ALKex21_P1R2 | CCTCTCTATGGGCAGTCGGTGATGGCCTTCATACACCTCCCCAAA | 9 |
| ALKex21_tag.R1 | GGATCTCGACGCTCTCCCTTTGGGCATTCCGGACACC | 10 |
| ALKex22_P1R2 | CCTCTCTATGGGCAGTCGGTGATAGGAAATCCAGTTCGTCCTGTTCAGA | 11 |
| ALKex22_tag.R1 | GGATCTCGACGCTCTCCCTGATCAGGGCTTCCATGAGGAAATC | 12 |
| RETex10_P1R2 | CCTCTCTATGGGCAGTCGGTGATGGCTCCCCAGGCTCGTGT | 13 |
| RETex10_tag.R1 | GGATCTCGACGCTCTCCCTAGGTGCCATAGCCAGCTTTAATCC | 14 |
| RETex11_P1R2 | CCTCTCTATGGGCAGTCGGTGATATCACCGTGCGGCACAGCTC | 15 |
| RETex11_tag.R1 | GGATCTCGACGCTCTCCCTGAGGACAGCGGCTGCGATCA | 16 |
| RETex12_P1R2 | CCTCTCTATGGGCAGTCGGTGATAGAACCAAGTTCTTCCGAGGGAAT | 17 |
| RETex12_tag.R1 | GGATCTCGACGCTCTCCCTTCCAAATTCGCCTTCTCCTAGAGTT | 18 |
| RETex13_P1R2 | CCTCTCTATGGGCAGTCGGTGATACAGCAGGTCTCGCAGCTCAC | 19 |
| RETex13_tag.R1 | GGATCTCGACGCTCTCCCTTGACCTGCTTCAGGACGTTGAA | 20 |
| RETex8_P1R2 | CCTCTCTATGGGCAGTCGGTGATCTTGCTGACTGCACAGGACAGG | 21 |
| RETex8_tag.R1 | GGATCTCGACGCTCTCCCTTCCTCACACTCCAGCCGTCTC | 22 |
| RETex9_P1R2 | CCTCTCTATGGGCAGTCGGTGATTGGTGCTGGGAGAGCAGGT | 23 |
| RETex9_tag.R1 | GGATCTCGACGCTCTCCCTCCGTCGGGGCAGGTCTTG | 24 |
| ROS1Ex31_P1R2 | CCTCTCTATGGGCAGTCGGTGATGGCTGCATGAAGTTTTAACATGG | 25 |
| ROS1Ex31_tag.R1 | GGATCTCGACGCTCTCCCTTGATATTACAGACATAAGCAGGACCTTGG | 26 |
| ROS1Ex32_P1R2 | CCTCTCTATGGGCAGTCGGTGATCTAGTAATTTGGGAATGCCTGGTTT | 27 |
| ROS1Ex32_tag.R1 | GGATCTCGACGCTCTCCCTTTCAGCTTTCTCCCACTGTATTGAA | 28 |
| ROS1Ex33_P1R2 | CCTCTCTATGGGCAGTCGGTGATCATCTTCCACCTTAAATTCTGGTTCTGTA | 29 |

TABLE 1-continued

Primers adapted for IonTorrent ™ platform, v1. Primer names indicate target gene and target gene exon comprising the known target nucleotide sequence. R1 designates a first target-specific primer and R2 designates a second target-specific primer. Detailed in this table is one set of a first target specific primer and one second target-specific for each listed exon of each gene.

| Primer Name | Sequence | SEQ ID NO |
|---|---|---|
| ROS1Ex33_tag.R1 | GGATCTCGACGCTCTCCCTCAGGATCCATTAAATGTCATCTTCC | 30 |
| ROS1Ex34_P1R2 | CCTCTCTATGGGCAGTCGGTGATAGTAAGTATGAAACTTGTTTCTGGTATCC | 31 |
| ROS1Ex34_tag.R1 | GGATCTCGACGCTCTCCCTGGTCAGTGGGATTGTAACAACCAG | 32 |
| ROS1Ex35_P1R2 | CCTCTCTATGGGCAGTCGGTGATCACCCCTTCCTTGGCACTTT | 33 |
| ROS1Ex35_tag.R1 | GGATCTCGACGCTCTCCCTTCTTTGTCTTCGTTTATAAGCACTGTC | 34 |
| ROS1Ex36_P1R2 | CCTCTCTATGGGCAGTCGGTGATTTCAATCTCCTCTTGGGTTGGA | 35 |
| ROS1Ex36_tag.R1 | GGATCTCGACGCTCTCCCTCCGAGGGAAGGCAGGAAGATT | 36 |
| ROS1Ex37_P1R2 | CCTCTCTATGGGCAGTCGGTGATCAGGAATTCAATCTTCTCCTGGTC | 37 |
| ROS1Ex37_tag.R1 | GGATCTCGACGCTCTCCCTCTCATCAGATGTGCCTCCTTCAG | 38 |

What is claimed herein is:

1. A method for determining a nucleotide sequence, the method comprising:
  (a) amplifying a nucleic acid template comprising a 3'-end comprising a known target nucleotide sequence, a first nucleotide sequence contiguous to the known target nucleotide sequence, and a 5-end comprising an amplification strand of a ligated universal oligonucleotide tail-adaptor, using (i) a first primer that comprises a nucleotide sequence identical to a 5' portion of a first sequencing primer and (ii) a second primer that anneals to the 3-end of the nucleic acid template comprising the known target nucleotide sequence, thereby generating a first amplification product comprising the first nucleotide sequence and the known target nucleotide sequence;
  (b) amplifying the first amplification product of (a) using (i) a third primer that comprises a nucleotide sequence identical to a portion of the first sequencing primer and is nested relative to the first primer and (ii) a fourth primer that comprises a 5' portion comprising a nucleic acid sequence that is identical to a second sequencing primer, anneals to a 3' portion of the first amplification product comprising the known target nucleotide sequence, and is nested relative to the second primer, thereby generating a second amplification product; and
  (c) determining the sequence of the first nucleotide sequence in the second amplification product.

2. The method of claim 1, wherein step (c) comprises sequencing the second amplification product using at least the first sequencing primer.

3. The method of claim 2, wherein the sequencing of the second amplification product further comprises using a second sequencing primer substantially identical to a portion of the fourth primer.

4. The method of claim 1, wherein the amplification strand comprises a barcode portion and the second amplification product comprises the barcode portion.

5. The method of claim 1, wherein the first nucleotide sequence comprises a genetic alteration.

6. The method of claim 1, wherein the nucleic acid template comprises DNA.

7. The method of claim 1, wherein the first nucleotide sequence comprises an insertion or deletion.

8. The method of claim 1, wherein the nucleic acid template comprises cDNA.

9. The method of claim 1, wherein the second primer comprises a 3'-end substantially complementary to the known target nucleotide sequence and a 5' tag sequence portion comprising a GC content of at least 65%.

10. The method of claim 1, wherein the known target nucleotide sequence and/or the first nucleotide sequence comprises a sequence comprising a gene rearrangement.

11. The method of claim 10, wherein the gene rearrangement comprises a fusion oncogene.

12. The method of claim 1, wherein the nucleic acid template is prepared from a sample obtained from a subject having a condition associated with a genetic alteration.

13. The method of claim 1, wherein the known target nucleotide sequence and/or the first nucleotide sequence comprises a sequence from a gene selected from the group of: anaplastic lymphoma kinase (ALK); c-ros oncogene 1 (ROS1); and rearranged during transfection (RET).

14. A method for determining a nucleotide sequence, the method comprising:
  (a) ligating an amplification strand of a universal oligonucleotide tail-adaptor to a 5'-end of a nucleic acid template comprising (i) a 3-end comprising a known target nucleotide sequence and (ii) a first nucleotide sequence contiguous to the known target nucleotide sequence;
  (b) amplifying the nucleic acid template using (i) a first primer that comprises a nucleotide sequence identical to a 5' portion of a first sequencing primer and (ii) a second primer that anneals to the 3'-end of the nucleic acid template comprising the known target nucleotide sequence, thereby generating a first amplification product comprising the first nucleotide sequence and the known target nucleotide sequence;
  (c) amplifying the first amplification product of (b) using (i) a third primer that comprises a nucleotide sequence identical to a portion of the first sequencing primer and that is nested relative to the first primer and (ii) a fourth primer that comprises a 5' portion comprising a nucleic acid sequence that is identical to a second sequencing primer, anneals to a 3' portion of the first amplification product comprising the known target nucleotide sequence and is nested relative to the second primer, thereby generating a second amplification product comprising the first nucleotide sequence; and
  (d) determining the sequence of the first nucleotide sequence in the second amplification product by a process comprising next-generation sequencing.

* * * * *